(12) United States Patent
Ohno et al.

(10) Patent No.: US 6,248,074 B1
(45) Date of Patent: Jun. 19, 2001

(54) ULTRASONIC DIAGNOSIS SYSTEM IN WHICH PERIPHERY OF MAGNETIC SENSOR INCLUDED IN DISTAL PART OF ULTRASONIC ENDOSCOPE IS MADE OF NON-CONDUCTIVE MATERIAL

(75) Inventors: Masahiro Ohno, Kunitachi; Kenji Kishi, Yokohama; Tomonao Kawashima, Hachioji; Ichiro Odachi, Hino, all of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/164,053

(22) Filed: Sep. 30, 1998

(30) Foreign Application Priority Data

| Sep. 30, 1997 | (JP) | 9-264703 |
| Oct. 14, 1997 | (JP) | 9-280835 |
| Oct. 16, 1997 | (JP) | 9-283915 |
| Oct. 28, 1997 | (JP) | 9-295797 |

(51) Int. Cl.$^7$ ............................................. A61B 8/12
(52) U.S. Cl. ............................ 600/463; 128/916; 600/117
(58) Field of Search .................................. 600/459–463, 600/117, 118; 128/899, 916

(56) References Cited

U.S. PATENT DOCUMENTS

| 4,802,487 | * | 2/1989 | Martin et al. | 600/463 |
| 5,199,437 | * | 4/1993 | Langberg | 600/456 |
| 5,353,354 | | 10/1994 | Keller et al. | |
| 5,398,691 | | 3/1995 | Martin et al. | |
| 5,997,473 | | 12/1999 | Taniguchi et al. | 600/117 |

FOREIGN PATENT DOCUMENTS

| 62-68442 | 3/1987 | (JP) . |
| 4332544 | 11/1992 | (JP) . |
| 6030937 | 2/1994 | (JP) . |
| 6261900 | 9/1994 | (JP) . |

* cited by examiner

Primary Examiner—Francis J. Jaworski

(57) ABSTRACT

An ultrasonic transducer for producing an ultrasonic tomographic image is included in a distal part of an ultrasonic endoscope to be inserted into an object of observation. The ultrasonic transducer is rotated. Echoes of ultrasonic waves produced by the ultrasonic transducer are detected in order to produce an ultrasonic tomographic image that is a two-dimensional image. A magnetic sensor for detecting a position is included in the distal part. A magnetic field generated by a magnetic field generator locked near the object of observation is sensed. The position and orientation of the distal part are detected, whereby information of a position and orientation relevant to the ultrasonic tomographic image is obtained. Based on the information of the position and orientation, a plurality of produced ultrasonic tomographic images is synthesized in order to produce an ultrasonic image that is a three-dimensional image. The periphery of the magnetic sensor in the distal part is made of a non-conductive material. An eddy current developing near the magnetic sensor is therefore limited. Consequently, the precision in position detection performed by the magnetic sensor improves. The precision in position relevant to each of the ultrasonic tomographic images constituting the ultrasonic image therefore improves. Thus, an ultrasonic image with high positional precision can be produced.

21 Claims, 34 Drawing Sheets

ULTRASONIC TOMOGRAPHIC IMAGE

REGION OF INTEREST

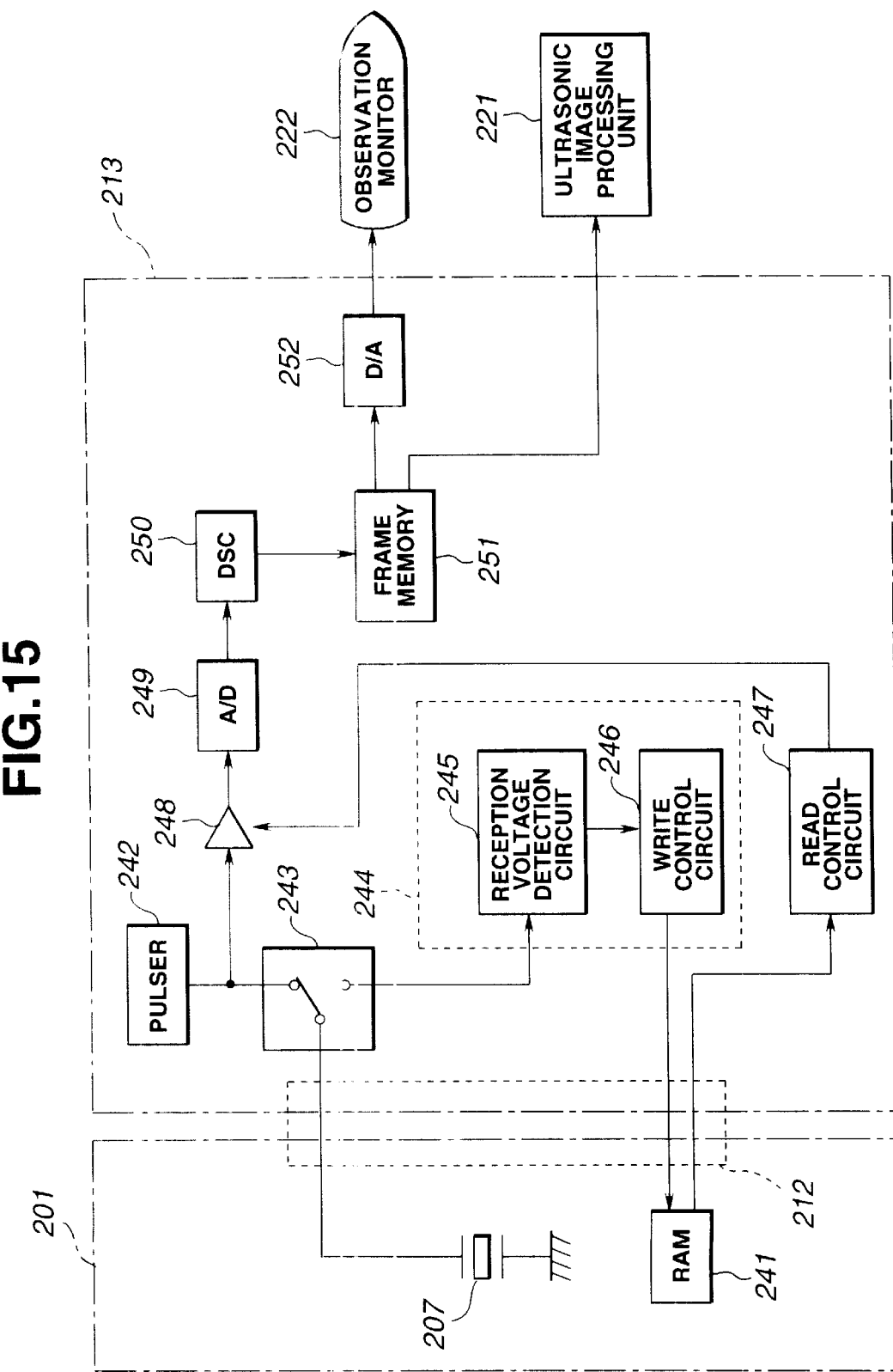

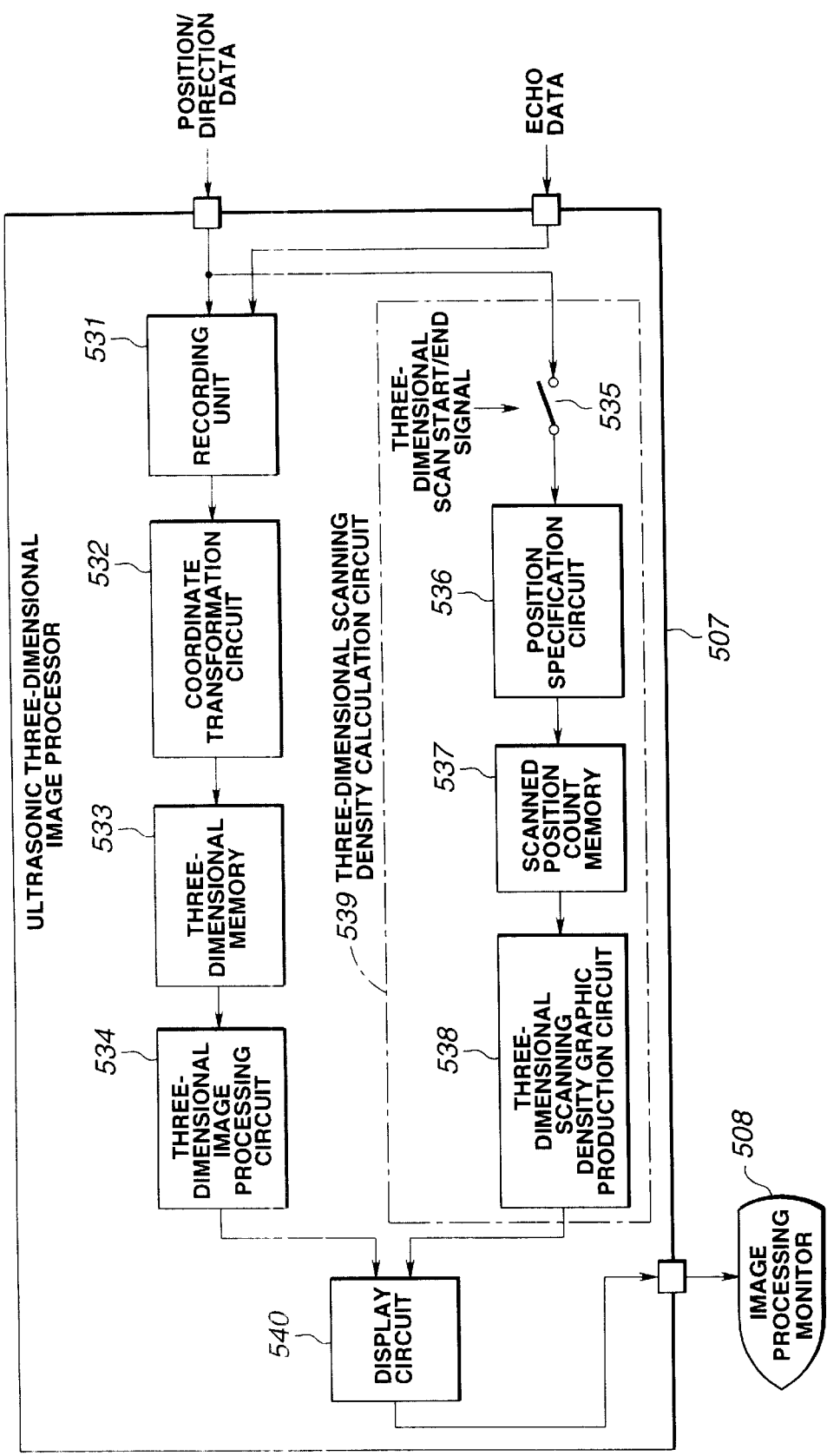

ULTRASONIC DIAGNOSIS SYSTEM IN WHICH PERIPHERY OF MAGNETIC SENSOR INCLUDED IN DISTAL PART OF ULTRASONIC ENDOSCOPE IS MADE OF NON-CONDUCTIVE MATERIAL

BACKGROUND OF THE INVENTION

1. Field of the Invention

The present invention relates to an ultrasonic diagnosis system for producing an ultrasonic image with high positional precision. In the ultrasonic diagnosis system, the periphery of a magnetic sensor in a distal part of an ultrasonic probe, which has an ultrasonic transducer for producing an ultrasonic tomographic image and the magnetic sensor for detecting a position, is made of a non-conductive material in order to reduce an eddy current developing in the periphery of the magnetic sensor and to thus improve the precision in detecting the position of the distal part.

2. Description of the Related Art

In recent years, ultrasonic diagnosis systems for irradiating ultrasonic waves to the inside of a living body, extracting information of an intracorporeal state from echoes, and thus diagnosing a lesion have prevailed widely. Above all, an ultrasonic diagnosis system including an ultrasonic probe for irradiating ultrasonic waves intra-corporeally suffers less decay of ultrasonic waves than a type of ultrasonic diagnosis system that irradiates ultrasonic waves extra-corporeally. High-frequency ultrasonic waves of a high resolution can therefore be employed.

Japanese Unexamined Patent Publication No. 6-261900, describes prior art for detecting the position of an ultrasonic transducer by moving the ultrasonic transducer spirally and utilizing a magnetic field, and constructing a three-dimensional image.

FIG. 1 shows the structure of a prior art distal part 102 of an ultrasonic endoscope 101 serving as an ultrasonic probe. The distal part 102 consists of a distal body 105 attached to the distal end of a casing 104 outlining an insertion unit 103, and a housing 106. An illumination window 107 and objective window 108 are juxtaposed on an inclined surface formed near the center of the distal body 105. A passage hole 110 through which a flexible shaft 109 lies is bored in the distal body 105. The housing 106 communicating with the passage hole 110 is mounted on the distal end of the distal body 105.

A holder 112 having an ultrasonic transducer 111 is located at the distal end of the flexible shaft 109. The ultrasonic transducer 111 is placed in the housing 106. A sealing member 113 for sealing the housing 106 is attached to the proximal end of the holder 112. The housing 106 is filled with an ultrasound propagation fluid (for example, water) 114. A magnetic sensor 115 serving as a position sensor is located at the distal end of the housing 106.

Due to the foregoing structure, the flexible shaft 109 is rotated by a rotation unit that is not shown. This results in radial scanning. Spiral scanning is achieved by advancing or withdrawing the insertion unit 103, that is, advancing or withdrawing the ultrasonic transducer 111. A magnetic field generator is installed extra-corporeally. A magnetic field is detected by the magnetic sensor 115, and sent to a position detector that is an external apparatus. Based on position data computed by involving the position detector, a three-dimensional image is constructed using numerous two-dimensional images resulting from spiral scanning by means of an external apparatus. The image is then displayed on a monitor.

As for the foregoing position sensor-inclusive ultrasonic endoscope, all components thereof including the distal body are made of a conductive material such as a metal. In a magnetic field generated by the magnetic field generator, an eddy current develops on each conductor to consume magnetic energy. This leads to a phenomenon that a magnetic field reaching the magnetic sensor 115 is disordered. Consequently, position detection is not achieved correctly, and a measurement error occurs.

SUMMARY OF THE INVENTION

The present invention provides an ultrasonic diagnosis system for producing an ultrasonic image with high positional precision by reducing an eddy current that develops around a magnetic sensor and by improving precision in position detection.

According to a preferred embodiment, the ultrasonic diagnosis system comprises an ultrasonic endoscope to be inserted into an object of observation, an ultrasonic transducer included in a distal part of the ultrasonic endoscope for producing an ultrasonic tomographic image, and a magnetic sensor included in the distal part for detecting the position of the ultrasonic transducer. The periphery of the magnetic sensor in the distal part of the ultrasonic diagnosis system is made of a non-conductive material. Consequently, an eddy current developing in the periphery of the magnetic sensor is reduced, and precision in position detection is improved. This enables provision of an ultrasonic diagnosis system capable of producing an ultrasonic image with high positional precision.

BRIEF DESCRIPTION OF THE DRAWINGS

FIG. 2 is a schematic view of an ultrasonic diagnosis system including an ultrasonic endoscope;

FIG. 3 is a diagram showing a distal part of the ultrasonic endoscope;

FIG. 5 shows the structures of an ultrasonic endoscope of an ultrasonic diagnosis system and of a position detection catheter;

FIG. 6 is a block diagram showing the configuration of the ultrasonic diagnosis system including an ultrasound observation unit and ultrasonic image processing unit;

FIG. 7 is a diagram showing an example of image data representing a plurality of consecutive ultrasonic tomographic images;

FIG. 8 is a diagram showing an example of a three-dimensional image constructed based on three-dimensional data;

FIGS. 15 and 16 relate to the seventh embodiment of the present invention;

FIG. 15 is a block diagram showing an example of a configuration including an ultrasonic endoscope and ultrasonic observation unit;

FIG. 16 is a block diagram showing another configuration different from the one shown in FIG. 15;

FIG. 17 is a diagram showing the configuration of an ultrasonic diagnosis system;

FIG. 18 is a diagram showing the structure of the distal part of the ultrasonic endoscope;

FIGS. 26 to 35 relate to the sixteenth embodiment of the present invention;

FIG. 26 is an explanatory diagram showing the overall configuration of an ultrasonic diagnosis system;

FIG. 27 is a perspective view showing a distal part of an ultrasonic endoscope in enlargement;

FIG. 28 is a block diagram showing the configuration of an ultrasonic three-dimensional image processor;

FIG. 30 is an explanatory diagram concerning an operation of the ultrasonic three-dimensional image processor, showing a three-dimensional scanning density graphic;

FIG. 31 is an explanatory diagram concerning an operation of the ultrasonic three-dimensional image processor, showing an example of displaying a three-dimensional ultrasonic image of an examined region;

FIG. 32 is an explanatory diagram concerning an operation of the ultrasonic three-dimensional image processor, showing an example of displaying a three-dimensional ultrasonic image of an examined region;

FIG. 33 is an explanatory diagram concerning an operation of the ultrasonic three-dimensional image processor, showing an example of displaying a three-dimensional ultrasonic image of an examined region;

FIG. 34 is a flowchart describing a procedure of section setting carried out by a three-dimensional image processing circuit;

FIG. 35 is an explanatory diagram concerning an operation of the three-dimensional image processing circuit, showing a plurality of sectional images appearing when sections used to produce a three-dimensional ultrasonic image are set;

FIG. 36A is an explanatory diagram concerning an operation of the three-dimensional image processing circuit, showing a method of displaying a graphic that depicts three-dimensional scanning densities;

FIG. 36B is an explanatory diagram showing an operation of the three-dimensional image processing circuit, illustrating the method of displaying a graphic that depicts three-dimensional scanning densities;

DESCRIPTION OF THE PREFERRED EMBODIMENTS

The first embodiment of the present invention will be described below.

Figure 1:
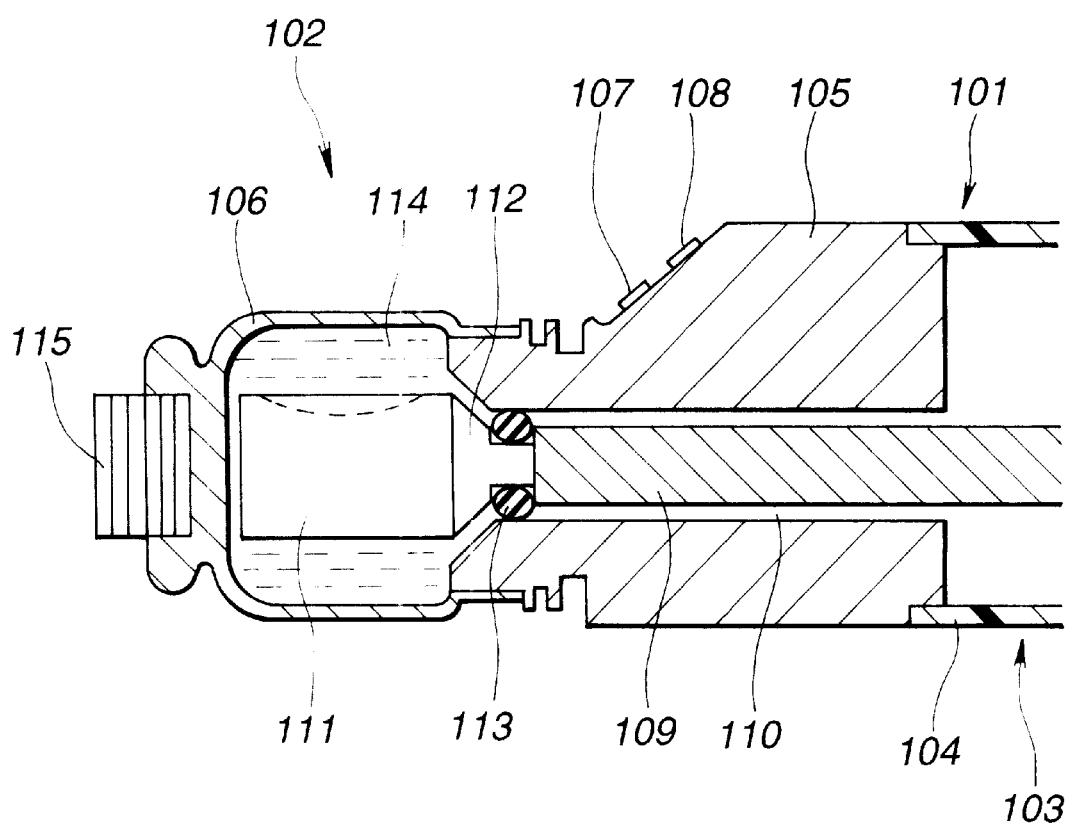
FIG. 1 is a diagram showing a distal part of an ultrasonic diagnosis system in accordance with a prior art.
Figure 2:
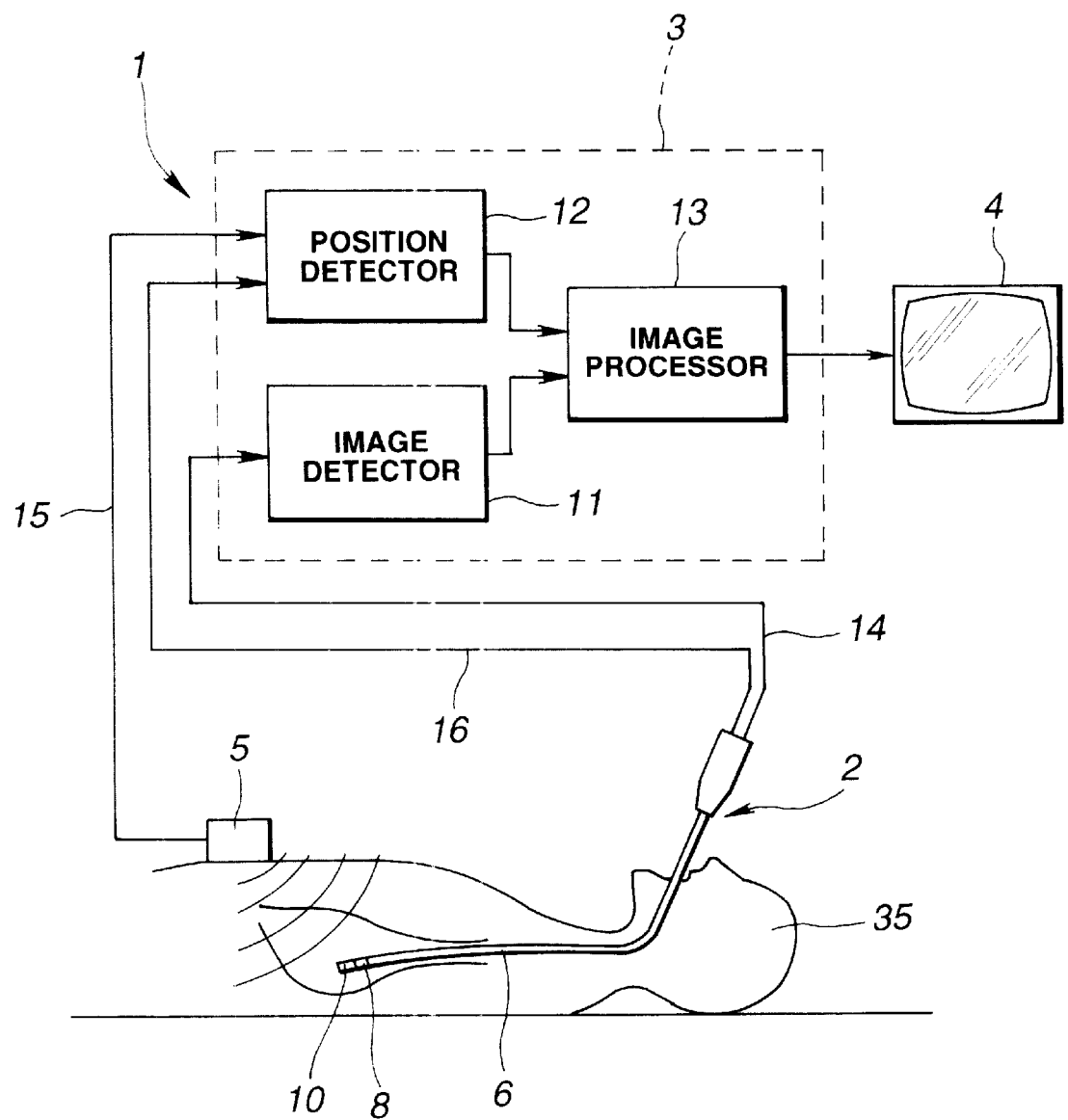
FIGS. 2 and 3 relate to the first embodiment of the present invention.

FIG. 2 shows an ultrasonic diagnosis system 1. The ultrasonic diagnosis system 1 consists of an ultrasonic endoscope 2, a host processor 3, a monitor 4, and a magnetic field transmitter 5 serving as a magnetic field generator.

The ultrasonic endoscope 2 is provided with an ultrasound transmitter receiver 8 that has an ultrasonic transducer 7 (FIG. 3) included in the distal part of an elongated insertion unit 6 to be inserted into a body cavity, and a position detector 10 having a magnetic sensor 9 for detecting the position of the ultrasound transmitter receiver 8.

The host processor 3 to which the ultrasonic endoscope 2 is connected consists of an image detector 11, a position detector 12, and an image processor 13. The image detector 11 transmits or receives a signal used to drive the ultrasonic transducer 7 and image data sent from the ultrasonic transducer 7 over a signal line 14, and stores them as the image data. The position detector 12 receives a reference signal from the magnetic field transmitter 5 over a signal line 15. Moreover, the position detector 12 receives a detection signal from the magnetic sensor 9, which detects a magnetic field induced by the magnetic field transmitter 5, over a signal line 16. The image processor 13 simultaneously fetches two-dimensional ultrasonic image data sent from the image detector 11, and position data that indicates positions relevant to two-dimensional ultrasonic images and that is sent from the position detector 12. The image processor 13 then constructs a three-dimensional ultrasonic image using the two-dimensional ultrasonic images. The image processing composed of these steps has been disclosed in Japanese Unexamined Patent Publication No. 6-261900. The three-dimensional ultrasonic image is displayed on the monitor 4.

Figure 3:
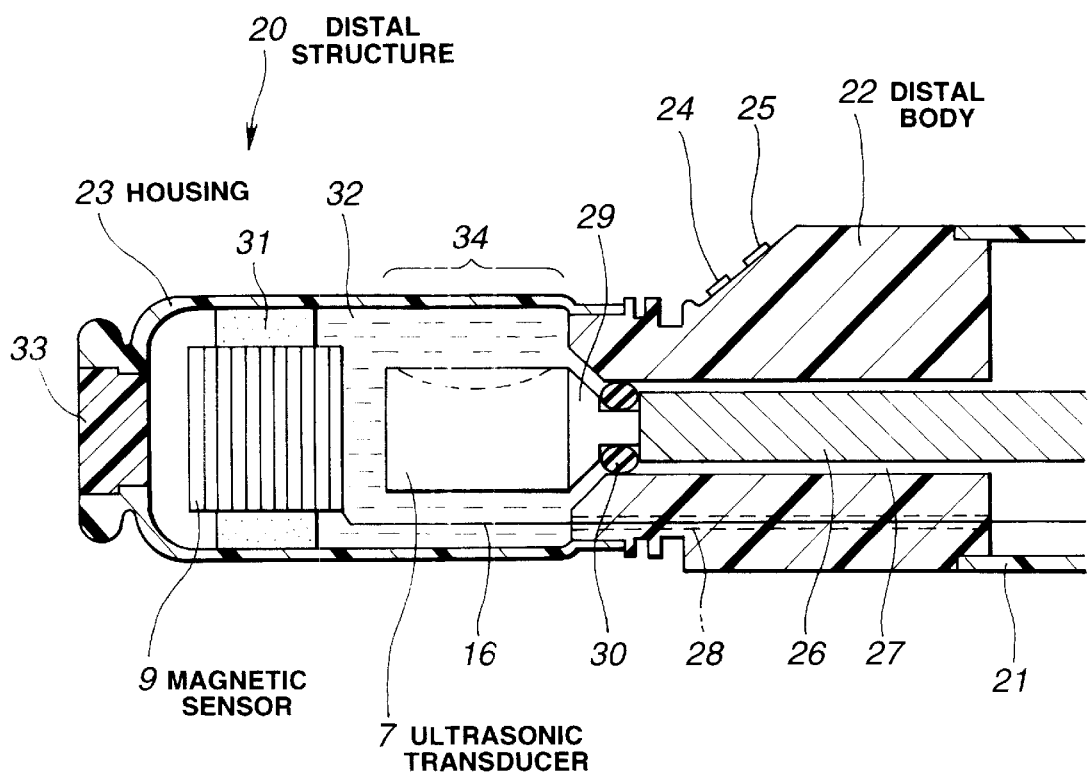

FIG. 3 is a diagram showing a distal structure 20 of the ultrasonic endoscope 2. The distal part 20 consists of a distal body 22 attached to the distal end of a casing 21 outlining an insertion unit 6 and made of a non-conductive material, and a housing 23 made of a non-conductive material. An illumination window 24 and objective window 25 are juxtaposed on an inclined surface of the distal body 22, whereby the ultrasonic endoscope is regarded as an oblique-view type. The illumination window 24 is used to irradiate light, which emanates from a light source, to the interior of a body cavity over light guide fibers that are not shown. The objective window is used to receive an optical image. The optical image is converted into an electrical signal by an imaging unit that includes a solid-state imaging device that is not shown, and then displayed on the monitor by way of a video processing circuit. Instead of displaying an image, which is produced by the imaging unit and sent over the image guide fibers, on the monitor, an optical image may be viewed directly.

A passage hole 27 through which a flexible shaft 26 lies and a passage hole 28 through which the signal line 16 extending from the magnetic sensor 9 lies are defined in the distal body 22. The housing 23 communicating with the passage holes 27 and 28 is mounted on the distal end of the distal body 22 so that the housing 23 will be impermeable to any fluid. The flexible shaft 26 has a holder 29, which accommodates the ultrasonic transducer 7, attached to the distal end thereof. The signal line 14 extending from the ultrasonic transducer 7 is passed through the flexible shaft 26. The ultrasonic transducer 7 is placed in the housing 23. A seal member 30 for sealing the housing 23 is fitted on the proximal end of the holder 29. The proximal end of the flexible shaft 26, the end toward an operator's hand is rotated by a motor in an operation unit that is not shown. This causes the ultrasonic transducer 7 to oscillate radially for scanning. Consequently, an ultrasonic tomographic image depicting a plane orthogonal to the axis of rotation is produced.

A holding member 31 for holding the magnetic sensor 9 is located in front of the ultrasonic transducer 7 in the housing 23. The magnetic sensor 9 is realized with, for example, a coil having three orthogonal axes. The signal line 16 extending from the magnetic sensor 9 is placed in the housing 23 and in the insertion unit 6 through the passage hole 28. The passage hole 28 is provided with a seal member for sealing the housing 23, though the seal member is not illustrated. A lid 33 made of a non-conductive material and opened to accept an ultrasonic propagation fluid (for example, water) 32 is located at the distal end of the housing 23. The housing 23 is made of a material capable of transmitting ultrasonic waves, such as, a resin so that ultrasonic waves can be transmitted by an ultrasound transmitting portion 34.

All the members of the distal structure 20 of this embodiment other than the ultrasonic transducer 7, signal line 14, magnetic sensor 9, and signal line 16 are made of a non-conductive material. The non-conductive material is a plastic resin, ceramic, or the like.

Figure 4:
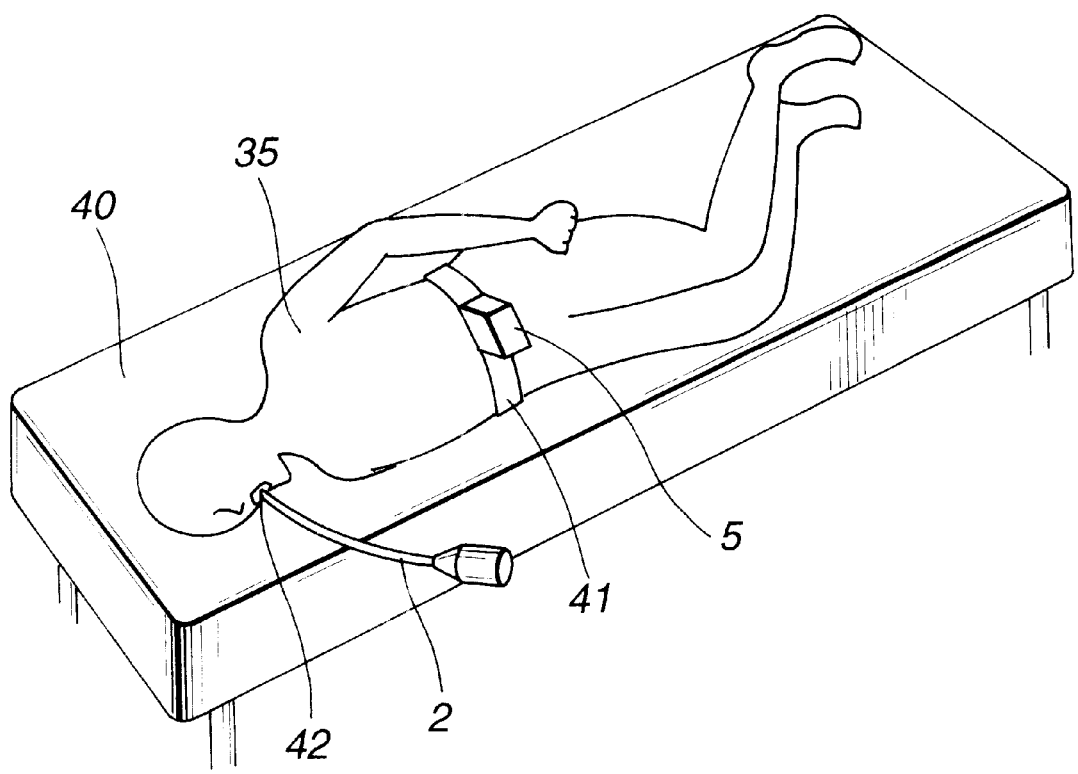
FIG. 4 is a diagram relating to the second embodiment of the present invention and showing a use state.

The operations of this embodiment will be described below, in connection with FIG. 4.

The insertion unit 6 of the ultrasonic endoscope 2 is inserted into a body cavity of a subject (human body) 35, for example, the stomach. The distal structure 20 is introduced to a desired region. Ultrasonic diagnosis is then carried out. The magnetic field transmitter 5 is driven to originate a reference signal to the distal structure 20. In the ultrasonic endoscope 2, the flexible shaft 26 is rotated by a motor that is not shown. This causes the ultrasonic transducer 7 to rotate. The insertion unit 6 is inched in an axial direction in order to carry out spiral scanning. Image data sent from the ultrasonic transducer 7 is input to the image detector 11 in the host processor 3 over the signal line 14, and stored as two-dimensional ultrasonic image data.

On the other hand, the magnetic sensor 9 detects a magnetic field induced by the magnetic field transmitter 5, and inputs a detection signal, which is a signal detected by the magnetic sensor, to the position detector 12 over the signal line 16. The image processor 13 concurrently acquires both two-dimensional ultrasonic image data sent from the image detector 11 and position data that indicates positions relevant to two-dimensional ultrasonic images and is sent from the position detector 12. The image processor 13 then constructs a three-dimensional ultrasonic image using the two-dimensional ultrasonic images, and displays the three-dimensional ultrasonic image on the monitor 4. Located near the magnetic sensor 9 are conductors alone such as the ultrasonic transducer 7 and the signal line 14 extending from the ultrasonic transducer, and the signal line 16 extending from the magnetic sensor 9. The other members of the distal structure 20 are made of a non-conductive material. Development of an eddy current is therefore minimized. The position data sent from the magnetic sensor 9 will therefore not be disordered but input to the position detector 12.

According to this embodiment, development of an eddy current in the distal structure 20 can be suppressed as much as possible. A measurement error in position data can be reduced, and a three-dimensional ultrasonic image with high precision can be produced. This results in the improved reliability of an examination or diagnosis.

The second embodiment of the present invention will be described below.

In this embodiment, not only the ultrasonic endoscope 2 but also its peripheral equipment or accessories are made of a non-conductive material.

To be more specific, an examination bed 40 for a subject (human body) 35, a housing of a magnetic field transmitter 5, a magnetic field transmitter locking belt 41 used to lock the magnetic field transmitter 5 on the subject 35, and a mouthpiece 42 used to introduce the ultrasonic endoscope 2 into the interior of the subject 35 are made of a non-conductive material.

Owing to this structure, no eddy current develops in the peripheral equipment due to a magnetic field induced by the magnetic field transmitter 5. This leads to the improved precision in detecting the position of the distal part of the ultrasonic endoscope.

The third embodiment of the present invention will be described below.

Figure 5:
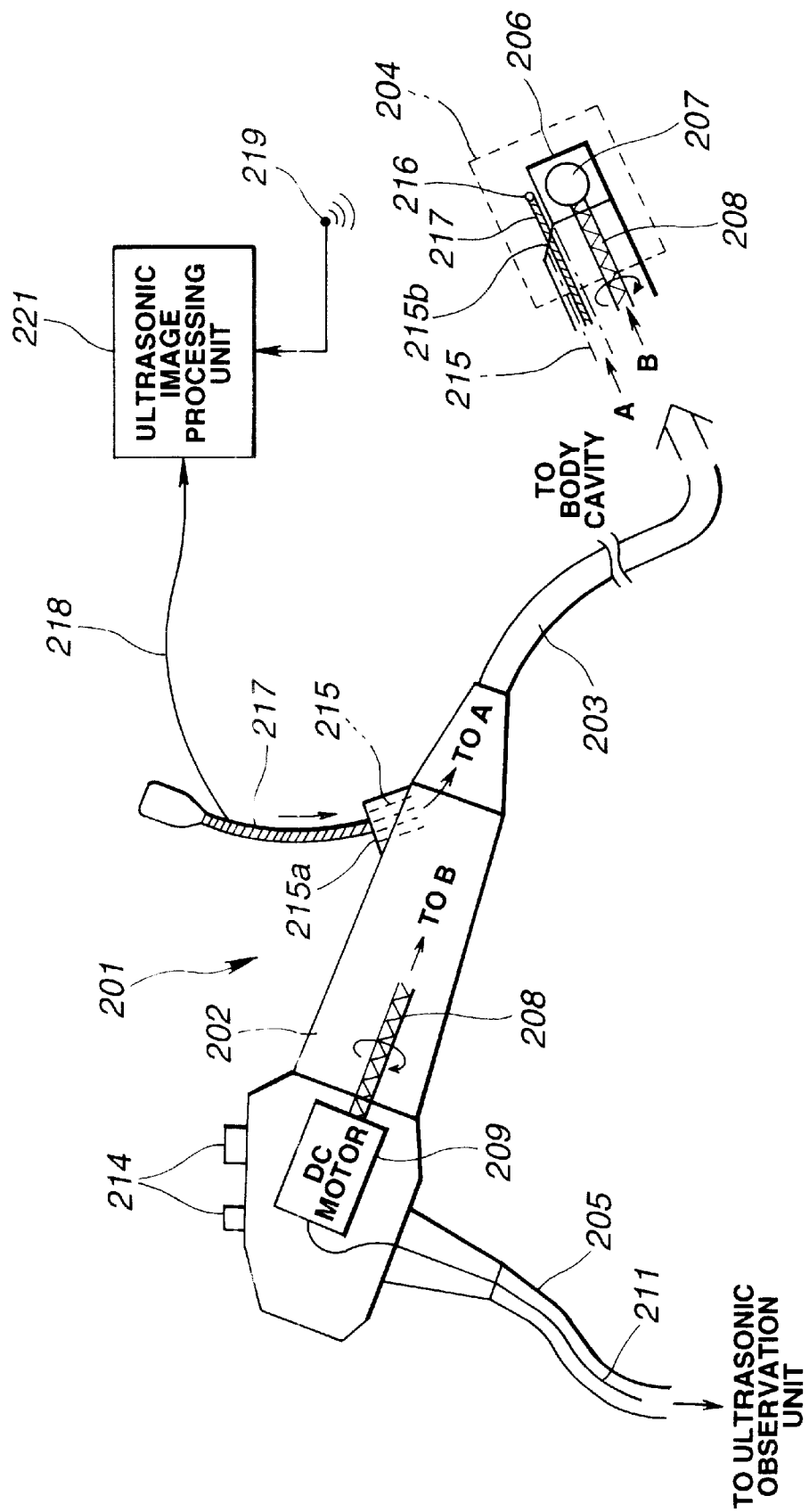
FIGS. 5 to 8 are diagrams relating to the third embodiment of the present invention.
Figure 6:
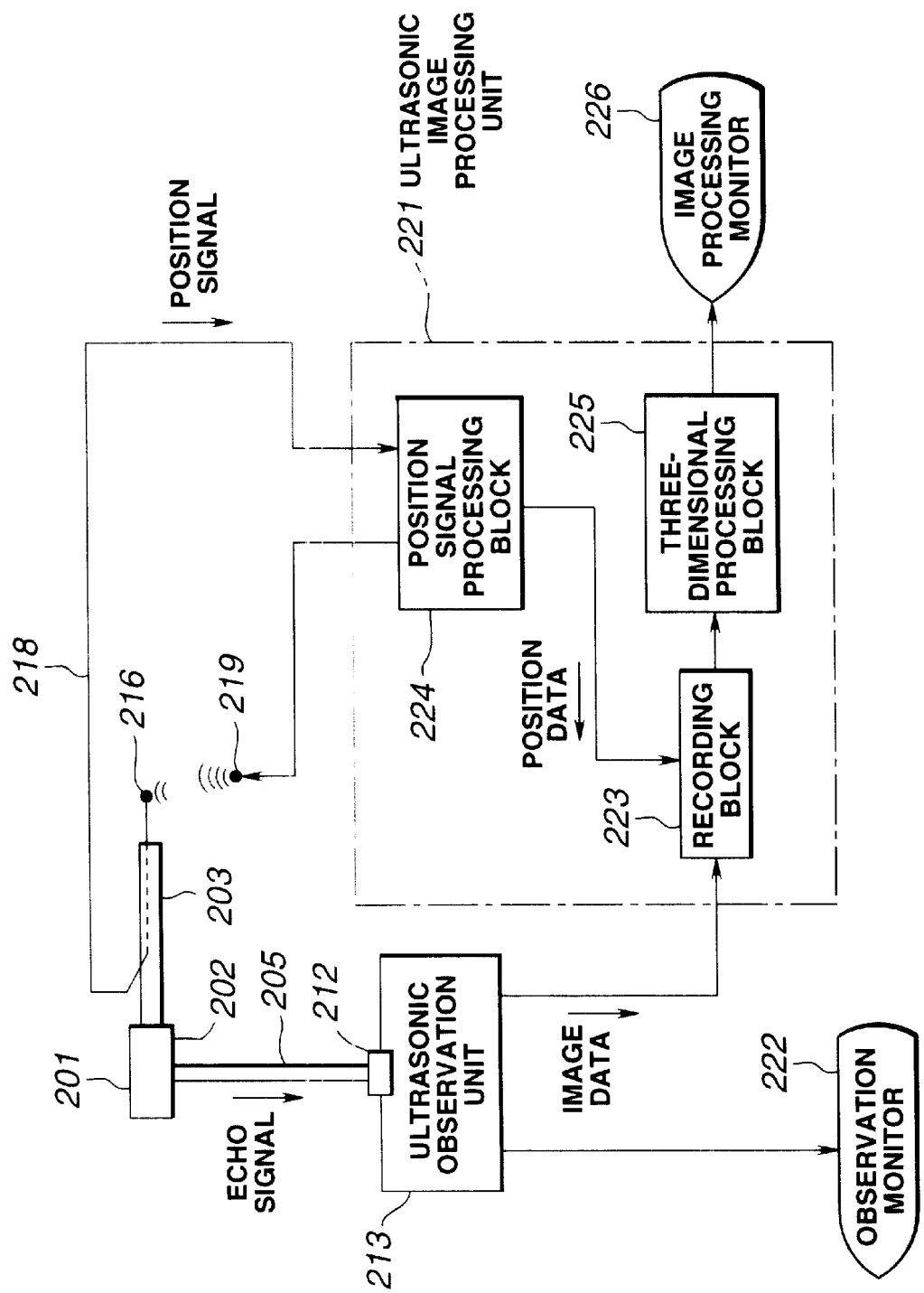

As shown in FIGS. 5 and 6, an ultrasonic endoscope 201 has an elongated insertion unit 203, which is to be inserted into a body cavity, extended from an operation unit 202 located proximally. An ultrasonic cable 205 extends from the lateral side of the operation unit 202.

The operation unit 202 has a plurality of operation buttons 214 formed on the lateral side of the proximal part thereof, and has a forceps port 215a protruding from the lateral side of the distal part thereof. In the operation unit 202, a DC motor 209 and a flexible shaft 208 whose one end is coupled to the axis of rotation of the DC motor 209 are incorporated.

A signal line 211 coupled to the DC motor 209 is included in the ultrasonic cable 205.

Moreover, a forceps channel 215 serving as a passage that communicates with the forceps port 215a is defined in the insertion unit 203. The other end of the forceps channel communicates with a protruding port 215b formed in a distal rigid part 204 of the insertion unit 203.

The distal rigid part 204 of the insertion unit 203 has a cap 206 at the distal end thereof. An ultrasonic transducer 207 is included in the cap 206.

The ultrasonic transducer 207 is attached to the other end of the flexible shaft 208, and driven by the DC motor 209. An echo signal sent from the ultrasonic transducer 207 is input to an ultrasonic observation unit 213 by way of the flexible shaft 208, the DC motor 209, the signal line 211 in the ultrasonic cable 205, and a signal line, which is not shown, in an ultrasound connector 212.

A position detection catheter 217 has a magnetic sensor 216 at the distal end thereof. The position detection catheter 217 is inserted into the forceps channel 215 in the ultrasonic endoscope 201 through the forceps port 215 that is an entrance of the forceps channel. The position detection catheter 217 is jutted out of the protruding port 215b that is an exit of the forceps channel.

A position signal representing a position detected by the magnetic sensor 216 is input to an ultrasonic image processing unit 221 over a position signal cable 218 in the position detection catheter.

The distal rigid part 204 located near the magnetic sensor 216, that is, the cap 206, the periphery of the protruding port 215b of the forceps channel 215, and the distal part of the flexible shaft 208 are made of a non-magnetic material, for example, titanium. This is intended not to disorder a magnetic field around the magnetic sensor 216.

Moreover, a magnetic field source 219 is located at a position outside the ultrasonic endoscope 201 and subject. The magnetic field source 219 is connected to the ultrasonic image processing unit 221.

Image data of an ultrasonic tomographic image sent from the ultrasonic observation unit 213 is displayed on an observation monitor 222 in real time. The image data is also input to a recording block 223 included in the ultrasonic image processing unit 221, and thus recorded.

The magnetic sensor 216 and magnetic field source 219 are connected to a position signal processing block 224 included in the ultrasonic image processing unit 221. Position data computed by the position signal processing block 224 is input to the recording block 223 and recorded together with the image data.

An output of the recording block 223 is input to a three-dimensional processing block 225 and subjected to given processing. Thereafter, an image represented by the output signal is displayed on an image processing monitor 226.

Next, the operations of the ultrasonic diagnosis system of this embodiment will be described below.

For ultrasonic observation, the ultrasonic endoscope 201 is inserted into a body cavity of a subject, and the DC motor 209 is rotated. This causes the ultrasonic transducer 207 attached to the distal part of the flexible shaft 208 to rotate.

Consequently, the ultrasonic transducer 207 transmits ultrasonic waves radially in directions (radial directions) perpendicular to the axial direction of the distal rigid part 204 (direction in which the distal rigid part is inserted). The ultrasonic transducer 207 receives reflected ultrasonic waves (echoes) reflected from a portion of the subject whose acoustic impedance has changed.

The echoes stemming from radial scanning are input to the ultrasonic observation unit 213, and synthesized with image data representing an ultrasonic tomographic image. The image is then displayed on the observation monitor 222 in real time.

The image data is input to the recording block 223 and recorded. In other words, when the ultrasonic transducer 207 makes a turn to perform radial scanning, image data of one ultrasonic tomographic image output from the ultrasonic observation unit 213 is recorded in the recording block 223.

On the other hand, the magnetic field source 219 produces a magnetic field in the peripheral space. The magnetic sensor 216 senses the magnetic field, and outputs a voltage proportional to the magnetic fields as a position signal to the position signal processing block 224.

The position signal processing block 224 computes a position and inclination of the magnetic sensor 216 relative to the magnetic field source 219 in real time using the received position signal. The position and inclination is provided as position data (X, Y, Z; ψ, φ, θ) relative to the magnetic field source 219 serving as an origin.

The position data is input to the recording block 223. When image data of one ultrasonic tomographic image is input from the ultrasonic observation unit 213, the position data is recorded synchronously.

By repeating the foregoing operations, image data of a plurality of consecutive ultrasonic tomographic images stemming from radial scanning performed by the ultrasonic transducer 207 is recorded in the recording block 223 together with associated position data sent from the magnetic sensor 216.

Figure 7:
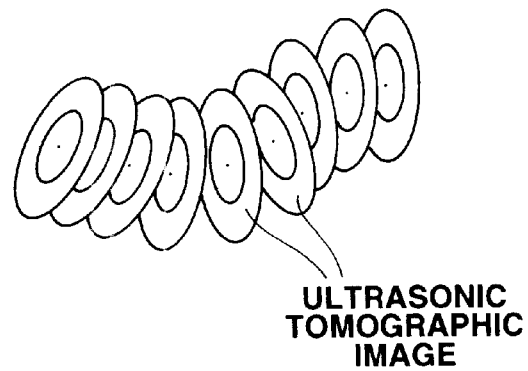

Specifically, a user inches the distal part of the ultrasonic endoscope 201 with the ultrasonic transducer 207 oscillated for radial scanning. Eventually, image data of a plurality of consecutive ultrasonic tomographic images like those shown in FIG. 7 is recorded in the recording block 223 together with associated position data.

Owing to the aforesaid configuration, when the distal rigid part 204 of the ultrasonic endoscope 201 moves, the magnetic sensor 216 moves by the same distance in the same direction as the distal rigid part 204. Position data produced by the magnetic sensor 216 can therefore be treated as data relevant to positions and inclinations of the plurality of ultrasonic tomographic images.

Thereafter, the three-dimensional processing block 225 receives the image data of the plurality of ultrasonic tomographic images from the recording block 223. The three-dimensional processing block 225 averages image data of superposed ultrasonic tomographic images or interpolates image data of adjoining ultrasonic tomographic images. Three-dimensional data of coordinates (X, Y, Z) relative to a certain point serving as an origin is thus structured.

Figure 8:
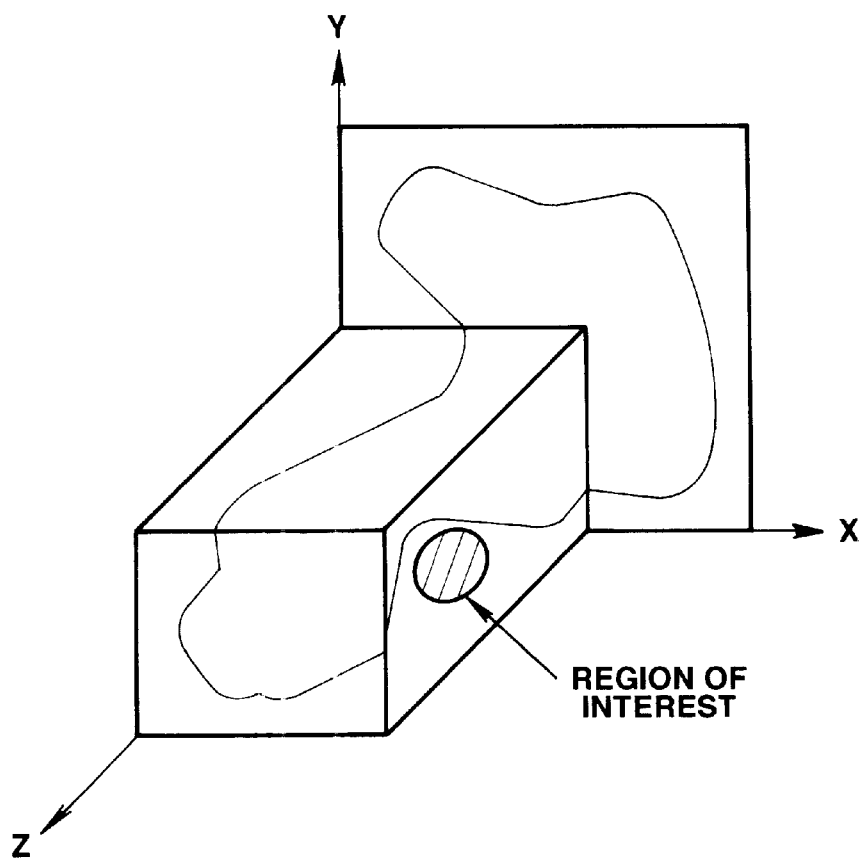

The three-dimensional processing block 225 constructs a three-dimensional image like the one shown in FIG. 8 using the three-dimensional data according to a known method such as section setting, and outputs the image to the image processing monitor 226. The image processing monitor 226 displays the three-dimensional image.

As illustrated, the three-dimensional image explicitly depicts the system of coordinates (X, Y, Z). The origin is set at a deep end as an intersection among the coordinate axes. The spatial position of a region of interest can therefore be grasped easily.

As mentioned above, in this embodiment, the forceps channel 215 serves as a passage. The magnetic sensor 216 functions as a position detecting means, and the ultrasonic image processing unit 221 including the three-dimensional processing block 225 functions as a three-dimensional processing means.

According to this embodiment, the ultrasonic endoscope scans a subject by oscillating and rotating the ultrasonic transducer, and produces an ultrasonic tomographic image. The position detection catheter lying through the forceps channel uses the magnetic sensor to output a position signal. The ultrasonic image processing unit synchronously acquires a position signal sent from the magnetic sensor and a plurality of consecutive ultrasonic tomographic images sent from the ultrasonic endoscope, and then structures three-dimensional data. Thus, ultrasonic tomographic images of high image quality can be acquired in order to structure three-dimensional data.

Moreover, three-dimensional data can be structured using a general-purpose ultrasonic endoscope without the need of a special drive or a special ultrasonic probe.

Furthermore, when the ultrasonic endoscope is used for a purpose other than the purpose of structuring three-dimensional data, the position detection catheter can be removed from the forceps channel. An examination can therefore be conducted with good maneuverability.

After a three-dimensional image is viewed, the position detection catheter can be removed from the forceps channel. Forceps or the like can then be inserted in order to carry out various kinds of treatments such as biopsy. For this purpose, three-dimensional data can be structured in the course of a routine examination.

Moreover, in the system described in the Japanese Unexamined Patent Publication No. 6-30937, a distortion deriving from a hand tremor, pulsation, a respiratory motion, or any other body motion appears in a three-dimensional image. According to this embodiment, such a distortion can be corrected.

Moreover, since the distal rigid part is made of a non-magnetic material such as titanium, a magnetic field around the magnetic sensor will not be disordered. This means that a position can be detected accurately.

Figure 9:
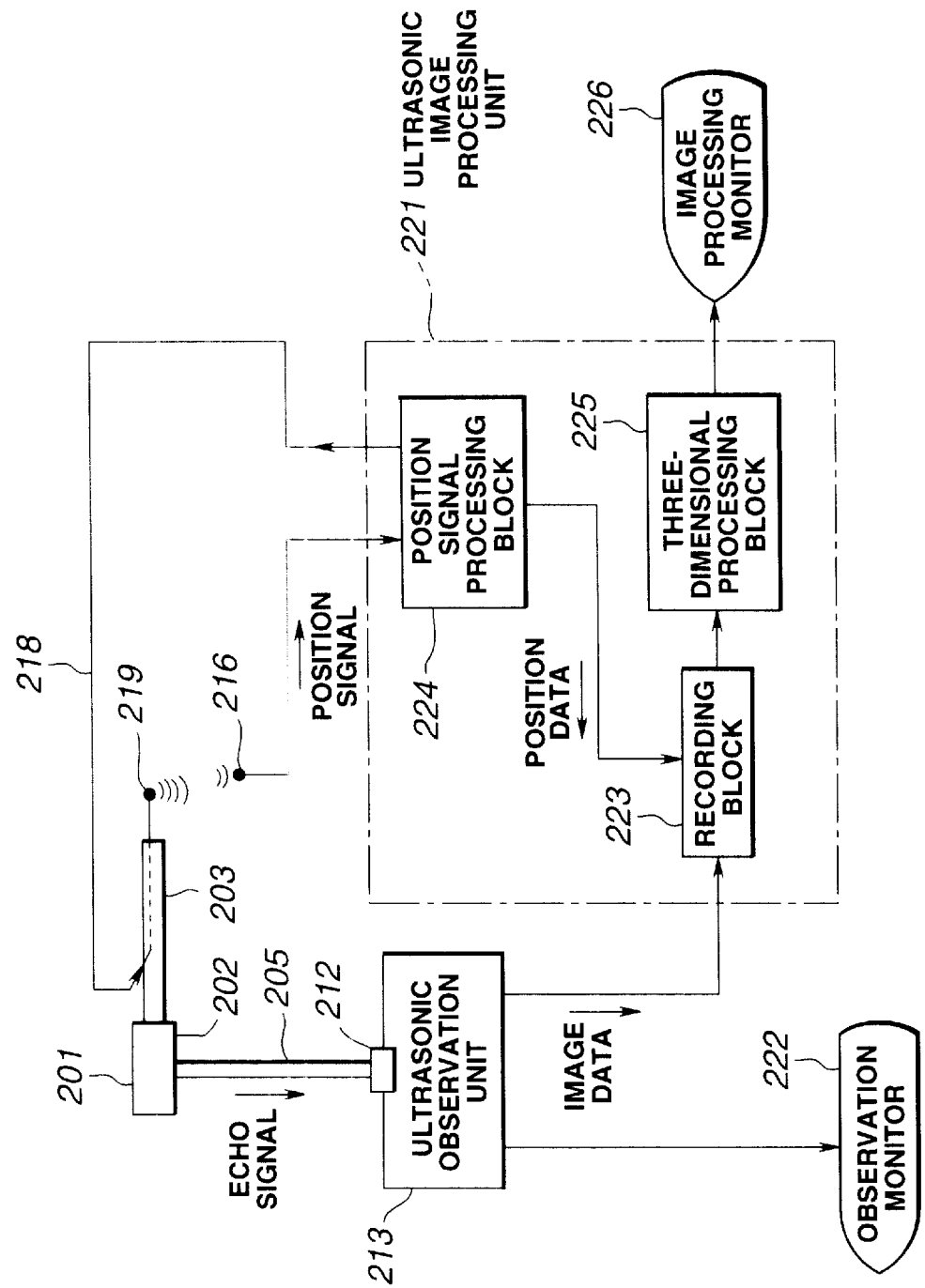
FIG. 9 is a block diagram relating to the fourth embodiment of the present invention and showing the configuration of an ultrasonic diagnosis system.

The fourth embodiment of the present invention will be described below with reference to FIG. 9.

In this embodiment, the description of components identical to those of the third embodiment will be omitted, and differences will be highlighted.

In this embodiment, the spatial positions of the magnetic sensor 216 and magnetic field source 219 of the third embodiment are switched. Specifically, the magnetic field source 219 is attached to the distal part of the position detection catheter 217 (See FIG. 5), and the magnetic sensor 216 is installed externally. The other components are identical to those of the third embodiment.

Next, the operations of this embodiment will be described below.

The position signal processing block 224 computes position data of the magnetic field source 219 in real time using a position signal output from the magnetic sensor 216.

In the third embodiment, the position signal processing block 224 computes a position and inclination of the magnetic sensor 216 relative to the magnetic field source 219 according to a position signal. The position signal processing block 224 then provides position data (X, Y, Z; $\psi$, $\Phi$, $\theta$) relative to the magnetic field source 219 serving as an origin.

By contrast, in this embodiment, since the relative positional relationship between the magnetic sensor 216 and magnetic field source 219 is reversed, position data of the magnetic field source 219 relative to the magnetic sensor 216 is computed in the same manner. The other operations are identical to those of the third embodiment.

As mentioned above, in this embodiment, the magnetic field source 219 functions as a position detecting means.

According to this embodiment, almost the same advantages as those of the third embodiment are provided.

Figure 10:
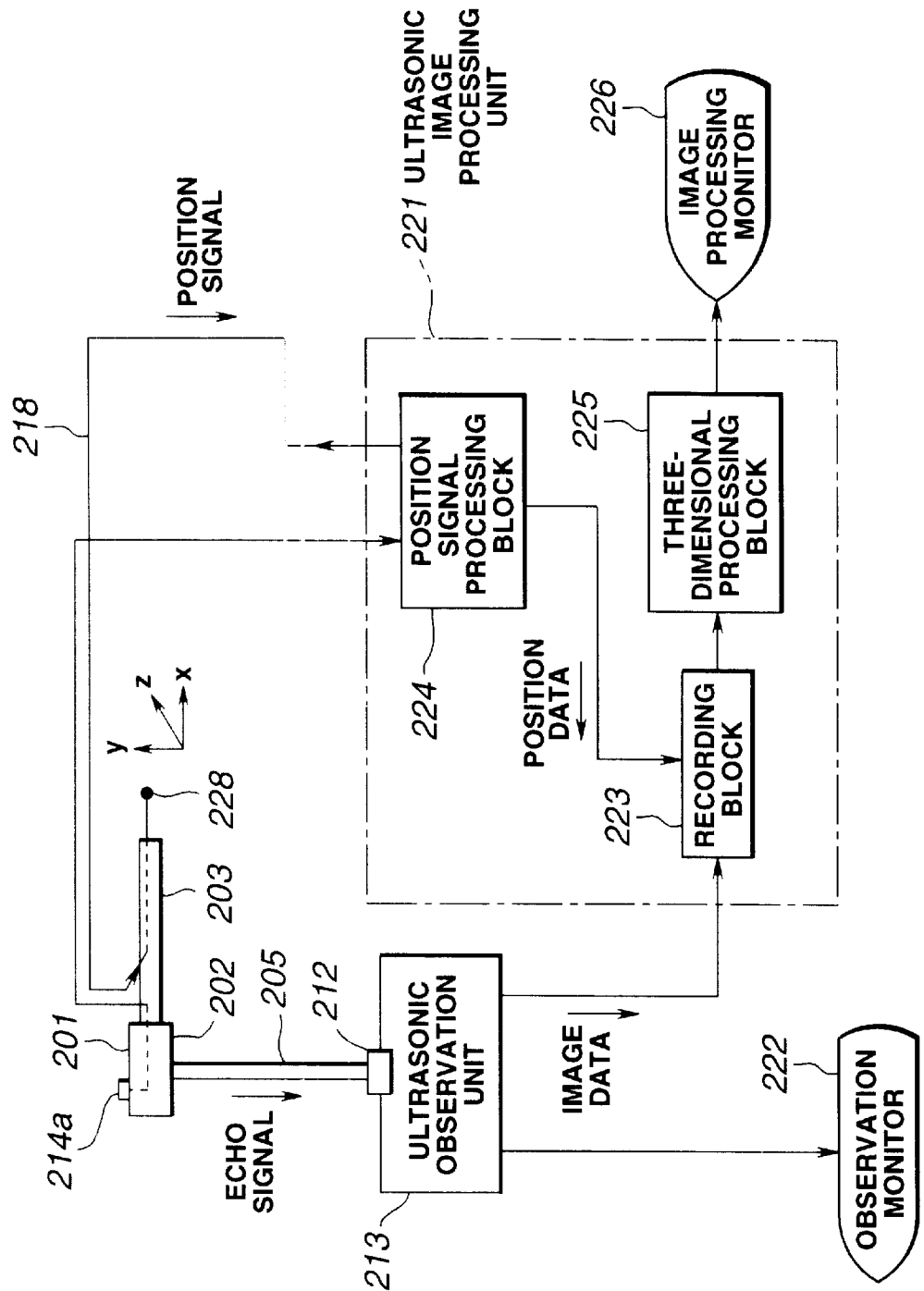
FIG. 10 is a block diagram relating to the fifth embodiment of the present invention and showing the configuration of an ultrasonic diagnosis system.

The fifth embodiment of the present invention will be described below with reference to FIG. 10.

In this embodiment, the description of components identical to those of the third and fourth embodiments will be omitted with a difference being highlighted.

This embodiment has an acceleration sensor 228 attached to the distal part of the position detection catheter 217 in place of the aforesaid magnetic sensor 216 and magnetic field source 219 of the third embodiment.

Moreover, the ultrasonic endoscope 201 has a position signal processing start button 214a at almost the same position as the operation buttons 214 shown in FIG. 5. The position signal processing start button 214a is connected to the position signal processing block 224 over a control line. The other components are identical to those of the third embodiment.

Next, the operations of this embodiment will be described below.

The position signal processing block 224 starts operating in response to an input sent from the position signal processing start button 214a over the control line.

The acceleration sensor 228 detects accelerations applied in the X direction, Y direction, and Z direction respectively, and outputs voltages proportional to the accelerations as position signals to the position signal processing block 224.

The position signal processing block 224 integrates components of the position signals relevant to the X direction, Y direction, and Z direction respectively, which are sampled for a certain time, and thus calculates the speed of the acceleration sensor 228. Incidentally, an integration constant employed is 0. Values of the speed which are sampled for a certain time are integrated in order to calculate coordinates (X, Y, Z) of the acceleration sensor 228 as position data. An integration constant employed this time is also 0.

The integration constants are 0. This means that the acceleration sensor 228 stands still at the origin at a time instant 0. In this case, therefore, position data computed by the position signal processing block 224 is equivalent to a magnitude by which the distal part of the ultrasonic endoscope 201 is displaced from the position of the origin at which the distal part thereof stands still at the time instant 0.

For structuring three-dimensional data, the relative positional relationship among a plurality of consecutive ultrasonic tomographic images should merely be clarified. The time instant 0 and origin can therefore be set arbitrarily.

In practice, a user brings the distal part of the ultrasonic endoscope 201 to a standstill and presses the position signal processing start button 214a. This causes the position signal processing block 224 to start operating. Position data to be selected corresponds to coordinates relative to an origin that is a point (standstill point of the acceleration sensor 228) at which the acceleration sensor 228 lies at a time instant 0 (standstill time instant of the acceleration sensor 228).

Moreover, a processing sequence is carried out in real time by the position signal processing block 224. The other operations are identical to those of the third embodiment.

In this embodiment, the acceleration sensor 228 functions as a position detecting means.

According to this embodiment, since the acceleration sensor is employed, almost the same advantages as those of the third and fourth embodiments can be exerted.

Figure 11:
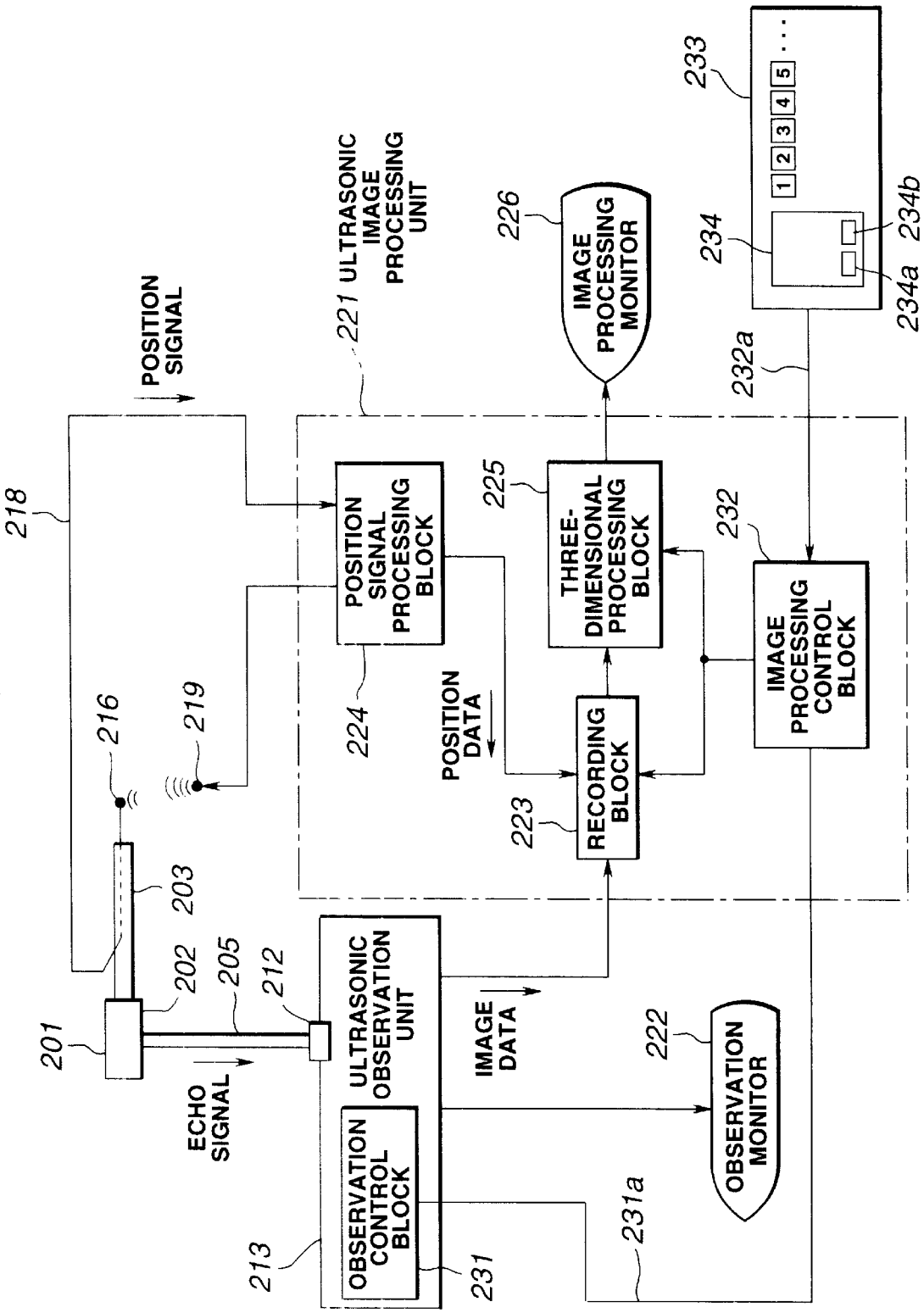
FIG. 11 shows the configuration of an ultrasonic diagnosis system.

The sixth embodiment of the present invention will be described below with reference to FIG. 11.

In this embodiment, the description of components identical to those of the third to fifth embodiments will be omitted. Different points alone will be described below.

An ultrasonic diagnosis system of this embodiment has, aside from the same components as those of the third embodiment, a keyboard 233 with a liquid crystal touch panel 234 whose display menu is variable.

Moreover, the ultrasonic observation unit 213 is provided with an observation control block 231 for controlling components in response to an input entered at the keyboard 233.

On the other hand, the ultrasonic image processing unit 221 is provided with an image processing control block 232 for controlling components including the recording block 223 and three-dimensional processing block 225 in response to an input entered at the keyboard 233.

A control line 231a extending from the observation control block 231 is coupled to the image processing control block 232. A control line 232a extending from the image processing control block 232 is coupled to the keyboard 233.

These control lines 231a and 232a are used not only to communicate a control instruction but also to communicate a 2-bit sense code indicating a powered state listed in Table 1.

The other components are nearly identical to those of the third embodiment.

TABLE 1

| Ultrasound observation unit | Ultrasonic image processing unit | |
|---|---|---|
| | On stage | Off stage |
| On stage | 11 | 01 |
| Off stage | 10 | 00 |

Next, the operations of this embodiment will be described below.

When the ultrasonic observation unit 213 is powered and switched on, the observation control block 231 of the ultrasonic observation unit 213 outputs a sense code "01" to the image processing control block 232 in the ultrasonic image processing unit 221 over the control line 231a.

Moreover, when the ultrasonic observation unit 213 is switched off, the observation control block 231 outputs a sense code "00."

In other words, one low-order bit of the sense code is used to sense the powered state of the ultrasonic observation unit 213. "1" represents an on state, while "0" represents an off state.

One high-order bit of the sense code is used to sense the powered state of the ultrasonic image processing unit 221. When the ultrasonic image processing unit 221 is switched on, the image processing control block 232 of the ultrasonic image processing unit 221 adds "10" to the value of a sense code input from the observation control block 231 over the control line 231a. When the ultrasonic image processing unit 221 is switched off, the image processing control block 232 adds "00" to the value of the sense code. The sum is output to the keyboard 233 over the control line 232a.

Based on the thus provided sense code listed in Table 1, the powered states of the ultrasonic observation unit 213 and ultrasonic image processing unit 221 are recognized at the keyboard 233.

When the ultrasonic observation unit 213 is switched on and the ultrasonic image processing unit 221 is switched off, the sense code is "01." In this case, the liquid crystal touch panel 234 of the keyboard 233 displays only menus necessary to control the ultrasonic observation unit 213.

The menus include, for example, a gain menu for adjusting an amplification ratio of an echo signal, a contrast menu, an STC (sensitivity time control) menu, a freeze menu for controlling the oscillations and rotation of the ultrasonic transducer 207 for radial scanning, and a freeze release menu.

When, for example, the freeze menu is selected from among the menus, a given instruction is output as a code from the keyboard 233.

The code is sent to the observation control block 231 via the image processing control block 232 over the control lines 232a and 231a. The observation control block 231 halts the DC motor 209 over the signal line 211 in the ultrasonic cable 205. Consequently, radial scanning is stopped.

When radial scanning must be carried out again, the freeze release menu should be selected from among the menus displayed on the liquid crystal touch panel 234. At this time, the image processing control block 232 does not give control.

On the other hand, when the ultrasonic observation unit 213 is switched off and the ultrasonic image processing unit 221 is switched on, the sense code is "10." In this case, the liquid crystal touch panel 234 displays only menus necessary to control the ultrasonic image processing unit 221.

Figure 12:
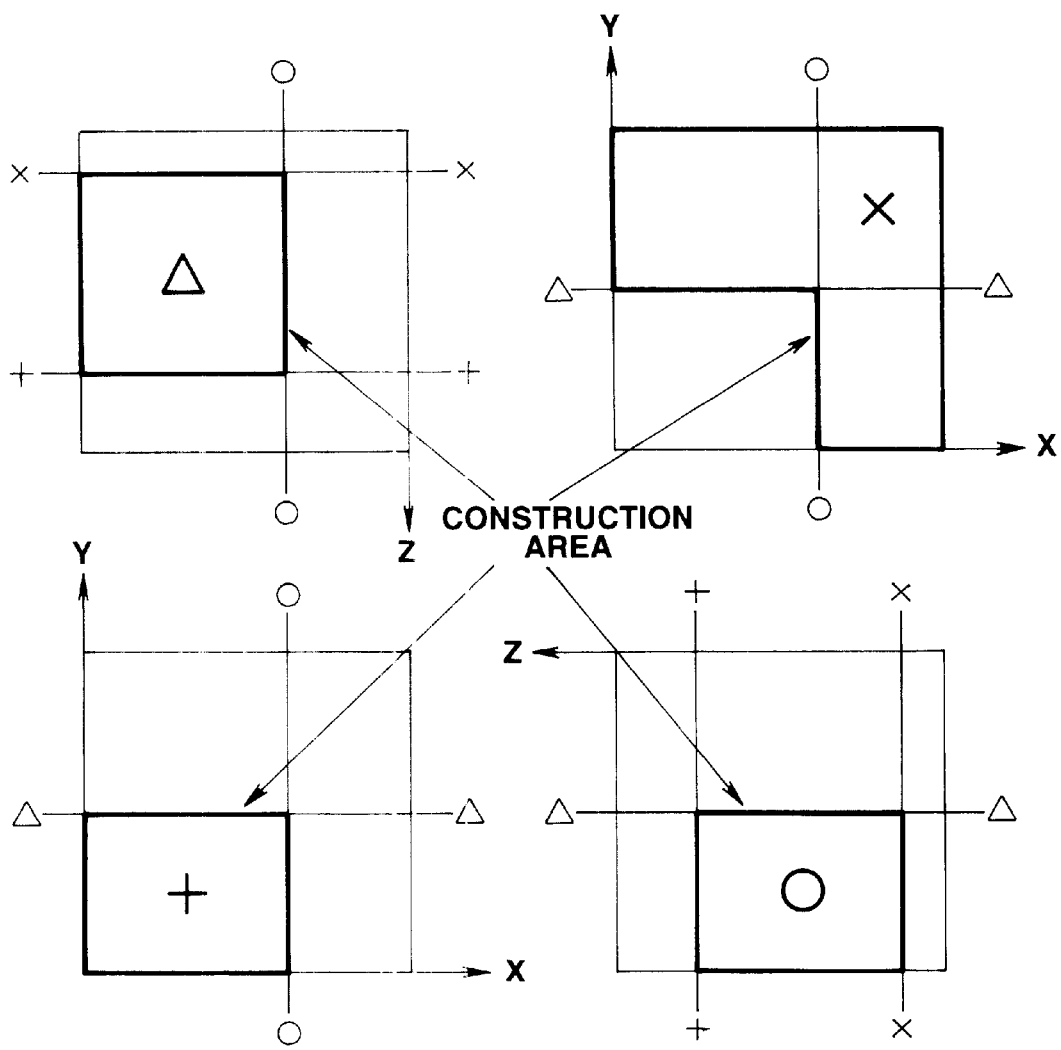
FIG. 12 is a diagram showing an example of an image displayed on an image processing monitor when a section display menu is selected.

The menus include, for example, menus associated with facilities that are necessary to structure three-dimensional data using image data and position data, which are recorded in the recording block 223, and to display an image represented by the three-dimensional data in any of various forms shown in FIG. 8 or 12 on the image processing monitor 226. Specifically, for example, a "section display menu" 234a and "stereoscopic display menu" 234b shown in FIG. 11 are displayed.

An example of operations of the three-dimensional processing block 225 that are provided when the menus are selected will be described below.

To begin with, a description will proceed on the assumption that, for example, the "section display menu" 234a is selected on the liquid crystal touch panel 234.

In this case, the three-dimensional processing block 225 cuts three-dimensional data with mutually orthogonal cutting-plane lines ○, Δ, x, and +, and displays resultant images on the image processing monitor 226 as shown in FIG. 12.

Figure 13:
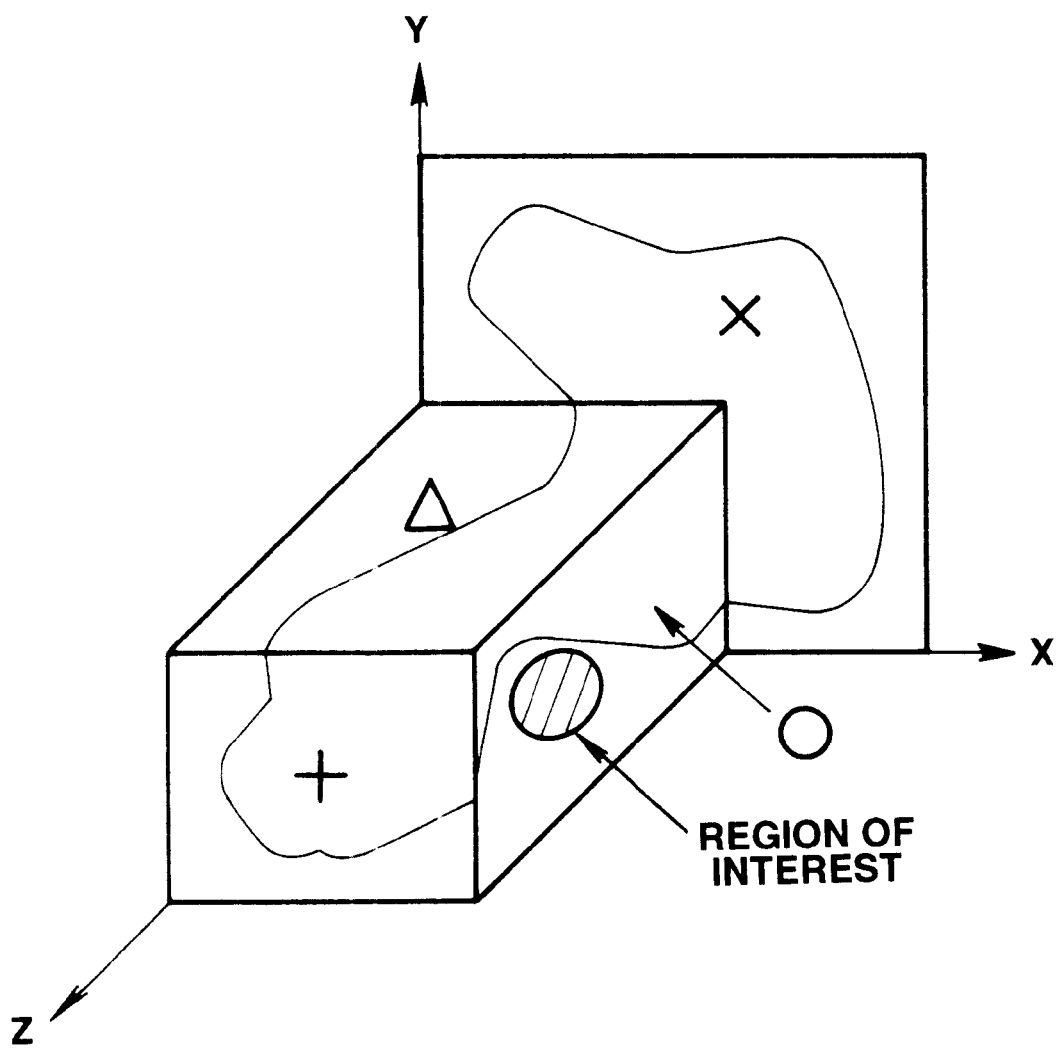
FIG. 13 is a diagram showing an example of an image displayed on the image processing monitor when a stereoscopic display menu is selected.

The relationship between the images shown in FIG. 12 and the three-dimensional image shown in FIG. 8, which has been described in conjunction with the third embodiment, is shown in FIG. 13.

In FIG. 12, sectional images (ranges defined with bold lines) defined with the cutting-plane lines ○, Δ, x, and + bear the same symbols ○, Δ, x, and +. FIG. 13 shows these sectional images ○, Δ, x, and + shown in FIG. 12 three-dimensionally.

Specifically, the sectional images x and + depict sections parallel to the XY plane, that is, mutually parallel sections. The sectional image ○ depicts a section parallel to the YZ plane, and the sectional image Δ depicts a section parallel to the ZX plane. These sectional images ○ and Δ are perpendicular to the sectional images x and +, and mutually perpendicular.

Thus, the cutting-plane lines ○, Δ, x, and + indicate the locations of the sectional images ○, Δ, x, and +.

Image data indicating a gray-scale level exhibited by an echo signal is displayed as each sectional image shown in FIG. 12. A menu for moving the cutting-plane lines ○, Δ, x, and + is displayed on the liquid crystal touch panel 234. Each sectional image is updated responsively to the movement.

Next, a description will proceed on the assumption that the "stereoscopic display menu" 234b is selected on the liquid crystal touch panel 234.

In this case, the three-dimensional processing block 225 displays a three-dimensional image like the one shown in FIG. 8 on the image processing monitor 226 according to the selected sectional images.

Finally, when the ultrasonic observation unit 213 is switched on and the ultrasonic image processing unit 221 is switched on, the sense code is "11." In this case, the liquid crystal touch panel 234 displays both the menus necessary to control the ultrasonic observation unit 213 and ultrasonic image processing unit 221.

The other operations are nearly identical to those of the third embodiment.

As mentioned above, a representation of three-dimensional data structured by the three-dimensional processing block 225 is not limited to the three-dimensional image shown in FIG. 8. Alternatively, the representation may be a plurality of sectional images like those shown in FIG. 12 bearing symbols (markers) that explicitly indicate a relative positional relationship.

As mentioned above, in this embodiment, the magnetic sensor 216 functions as a position detecting means, and the ultrasonic image processing unit 221 including the three-dimensional processing block 225 functions as an image processing means. Moreover, the liquid crystal touch panel 234 functions as a menu selecting means, and the keyboard 233 functions as an operator console.

In this embodiment, the keyboard 233 having the liquid crystal touch panel 234 is used as an operator console. However, the liquid crystal touch panel 234 may not be included. Moreover, the keyboard may be designed so that when the power supply is turned off, associated keys cannot be validated.

Moreover, in this embodiment, the liquid crystal touch panel 234 is used as a menu selecting means. Alternatively, any other device having no liquid crystal will do.

Figure 14A:
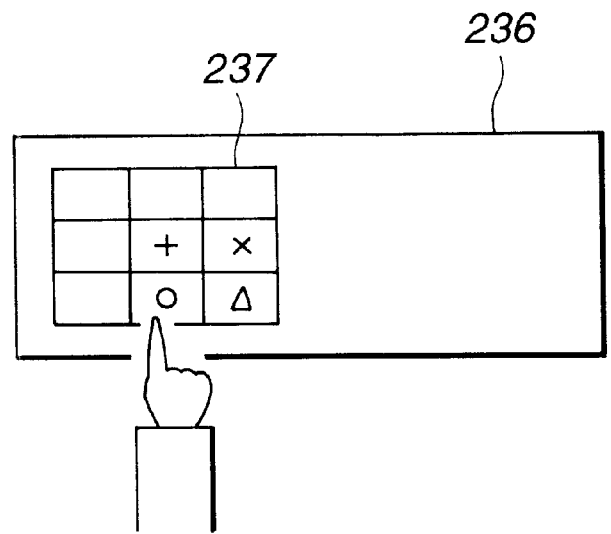
FIG. 14A is a diagram showing a state in which a keyboard having a keypad is handled.
Figure 14B:
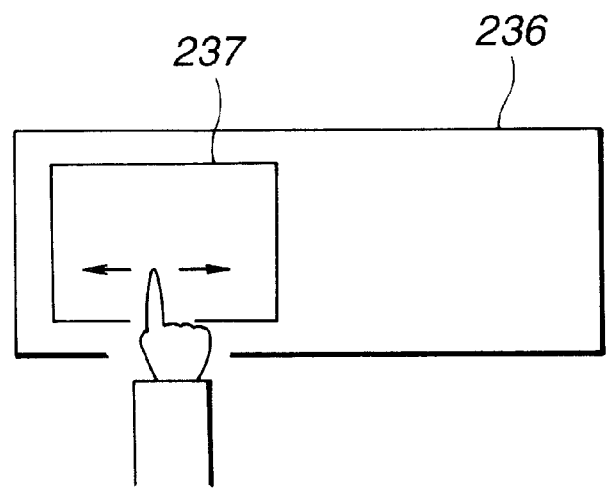
FIG. 14B is a diagram showing a state in which the keyboard having the keypad is handled.

FIGS. 14A and 14B show a variant of the sixth embodiment.

A keyboard 236 has a keypad 237. The keypad 237 is, as shown in FIG. 14A, trisected lengthwise and sideways, and thus divided into nine areas. Menus associated to facilities are allocated to the areas.

Assume that an area allocated to, for example, a cutting-plane line ○ out of the nine division areas is touched with a finger or the like. The keypad 237 then shifts to a mode (hereinafter, a trace mode) in which the cutting-plane line ○ shown in FIG. 12 can be moved.

A user moves his/her finger right and left as indicated with arrows in FIG. 14B. This causes the cutting-plane line ○ to move in right and left directions in FIG. 12 in which the finger is moved. Resultant images are displayed on the image processing monitor 226.

Moreover, when the keypad 237 shifts to the mode in which the cutting-plane line ○ shown in FIG. 12 can be moved, a message saying, for example, "The keypad enters the trace mode." is displayed on the image processing monitor 226.

Thus, the keypad 237 is designed to selectively play a role of selecting a facility and a role of moving a cutting-plane line or cursor on a screen according to a selected mode.

In this variant, the keypad 237 functions as a menu selecting means.

The sixth embodiment has been described that the ultrasonic observation unit 213 and ultrasonic image processing unit 221 are a plurality of stand-alone components. Alternatively, a unit for producing an image using echo data of ultrasonic tomographic images, and a unit for producing an image other than the image represented by echo data, such as, a radiographic image, an MR (magnetic resonance) image, or a video endoscopic image may be included as the stand-alone components.

According to the sixth embodiment, almost the same advantages as those of the third to fifth embodiment are provided. Besides, at the keyboard, any of a plurality of stand-alone units, that is, either of the ultrasonic observation unit and ultrasonic image processing unit whose power supply is turned on is sensed. Only a facility of the unit whose power supply is turned on is enabled to operate. Using one operator console, a plurality of stand-alone units can be controlled. This leads to improved maneuverability.

The seventh embodiment of the present invention will be described below with reference to FIG. 15.

In this embodiment, the description of components identical to those of the third to sixth embodiments will be omitted. Different points alone will be described mainly.

The ultrasonic endoscope 201 is provided with a RAM 241 that is connected by signal lines to a write control circuit 246 and read control circuit 247, which will be described later, included in the ultrasonic observation unit 213.

On the other hand, the ultrasonic observation unit 213 consists of: a pulser 242 for applying a pulsating voltage to oscillate the ultrasonic transducer 207 at the time of viewing an ultrasonic tomographic image; a switch 243 for changing a destination of an echo signal sent from the ultrasonic transducer 207 over to either a transducer sensitivity corrector 244 or amplifier 248; a transducer sensitivity corrector 244 for correcting the sensitivity of the ultrasonic transducer 207 for reception; a read control circuit 247 for reading data recorded in the RAM 241; an amplifier 248 for amplifying an echo signal sent from the ultrasonic transducer 207; an A/D converter 249 for converting an amplified echo signal into a digital signal; a digital scan converter (DSC in the drawing) 250 for transforming coordinates so that an image represented by the digital signal can be displayed on the observation monitor 222; and a D/A converter 252 for converting image data recorded in a frame memory 251, which stores image data resulting from coordinate transformation, into an analog signal so that an image represented by the analog signal can be displayed on the observation monitor 222.

Furthermore, the transducer sensitivity corrector 244 includes a reception voltage detection circuit 245, and a write control circuit 246 for recording data in the RAM 241. An output terminal of the switch 243 is connected to the reception voltage detection circuit 245.

Moreover, the frame memory 251 is connected to the observation monitor 222 and ultrasonic image processing unit 221.

The ultrasonic endoscope 201 and ultrasonic observation unit 213 are interconnected via an ultrasound connector 212 like the one shown in FIG. 6. The ultrasonic observation unit 213 may be connected to another ultrasonic endoscope.

Next, the operations of this embodiment will be described below.

To begin with, sensitivity data used to correct the sensitivity of the ultrasonic transducer 207 for reception is recorded. At this time, the switch 243 changes the destination of an echo signal over to the reception voltage detection circuit 245 in the transducer sensitivity corrector 244. The operations will be described.

The reception voltage detection circuit 245 applies a voltage serving as a reference to the ultrasonic transducer 207. A reception voltage whose level is proportional to the magnitude of echoes returned from a subject that is not shown is then converted into sensitivity data that is digital data, and output to the write control circuit 246. The write control circuit 246 records the sensitivity data in the RAM 41 in the ultrasonic endoscope 201.

Next, the operations of this embodiment that are provided when an ultrasonic tomographic image is viewed on the observation monitor 222 will be described below.

In this case, the switch 243 changes the destination of an echo signal over to the amplifier 248. On the other hand, the read control circuit 247 reads sensitivity data from the RAM 241, and determines a gain to be produced by the amplifier 248 according to the sensitivity data.

The amplifier 248 amplifies an echo signal according to the determined gain. Thereafter, the amplified echo signal is converted into a digital signal by the A/D converter 249. Coordinates represented by the digital signal are then transformed by the digital scan converter 250. A resultant signal is output as an ultrasonic tomographic image to the observation monitor 222 via the D/A converter 252.

As mentioned above, in this embodiment, the ultrasonic endoscope 201 functions as an ultrasonic probe, the amplifier 248 functions as a variable gain amplifier, and the ultrasonic observation unit 213 functions as an observing means. The read control circuit 247 functions as a gain control means, the RAM 241 functions as a gain setting means and memory means, and the transducer sensitivity corrector 244 including the write control circuit 246 functions as a writing means.

The other operations are identical to those of the third embodiment.

Figure 16:
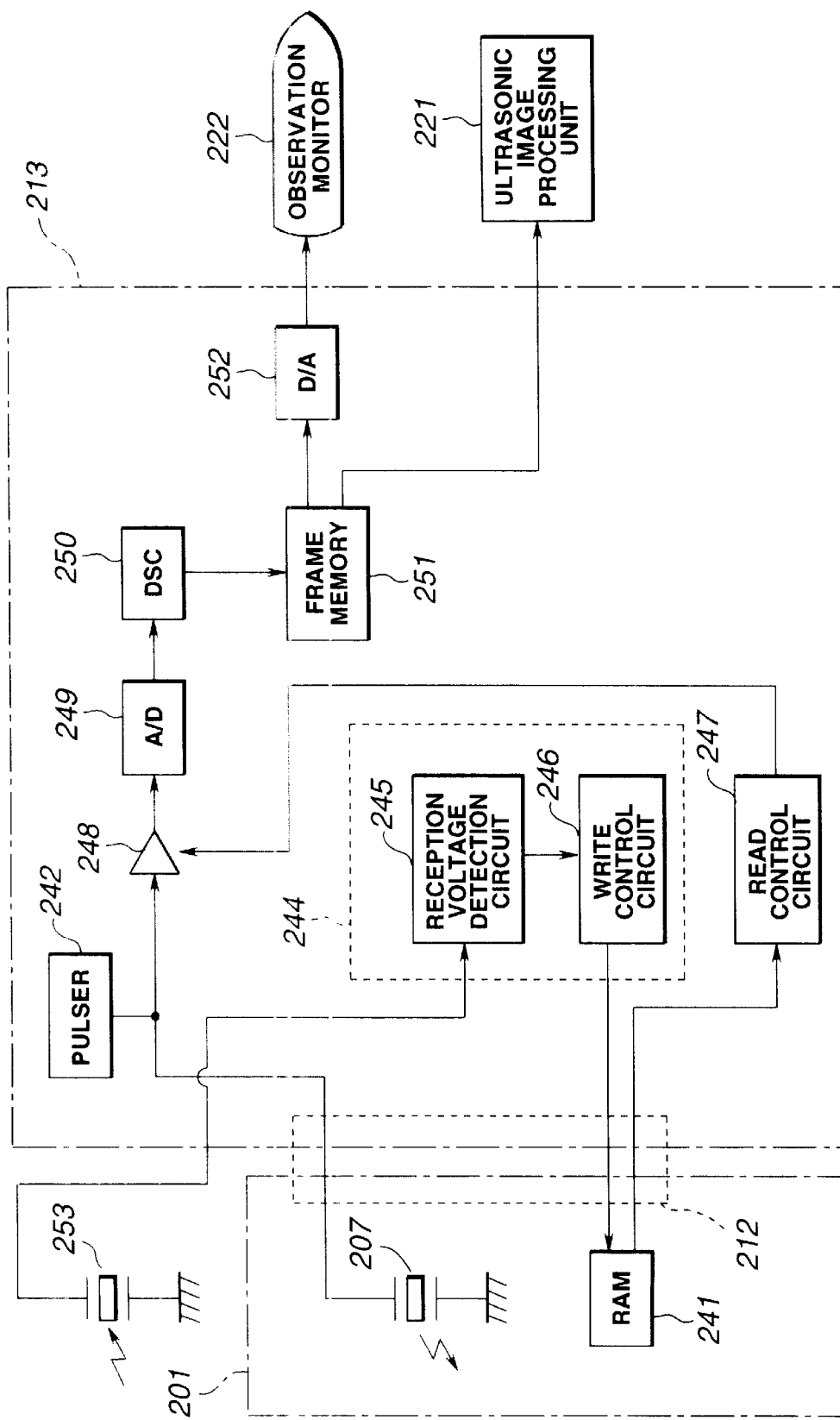

In this embodiment, a reception voltage whose level is proportional to the magnitude of echoes returned from a subject is converted into sensitivity data that is digital data. The present invention is not limited to this form. Alternatively, as shown in FIG. 16, for example, a hydrophone 253 may be installed externally. Electric waves output from the hydrophone may be received by the reception voltage detection circuit 245. In this case, the switch 243 becomes unnecessary.

For operating the ultrasonic diagnosis system, after the pulser 242 applies a voltage, which serves as a reference, to the ultrasonic transducer 207, a reception voltage sent from the hydrophone 253 is detected by the reception voltage detection circuit 245.

In this embodiment, the transducer sensitivity corrector 244 may be provided as an inspection jig separately from the ultrasonic observation unit 213. This configuration makes it easy to record sensitivity data in the RAM 241. Specifically, the inspection jig is used to record sensitivity data in the RAM 241 prior to delivery from the factory or during a periodic inspection after the delivery.

According to this embodiment, almost the same advantages as those of the third to sixth embodiments are provided. Besides, the ultrasonic endoscope is connected selectively to circuit elements of the ultrasonic observation unit connects. The write control circuit stores an acoustic characteristic of the ultrasonic transducer in the RAM. The read control circuit controls a gain to be produced by the amplifier according to the gain set in the RAM with the ultrasonic endoscope serving as an ultrasonic probe connected to the ultrasonic observation unit. Once the ultrasonic probe is connected to the observation unit, a variation in sensitivity of the ultrasonic transducer for reception including a time-passing change can be corrected.

The eighth embodiment of the present invention will be described below.

Figure 17:
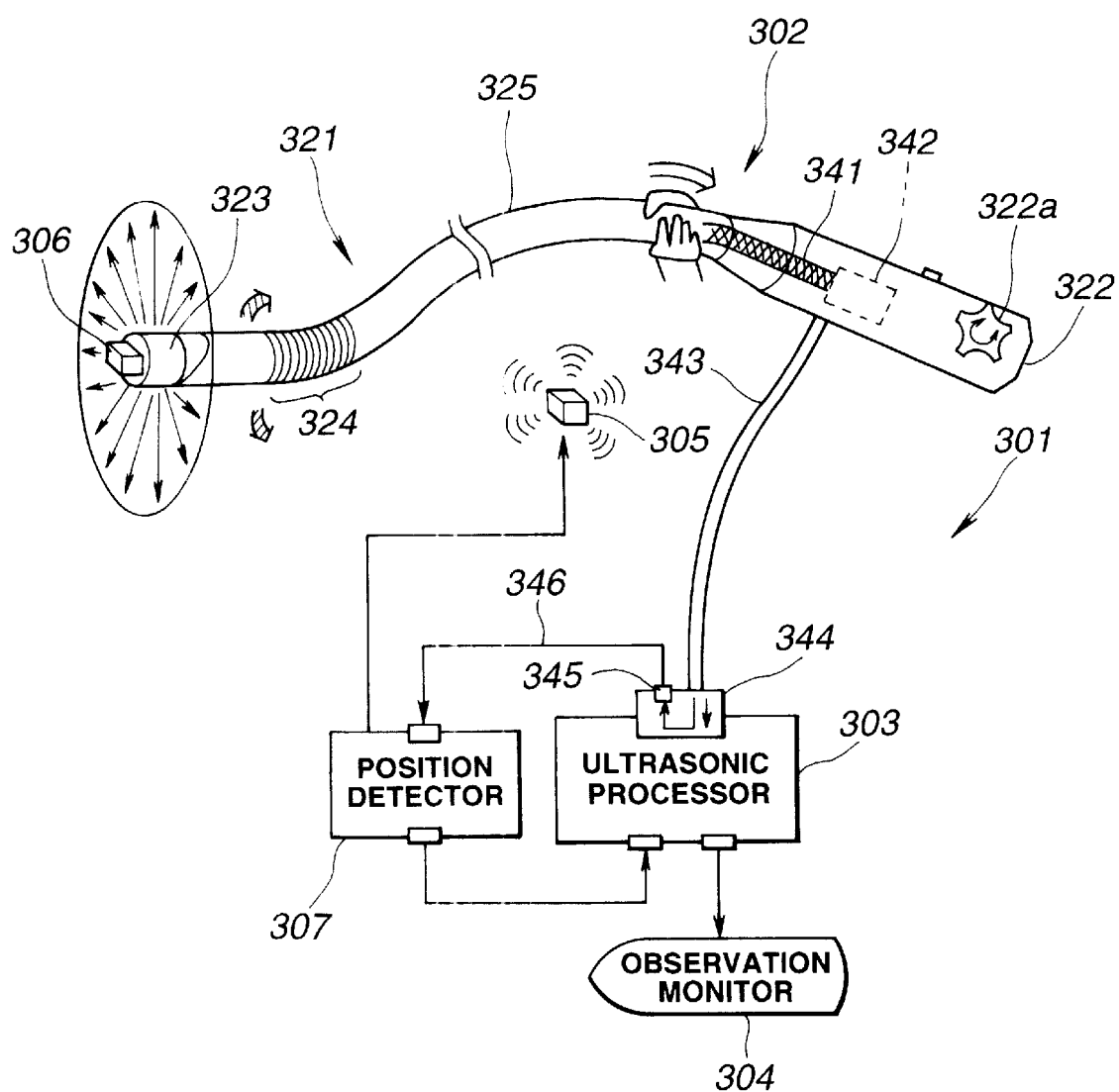
FIGS. 17 and 18 relate to the eighth embodiment of the present invention.

As shown in FIG. 17, an ultrasonic diagnosis system 301 consists of: an ultrasonic endoscope 302 serving as an ultrasonic probe of this embodiment for irradiating ultrasonic waves to an examined region in a body cavity and producing an echo signal; an ultrasound processor 303 for producing a three-dimensional ultrasonic tomographic image of the examined region according to the echo signal produced by the ultrasonic endoscope 302; an observation monitor 304 for displaying the three-dimensional ultrasonic image produced by the ultrasound processor 303; and a position detector 307 that uses a magnetic sensor 306 included in the distal part of the ultrasonic endoscope 302 to detect a magnetic field generated by a magnetic field source 305, and thus detects the position of the distal part of the ultrasonic endoscope 302.

The ultrasonic endoscope 302 consists of an elongated insertion unit 321 to be inserted into a body cavity, and an operation unit 322 coupled to the proximal end of the insertion unit 321. The insertion unit 321 has a distal cap 323, a bending portion 324, and a soft tube 325 having plasticity are provided in that order from the distal end thereof. The bending portion 324 can be angled by manipulating an angling knob 322a formed on the operation unit 322.

Figure 18:
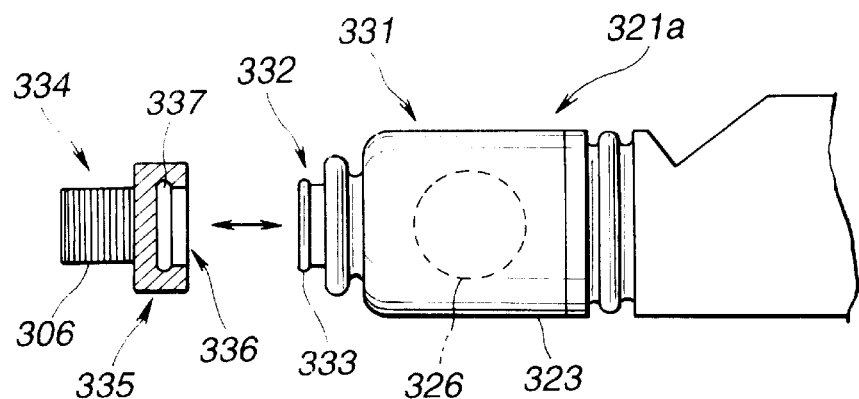

As shown in FIG. 18, an ultrasonic transducer 326 for transmitting or receiving ultrasonic waves in the outer circumferential directions of the distal cap 323 is incorporated in the distal cap 323 of the insertion unit 321. Moreover, the magnetic sensor 306 for detecting a magnetic field generated around the distal cap 323 by the magnetic field source 305 is attached to the distal end of the distal cap 323.

To be more specific, the distal part 321a of the insertion unit 321 has a scanner portion 331. The ultrasonic transducer 326 is incorporated in the scanner portion 331. The ultrasonic transducer 326 is enclosed in the distal cap 323. The interior of the distal cap 323 is filled with an ultrasound propagation medium that is not shown. An attachment 332 is formed at the distal end of the distal cap 323. The attachment 332 has a convex part 333 at the distal end thereof.

A position detecting unit 334 is coupled to the attachment 332. The position detecting unit 334 has a coupling portion 335 that can be detachably attached to the attachment 332. A coupling hole 336 is bored in the coupling portion 335. The coupling hole 336 has a concave part 337 formed therein. The magnetic sensor 306 is located oppositely to the coupling hole 336 of the coupling portion 335. The magnetic sensor 306 of the position detecting unit 334 coupled to the attachment 332 is electrically connected to the ultrasound processor 303 over a signal line, which is not shown, lying through the ultrasonic endoscope 302.

Referring back to FIG. 17, the ultrasonic transducer 326 is connected to one end of a flexible shaft 341 lying through the insertion unit 321. The other end of the flexible shaft 341 is coupled to a DC motor 342 that rotates and drives the flexible shaft 341 lying through the operation unit 322.

The ultrasound processor 303 transmits a pulsating voltage to the ultrasonic transducer 326, and receives an echo signal from the ultrasonic transducer 326. The echo signal sent from the ultrasonic transducer 326 is transmitted to the ultrasound processor 303 via an ultrasound connector 344 over a signal line, which is not shown, contained in an ultrasonic cable 343 by way of the insertion unit 321 and operation unit 322. A magnetic field detection signal sent from the magnetic sensor 306 is transmitted to the ultrasound connector 344 over a signal line, which is not shown, contained in the ultrasonic cable 343 by way of the insertion unit 321 and operation unit 322. The magnetic field detection signal is then transmitted to the position detector 307 over a magnetic field detection cable 346 coupled to the ultrasonic connector 344 via a magnetic field detection connector 345.

The position detector 307 outputs digital position/direction data (x, y, z, ψ, θ, φ) to the ultrasound processor 303. The position/direction data contains information concerning coordinates (x, y, z) of the magnetic sensor 306 relative to the magnetic field source 305 and an orientation thereof [Eulerian angle (ψ, θ, φ)], and is produced based on the magnetic field detection signal.

Thus, in the ultrasound processor 303, echo data is selectively recorded with position/direction data sent from the position detector 307 as a header.

Specifically, echo data produced during one turn of the ultrasonic transducer 326, that is, an amount of echo data necessary to construct one ultrasonic tomographic image is recorded in the form of an echo data block having position/direction data, which indicates the position and direction of the ultrasonic transducer 326 that has made one turn, as a header. This operation is repeated by advancing the distal part of the insertion unit 321. Eventually, a plurality of consecutive echo data blocks is recorded.

Based on the plurality of consecutive echo data blocks, the ultrasound processor 303 constructs a three-dimensional ultrasonic tomographic image and displays it on the observation monitor 304.

In the thus-configured ultrasonic endoscope 302 of this embodiment, prior to an examination intended to construct a three-dimensional ultrasonic image, the signal detection unit 334 is pushed against the distal part 321a of the ultrasonic endoscope 302 with the coupling hole 336 thereof aligned with the attachment 332. The convex part 333 of the attachment 332 is then engaged with the concave part 337 of the coupling hole 336. The position detection unit 334 is mounted on the distal part 321a of the ultrasonic endoscope 302. At the same time, the magnetic sensor 306 is electrically coupled to a signal line, which is not shown, in the ultrasonic endoscope 302.

Moreover, an examination may not be intended to construct a three-dimensional ultrasonic image, the position detection unit 334 may fail, or the ultrasonic endoscope 302 require cleaning. On such an occasion, the position detection unit 334 is pulled out in the distal direction of the ultrasonic endoscope 302 in order to disengage the convex part 333 from the concave part 337. The position detection unit 334 is thus dismounted from the attachment 332.

In the ultrasonic endoscope 302 of this embodiment, when an examination is not intended to construct a three-dimensional ultrasonic image, the position detection unit 334 is dismounted from the distal part 321a. Consequently, the distal part 321a is shorter and lighter. This leads to improved maneuverability.

Moreover, even if the position detection unit 334 fails, a repair is achieved merely by replacing the failing position detection unit 334 with a new position detection unit 334. Maintenance is thus easy to do. Furthermore, since the position detection unit 334 is disposable, cleaning efficiency improves.

The ninth embodiment of the present invention will be described below.

In this embodiment, the description of components identical to those of the eighth embodiment will be omitted. Different points alone will be described mainly.

Figure 19:
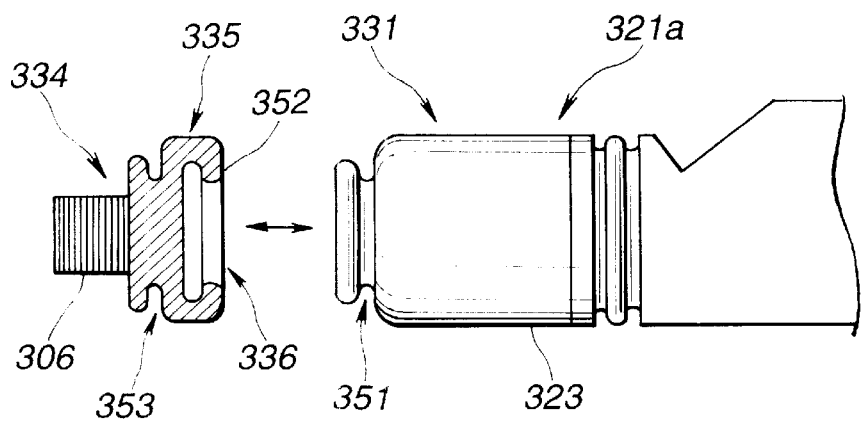
FIG. 19 is a diagram relating to the ninth embodiment of the present invention and showing the structure of a distal part of an ultrasonic endoscope.

In this embodiment, as shown in FIG. 19, the appearance of the distal part 321a of the ultrasonic endoscope 302 is identical to that of an ordinary ultrasonic endoscope. A balloon groove 351 in which a balloon used to dilate a body cavity is fitted is formed in the distal part. A position detection unit 334 is coupled to the balloon groove 351. The position detection unit 334 has a coupling portion 335 detachably attached to the balloon groove 351. A coupling hole 336 is bored in the coupling portion 335. A locking portion 352 is formed in the coupling hole 336. A magnetic sensor 306 is located oppositely to the coupling hole 336 of the coupling portion 335. A groove 353 shaped like the balloon groove 351 is formed in the distal part of the coupling portion 335. The magnetic sensor 306 of the position detection unit 334 coupled to the balloon groove 351 is electrically connected to the position detector 307 over a signal line passing through an ultrasonic endoscope 302, though it is not illustrated.

The other components are identical to those of the eighth embodiment.

In this embodiment, when an examination is intended to construct a three-dimensional ultrasonic image, the signal detection unit 334 is pushed against the distal part 321a of the ultrasonic endoscope 302 with the coupling hole 336 aligned with the balloon groove 351. The locking portion 352 of the coupling hole 336 is engaged with the balloon groove 351. The position detection unit 334 is thus mounted on the distal part 321a of the ultrasonic endoscope 302. At the same time, the magnetic sensor 306 is electrically coupled to a signal line, which is not shown, in the ultrasonic endoscope 302. Herein, when a balloon (not shown) is employed in an examination, the distal part of the balloon is fitted in the groove 353.

An examination may not be intended to construct a three-dimensional image, the position detection unit may fail, or the ultrasonic endoscope 302 may require cleaning. On such an occasion, the position detection unit 334 is pulled out in the distal direction of the ultrasonic endoscope 302 in order to disengage the locking portion 352 from the balloon groove 351. The position detection unit 334 is thus dismounted from the distal part 321*a*.

This embodiment having the foregoing configuration provides the same advantages as the eighth embodiment. In addition, the appearance of the distal part 321*a* with the position detection unit 334 dismounted is the same as that of an ordinary ultrasonic endoscope. Consequently, maneuverability for an examination not intended to construct a three-dimensional ultrasonic image can be further improved.

The tenth embodiment of the present invention will be described below.

In this embodiment, the description of components identical to those of the eighth embodiment will be omitted. Different points alone will be described mainly.

Figure 20:
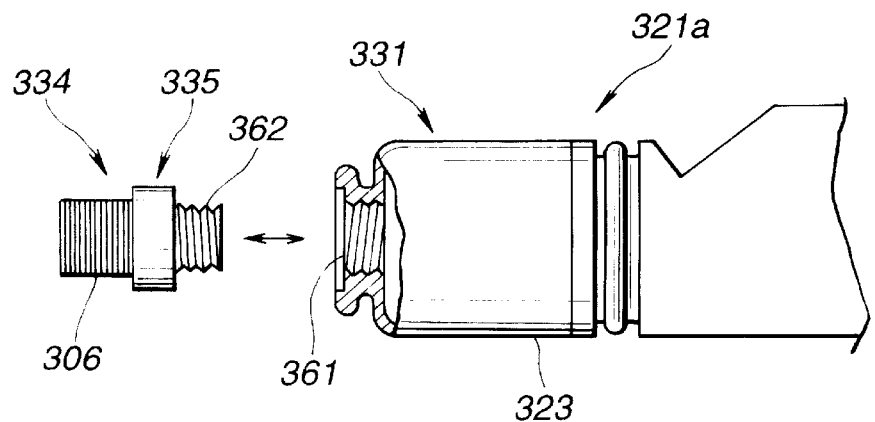
FIG. 20 is a diagram relating to the tenth embodiment of the present invention and showing the structure of a distal part of an ultrasonic endoscope.

In this embodiment, as shown in FIG. 20, the appearance of a distal part 321*a* of an ultrasonic endoscope 302 is identical to that of an ordinary ultrasonic endoscope. A screw hole 361 used to access an ultrasonic medium is bored in the distal part. A position detection unit 334 is coupled to the screw hole 361. The position detection unit 334 has a coupling portion 335 detachably attached to the screw hole 361. The coupling portion 335 is provided with a screw portion 362. A magnetic sensor 306 is located oppositely to the screw portion 362 of the coupling portion 335. The magnetic sensor 306 of the position detection unit 334 coupled to the screw hole 361 is electrically connected to a position detector 307 over a signal line lying through the ultrasonic endoscope 302, though it is not illustrated.

The other components are identical to those of the eighth embodiment.

When an examination is intended to construct a three-dimensional ultrasonic image, a screw (not shown) used to seal an ultrasound propagation medium disposed in the screw hole 361 in the distal part 321*a* of the ultrasonic endoscope 302 is removed. The position detection unit 334 is then mounted in the screw hole 361. At the same time, the magnetic sensor 306 is electrically coupled to a signal line, which is not shown, lying through the ultrasonic endoscope 302.

An examination may not be intended to construct a three-dimensional image, the position detection unit may fail, or the ultrasonic endoscope 302 may require cleaning. On such an occasion, the position detection unit 334 is dismounted, and the screw for sealing the medium (not shown) is tightened.

Similarly to the ninth embodiment, this embodiment having the foregoing configuration provides the same advantages as the eighth embodiment. In addition, the appearance of the distal part 321*a* with the position detection unit 334 dismounted is the same as that of an ordinary ultrasonic endoscope. Maneuverability for an examination not intended to construct a three-dimensional ultrasonic image can further be improved.

The eleventh embodiment of the present invention will be described below.

In this embodiment, the description of components identical to those of the eighth embodiment will be omitted. Different points alone will be described mainly.

Figure 21:
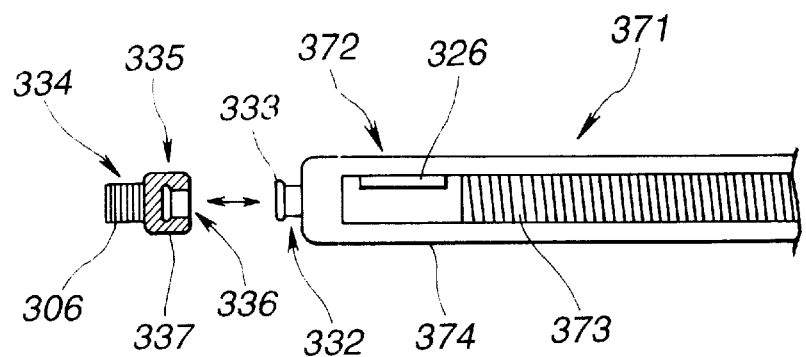
FIG. 21 is a diagram relating to the eleventh embodiment of the present invention and showing the structure of a distal part of an ultrasonic probe.

This embodiment is an embodiment adapted to an ultrasonic probe that lies through a treatment appliance passage channel in an ordinary endoscope, that has its distal end jutted out through an opening of the treatment appliance passage channel located in the distal part of the endoscope, and that transmits or receives ultrasonic waves. As shown in FIG. 21, a distal part 372 of an ultrasonic probe 371 of this embodiment is provided with an ultrasonic transducer 326.

A flexible shaft 373 extends from the ultrasonic transducer 326 proximally to the proximal part of the probe. The flexible shaft 373 is coupled to a connector that is not shown. The ultrasonic transducer 326 is enclosed in a sheath 374. The interior of the sheath 374 is filled with an ultrasound propagation medium that is not shown. An attachment 332 is formed at the distal end of the sheath 374. The attachment 332 has a convex part formed at the tip thereof. A position detection unit 334 is coupled to the attachment 332. The position detection unit 334 has a coupling portion 335 detachably attached to the attachment 332. A coupling hole 336 is formed in the coupling portion 335. The ultrasonic transducer 326 is electrically connected to an ultrasound processor 303 over a signal line lying through the ultrasonic probe 371, though it is not illustrated.

Moreover, the coupling hole 336 has a concave part 337 formed therein. A magnetic sensor 306 is located oppositely to the coupling hole 336 of the coupling portion 335. The magnetic sensor 306 of the position detection unit 334 coupled to the attachment 332 is electrically connected to a position detector 307 over a signal line lying through the ultrasonic probe 371, though it is not illustrated.

The other components are identical to those of the eighth embodiment.

The ultrasonic probe 371 of this embodiment having the foregoing components is analogous to the ultrasonic endoscope 302 of the eighth embodiment. Specifically, when an examination is intended to construct a three-dimensional ultrasonic image, the signal detection unit 334 is pushed against the distal part 372 of the ultrasonic probe 371 with the coupling hole 336 aligned with the attachment 332. The convex part 333 of the attachment 332 is then engaged with the concave part 337 of the coupling hole 336. The position detection unit 334 is thus mounted on the distal part 372 of the ultrasonic probe 371. At the same time, the magnetic sensor 306 is electrically coupled to a signal line, which is not shown, lying through the ultrasonic probe 371.

Moreover, an examination may not be intended to construct a three-dimensional ultrasonic image, the position detection unit 334 may fail, or the ultrasonic probe 371 may require cleaning. On such an occasion, the position detection unit 334 is pulled out in the distal direction of the ultrasonic probe 371. The convex part 333 is then disengaged from the concave part 337. Consequently, the position detection unit 334 is dismounted from the attachment 332.

The ultrasonic probe 371 of this embodiment provides the same advantages as the ultrasonic endoscope 302 of the eighth embodiment.

The twelfth embodiment of the present invention will be described below.

In this embodiment, the description of components identical to those of the eighth embodiment will be omitted. Different points alone will be described below.

Figure 22:
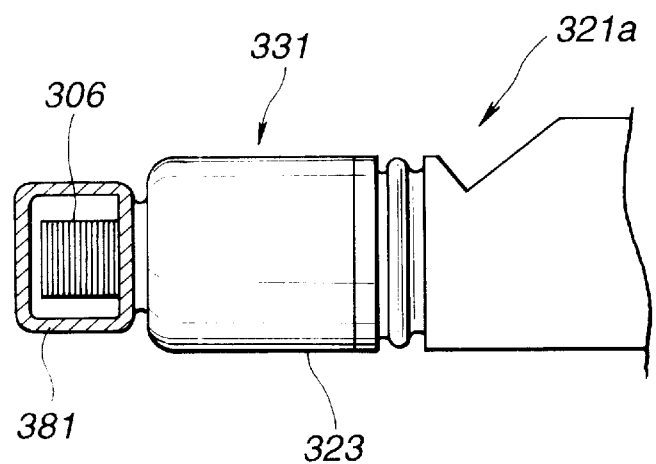
FIG. 22 is a diagram relating to the twelfth embodiment of the present invention and showing the structure of a distal part of an ultrasonic endoscope.

In this embodiment, as shown in FIG. 22, a distal part 321 of an ultrasonic endoscope 302 is provided with a magnetic sensor 306. The magnetic sensor 306 is enclosed in a cover 381. The cover 381 is made of a material resistive to chemicals including glutaraldehyde that is a generally employed disinfectant (polyethylene, polymethyl pentene, polysulfone, silicon rubber, etc.).

The other components are identical to those of the eighth embodiment.

In this embodiment having the foregoing components, since the magnetic sensor 306 is enclosed in the cover 381, the magnetic sensor 306 will not be stained with a disinfectant or the like during cleaning or sterilization using the disinfectant.

Consequently, the ultrasonic endoscope 302 of this embodiment can be cleaned or sterilized in the same manner as an ordinary ultrasonic endoscope without the necessity of following a special procedure.

The thirteenth embodiment of the present invention will be described below.

In this embodiment, the description of components identical to those of the eleventh and twelfth embodiments will be omitted. Different points alone will be described below.

Figure 23:
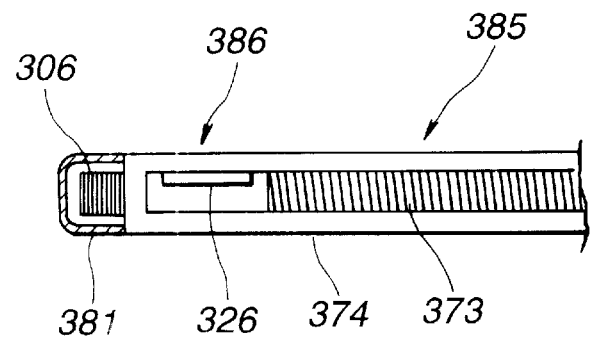
FIG. 23 is a diagram relating to the thirteenth embodiment of the present invention and showing the structure of a distal part of an ultrasonic probe.

This embodiment is an embodiment adapted to an ultrasonic probe that is passed through a treatment appliance passage channel in an ordinary endoscope, that has the tip thereof jutted out of an opening of the treatment appliance passage channel located in the distal part of the endoscope, and that transmits or receives ultrasonic waves. As shown in FIG. 23, similarly to the ultrasonic endoscope 302 of the twelfth embodiment, a distal part 386 of an ultrasonic probe 385 of this embodiment is provided with a magnetic sensor 306. The magnetic sensor 306 is enclosed in a cover 381. The cover 381 is made of a material resistive to chemicals including glutaraldehyde that is a generally employed disinfectant (polyethylene, polymethyl pentene, polysulfone, silicon rubber, etc.).

The other components are identical to those of the eleventh embodiment.

In this embodiment having the foregoing components, the magnetic sensor 306 is enclosed in the cover 381. The magnetic sensor 306 will not be stained with a disinfectant or the like during cleaning or sterilization using the disinfectant.

Consequently, similarly to the ultrasonic endoscope 302 of the twelfth embodiment, the ultrasonic probe 385 of this embodiment can be cleaned or sterilized according to the same procedure as an ordinary ultrasonic probe without the necessity of following a special procedure.

The fourteenth embodiment of the present invention will be described below.

In this embodiment, the description of components identical to those of the twelfth embodiment will be omitted. Different points alone will be described below.

Figure 24:
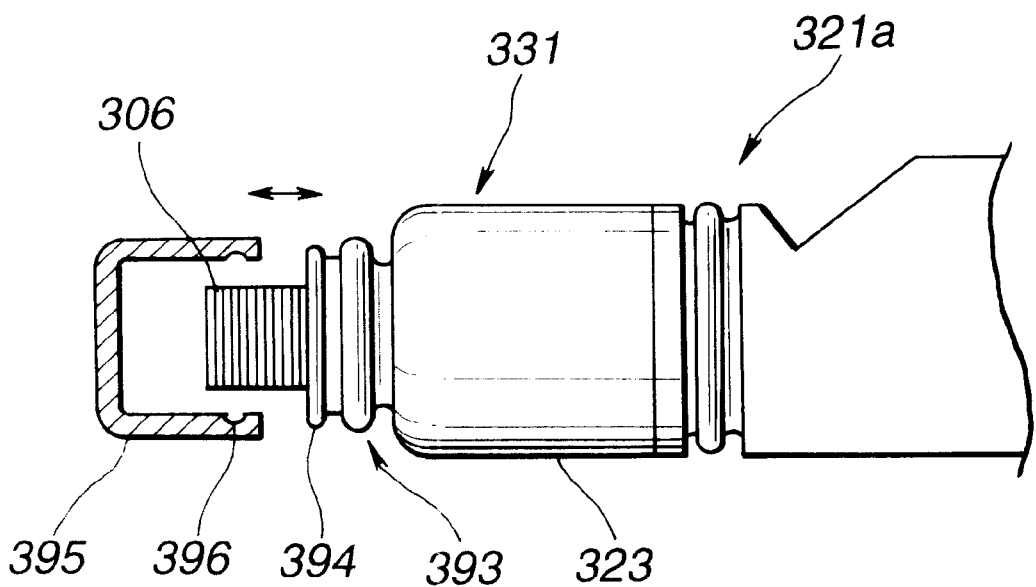
FIG. 24 is a diagram relating to the fourteenth embodiment of the present invention and showing the structure of a distal part of an ultrasonic endoscope.

In this embodiment, as shown in FIG. 24, a distal part 321a of an ultrasonic endoscope 302 is provided with a cover attachment 393. The cover attachment 393 has a convex part 394. A magnetic sensor 306 is mounted in the cover attachment 393. A cover 395 enclosing the magnetic sensor 306 is attached to the cover attachment 393. The cover 395 has a concave part 396 formed in the inner surface of a portion thereof to be attached to the cover attachment 393.

The other components are identical to those of the twelfth embodiment.

Prior to an examination, the cover 395 is pushed against the cover attachment 393. The cover 395 is mounted on the distal part 392 with the convex part 394 of the cover attachment 393 engaged with the concave part 396 of the cover 395. The cover 395 is disposable. When the examination is completed, the cover 395 is pulled out in the distal direction of the ultrasonic endoscope 391. The convex part 394 is disengaged from the concave part 396, whereby the old cover 395 is removed.

In the ultrasonic endoscope 391 of this embodiment, when the cover 395 must be cleaned or sterilized, the cover 395 should merely be replaced with a new one. This results in improved cleaning efficiency.

The fifteenth embodiment of the present invention will be described.

In this embodiment, the description of components identical to those of the eleventh to fourteenth embodiments will be omitted. Different points alone will be described mainly.

Figure 25:
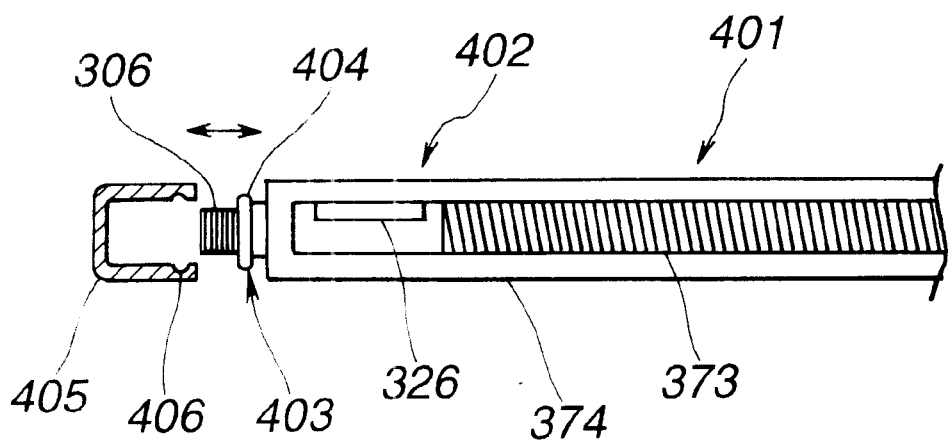
FIG. 25 is a diagram relating to the fifteenth embodiment of the present invention and showing the structure of a distal part of an ultrasonic probe.

This embodiment is an embodiment adapted to an ultrasonic probe that is passed through a treatment appliance passage channel in an ordinary endoscope, that has a tip thereof jutted out through an opening of the treatment appliance passage channel located in the distal part of the endoscope, and that transmits or receives ultrasonic waves. As shown in FIG. 25, similarly to the ultrasonic endoscope 302 of the fourteenth embodiment, a distal part 402 of an ultrasonic probe 401 is provided with a cover attachment 403. The cover attachment 403 has a convex part 404. A magnetic sensor 306 is mounted in the cover attachment 403. A cover 405 enclosing the magnetic sensor 306 is attached to the cover attachment 403. The cover 405 has a concave part 406 formed in the inner surface of a portion thereof to be attached to the cover attachment 403.

The other components are identical to those of the eleventh embodiment.

Prior to an examination, the cover 405 is pushed against the cover attachment 403. The cover 405 is mounted on the distal part 402 with the concave part 406 of the cover 405 engaged with the convex part 404 of the cover attachment 403. The cover 405 is disposable. When the examination is completed, the cover 405 is pulled in the distal direction of the ultrasonic probe 401. The convex part 404 is thus disengaged from the concave part 406, whereby the old cover 405 is removed.

In the ultrasonic probe 401 of this embodiment, similarly to the ultrasonic endoscope 302 of the fourteenth embodiment, when the cover 405 must be cleaned or sterilized, the cover 405 should merely be replaced with a new one. This results in improved cleaning efficiency.

The sixteenth embodiment of the present invention will be described below in connection with FIG. 26.

An ultrasonic diagnosis system of this embodiment consists of: an ultrasonic endoscope 501 serving as an intracorporeal ultrasonic probe; a light source apparatus 502 for supplying illumination light required for viewing an optical image of an examined region; a video processor 503 for producing an optical view image of the examined region; an ultrasonic observation apparatus 504 for producing a two-dimensional ultrasonic tomographic image of the examined region; an observation monitor 505 for displaying an optical view image and ultrasonic tomographic image; a position detector 506 for detecting the position of an insertion unit of the ultrasonic endoscope 501; an ultrasonic three-dimensional image processor 507 for producing a three-dimensional ultrasonic image; an image processing monitor 508 for displaying a three-dimensional ultrasonic image; and cables for linking these apparatuses.

The ultrasonic endoscope 501 has a large-diameter operation unit 510 formed continuously to the proximal end of an elongated insertion unit 509 that is inserted into a body cavity. A light source cable 511 to be coupled to the light source apparatus 502 and an ultrasonic cable 512 to be coupled to the ultrasonic observation apparatus 504 extends from the lateral side of the operation unit 510.

Figure 27:
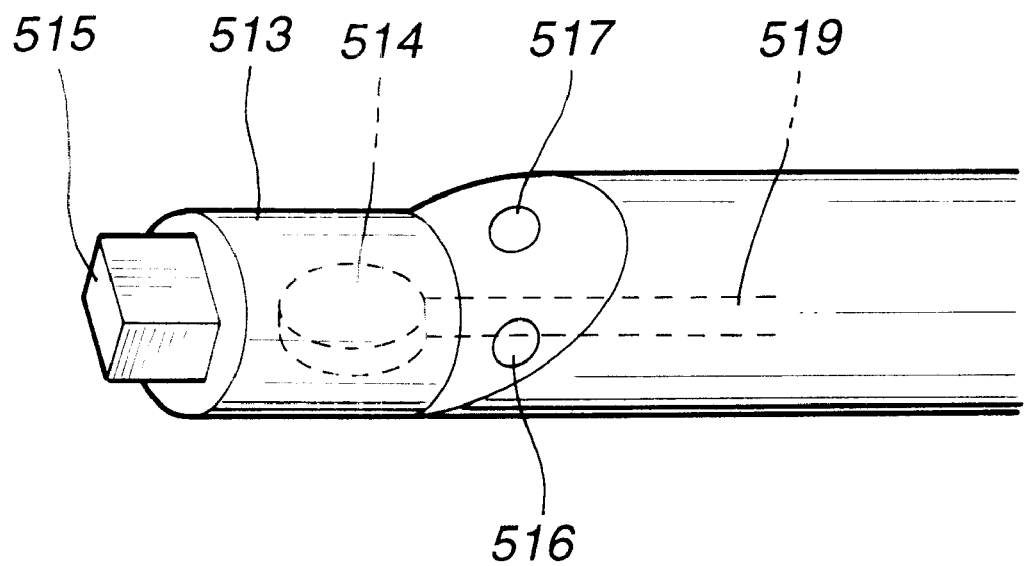

A distal cap 513 is mounted on the distal end of the insertion unit 509. An ultrasonic transducer 514 for transmitting or receiving ultrasonic waves is, as shown in FIG. 27, incorporated in the distal cap 513 so that the ultrasonic transducer 514 can rotate. A magnetic sensor 515 for detecting a magnetic field is mounted on the distal end of the distal cap 513. An observation light irradiation window 516 and CCD camera 517 are mounted on the proximal part of the distal cap 513. Moreover, a bending portion 518 capable of being angled freely in order to move the distal cap 513 in directions indicated with bold arrows is formed at the proximal end of the distal cap 513.

A flexible shaft 519 having one end thereof coupled to the ultrasonic transducer 514 is incorporated in the insertion unit 509, whereby the ultrasonic transducer 514 is rotated. The other end of the flexible shaft 519 is routed to the operation unit 510 and coupled to a DC motor 520 for rotating and driving the flexible shaft 519. The operation unit 510 has an angling knob 521 used to angle the bending portion 518, a three-dimensional scanning start switch 522A, and a three-dimensional scanning end switch 522B.

The light source cable 511 contains light guide fibers (not shown) over which observation light a emanating from the light source apparatus 502 is propagated to the observation light irradiation window 516, and a signal line (not shown) over which a CCD signal b sent from a CCD camera 517 is received by the video processor 503. A light source connector 523 via which the light source cable 511 is coupled to the light source apparatus 502 is coupled to the end of the light source cable 511. The light source apparatus 502 is provided with a lamp 524 for generating observation light a.

Moreover, a video cable 526 is coupled to the light source connector 523 via a small connector 525 formed at an end of the light source connector 523. The light source apparatus is connected to the video processor 503 over the video cable 526. The video processor 503 produces a video signal representing an optical view image of an examined region by processing a CCD signal b, and outputs a resultant signal to the observation monitor 505.

The ultrasonic cable 512 contains a signal line over which a pulsating voltage is transmitted from the ultrasonic observation apparatus 504 to the ultrasonic transducer 514, and an echo signal c from the ultrasonic transducer 514 is received by the ultrasonic observation apparatus 504. The ultrasonic cable 512 also contains a signal line (not shown) over which a magnetic field detection signal d sent from the magnetic sensor 515 and a three-dimensional scanning start/end signal sent from a three-dimensional scanning start switch 522A or three-dimensional scanning end switch 522B is received by the position detector 506. An ultrasound connector 527 via which the operation unit is connected to the ultrasonic observation apparatus 504 is coupled to an end of the ultrasonic cable 512. The transmission route of the three-dimensional scanning start/end signal is the same as that of the magnetic field detection signal d. The illustration of the transmission route is omitted.

The ultrasonic observation apparatus 504 produces a tomographic image signal representing a two-dimensional ultrasonic tomographic image of an examined region by processing the echo signal c. The ultrasonic observation apparatus 504 then outputs the tomographic image signal to the observation monitor 505 and outputs digital echo data to the ultrasonic three-dimensional image processor 507.

Moreover, a position detection cable 529 is coupled to the ultrasound connector 527 via a small connector 528 formed at an end of the ultrasound connector 527. The ultrasonic observation apparatus is connected to the position detector 506 over the position detection cable 529. The position detector 506 is provided with a magnetic field source 530 for generating a magnetic field. Based on a magnetic field detection signal d representing a magnetic field generated by the magnetic field source 530, digital position/direction data is produced and output to the ultrasonic three-dimensional image processor 507.

The ultrasonic three-dimensional image processor 507 is, as shown in FIG. 28, provided with a recording unit 531 that is a large-capacity recording means for recording echo data sent from the ultrasonic observation apparatus 504 together with position/direction data sent from the position detector 506, such as, a hard disk or magneto-optical disk; a coordinate transformation circuit 532 for transforming coordinates indicated by echo data recorded in the recording unit 531; a three-dimensional memory 533 for recording data resulting from coordinate transformation; and a three-dimensional image processing circuit 534 for performing various kinds of image processing including the processing of constructing a three-dimensional ultrasonic image according to the data stored in the three-dimensional memory 533.

Moreover, the ultrasonic three-dimensional image processor 507 has a three-dimensional density calculation circuit 539. The three-dimensional density calculation circuit 539 consists of: a switch 535 that opens or closes in response to a three-dimensional scanning start/end signal sent from the three-dimensional scanning start switch 522A or three-dimensional scanning end switch 522B; a position specification circuit 536 for computing with which positions in a scanned space locations of echo data to be recorded successively in the recording unit 531 coincide, and for specifying the positions; a scanned position count memory 537 for counting the number of times, by which a scanning spot defined by the ultrasonic endoscope 501 crosses each position in the space, according to the positions specified by the position specification circuit 536, and for grasping areas scanned three-dimensionally by the ultrasonic endoscope 501; and a three-dimensional scanning density graphic production circuit 538 for producing a graphic, which depicts three-dimensional scanning densities or frequencies of three-dimensional scanning within the space, according to count values provided by the scanned position count memory 537.

The ultrasonic three-dimensional graphic processor 507 includes a display circuit 540 for switching an output of the three-dimensional image processing circuit 534 and an output of the three-dimensional scanning density calculation circuit 539 or superimposing one output on the other output, and converting a resultant signal into an analog signal. The display circuit 540 outputs a three-dimensional ultrasonic image, a three-dimensional scanning density graphic that is a graphic depicting frequencies of three-dimensional scanning, or an image produced by superimposing the three-dimensional scanning density graphic on the three-dimensional ultrasonic image to the image processing monitor 508.

Next, the operations of the ultrasonic diagnosis system of this embodiment having the foregoing components will be described.

The ultrasonic endoscope 501 is inserted into a tubular organ in a subject's body, for example, the stomach, esophagus, or large intestine by a user such as a physician.

Observation light a emanating from the ultrasonic endoscope 501 is irradiated through the observation light irradiation window 516 via the light source connector 523 over the light guide fibers contained in the light source cable 511. At this time, a CCD signal b is input from the CCD camera 517 to the video processor 503 by way of the signal line contained in the light source cable 511, the small connector 525 connected to the light source connector 523, and the video cable 526. The CCD signal b represents an optical image that depicts the surface of an examined region which has been imaged by the CCD camera 517. The video processor 503 produces a video signal that represents the surface of the examined region, according to the CCD signal b, and outputs it to the observation monitor 505.

When the DC motor 520 is rotated, the flexible shaft 519 is rotated and driven. The driving force is conveyed to the distal end of the flexible shaft 519, whereby the ultrasonic transducer 514 is rotated. During the rotation, a pulsating voltage transmitted repeatedly from the ultrasonic observation apparatus 504 is applied to the ultrasonic transducer 514. The ultrasonic transducer 514 carries out so-called radial scanning, that is, rotates while transmitting or receiving ultrasonic waves to or from a living body.

An echo signal c sent from the ultrasonic transducer 514 represents the examined region, and stems from radial scanning. The echo signal c is input to the ultrasonic observation apparatus 504 via the ultrasound connector 527 over the signal line contained in the ultrasonic cable 512. The ultrasonic observation apparatus 504 detects the envelope of the echo signal c, outputs a logarithmic function of the echo signal c, converts the echo signal c into a digital signal, and carries out other processing. The ultrasonic observation apparatus 504 thus produces a tomographic image signal representing the examined region, and outputs it to the observation monitor 505.

The ultrasonic observation apparatus 504 produces digital echo data, which represents the examined region, according to the echo signal c, and outputs the digital echo data to the ultrasonic three-dimensional image processor 507. The echo data is data bearing addresses that are values each composed of a distance from the ultrasonic transducer 514 and an angle of rotation for radial scanning, that is, values each corresponding to polar coordinates. Intensities of the echo signal c associated with the addresses are described as the data.

The observation monitor 505 displays an optical view image, which depicts the examined region, according to a video signal sent from the video processor 503. The observation monitor 505 also displays a two-dimensional ultrasonic tomographic image, which depicts the examined region, according to a tomographic image signal sent from the ultrasonic observation apparatus 504. Display of the optical view image and display of ultrasonic tomographic image are switched with input of an instruction entered at an input means such as a keyboard or touch panel that is not shown. Alternatively, both the images are displayed simultaneously.

On the other hand, the magnetic sensor 515 detects a magnetic field generated by the magnetic field source 530. A magnetic field detection signal d sent from the magnetic sensor 515 is input to the position detector 506 by way of the signal line contained in the ultrasonic cable 512, the small connector 528 connected to the ultrasound connector 527, and the position detection cable 529. Based on the magnetic field detection signal d, the position detector 506 outputs digital position/direction data, which contains information concerning the position (x, y, z) and orientation [Eulerian angle ($\psi$, $\theta$, $\phi$)] of the magnetic sensor 515 relative to the magnetic field source 530, to the ultrasonic three-dimensional image processor 507.

In the ultrasonic three-dimensional image processor 507, echo data sent from the ultrasonic observation apparatus 504 is recorded in the recording unit 531 with position/direction data sent from the position detector 506 as a header. Specifically, echo data acquired during one turn of the ultrasonic transducer 514, that is, an amount of echo data required for constructing one ultrasonic tomographic image (hereinafter an echo data block) is recorded in the recording unit 531. At this time, position/direction data that is produced while the ultrasonic transducer 514 makes one turn to acquire the echo data block is recorded as a header of the echo data block. By repeating this operation, a plurality of consecutive echo data blocks is recorded successively.

Now, a three-dimensional scanning method adopted by the ultrasonic diagnosis system of this embodiment will be described below.

Figure 26:
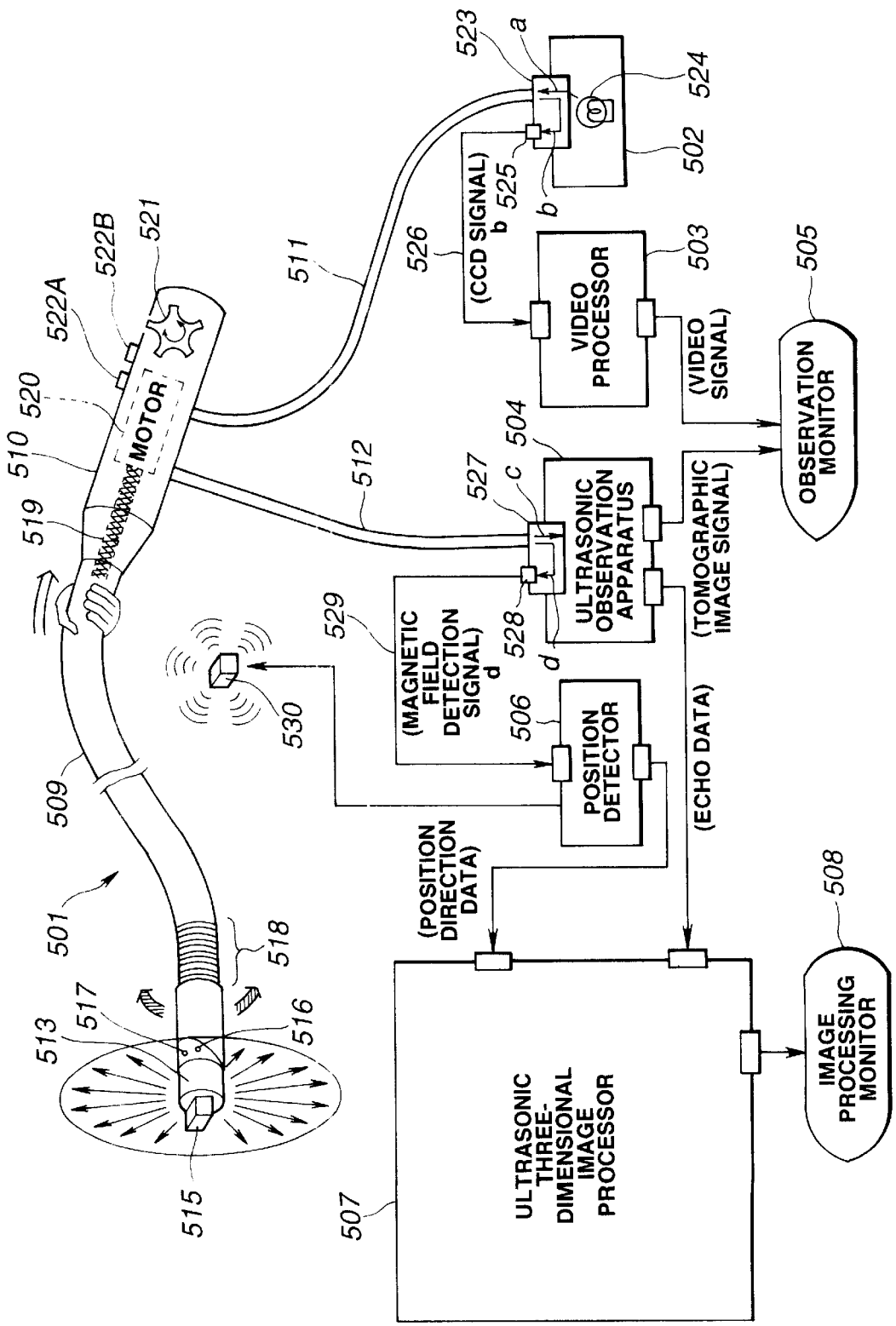
Figure 29A:
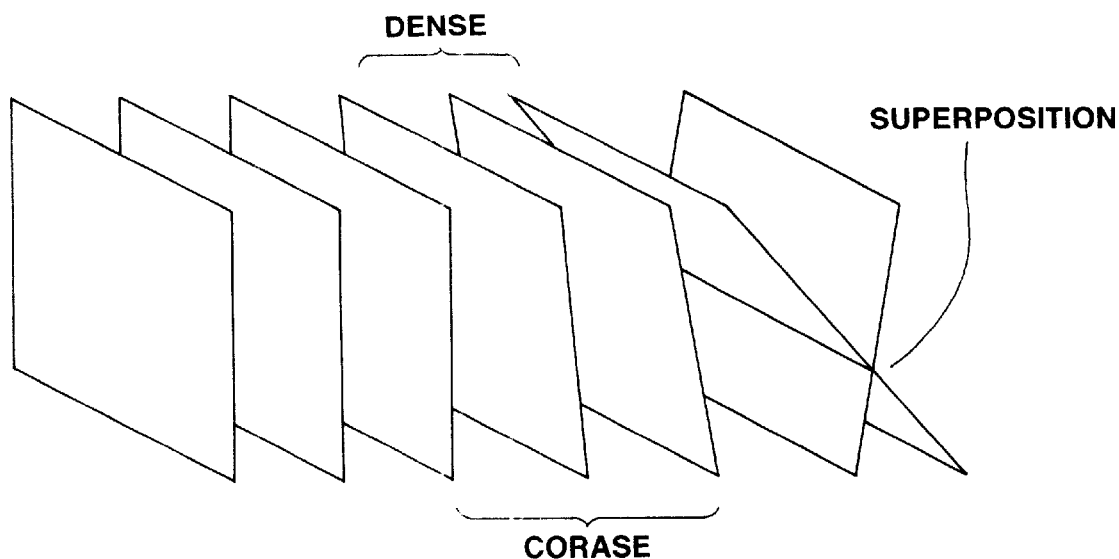
FIG. 29A is an explanatory diagram concerning an operation of the ultrasonic three-dimensional image processor upon interpolation of echo data blocks.

In this embodiment, for three-dimensional scanning, as shown in FIG. 26, a user grabs the insertion unit 509 of the ultrasonic endoscope 501, and moves it in a direction of an arrow (in a direction in which the insertion unit is removed from a subject). Otherwise, the user angles the bending portion 518 by handling the angling knob 521, and thus changes the direction of the distal cap 513. As a result, echo data blocks representing a plurality of ultrasonic tomographic images that are, as shown in FIG. 29A, not mutually parallel but exhibit a coarse three-dimensional scanning density or a coarse frequency of three-dimensional scanning are recorded in the recording unit 531 in the ultrasonic three-dimensional image processor 507. However, in this state, the user cannot recognize whether or not three-dimensional scanning performed over a sufficiently wide range with a sufficiently high density or frequency has been completed in order to construct a three-dimensional ultrasonic image. This leads to a possibility that a density of obtained three-dimensional data becomes irregular.

According to this embodiment, a procedure described below is adopted. Namely, information concerning a three-dimensional scanning density or a frequency of three-dimensional scanning is displayed in a screen on the image processing monitor 508 in the course of three-dimensional scanning.

First, at the start of three-dimensional scanning, a user presses the three-dimensional scanning start switch 522A. A three-dimensional scanning start signal is converted into a certain code (three-dimensional scanning start code) by the position detector 506, and then input to the ultrasonic three-dimensional image processor 507.

The switch 535 in the ultrasonic three-dimensional image processor 507 is closed with input of the three-dimensional scanning start code. This causes the processing of graphically displaying a three-dimensional scanning density to start. At this time, data at all addresses in the scanned position count memory 537 is reset to an initial value of 0. The position specification circuit 536 specifies the locations of echo data blocks to be recorded successively in the recording unit 531 according to position/direction data input in parallel with data input to the recording unit 531.

Figure 30:
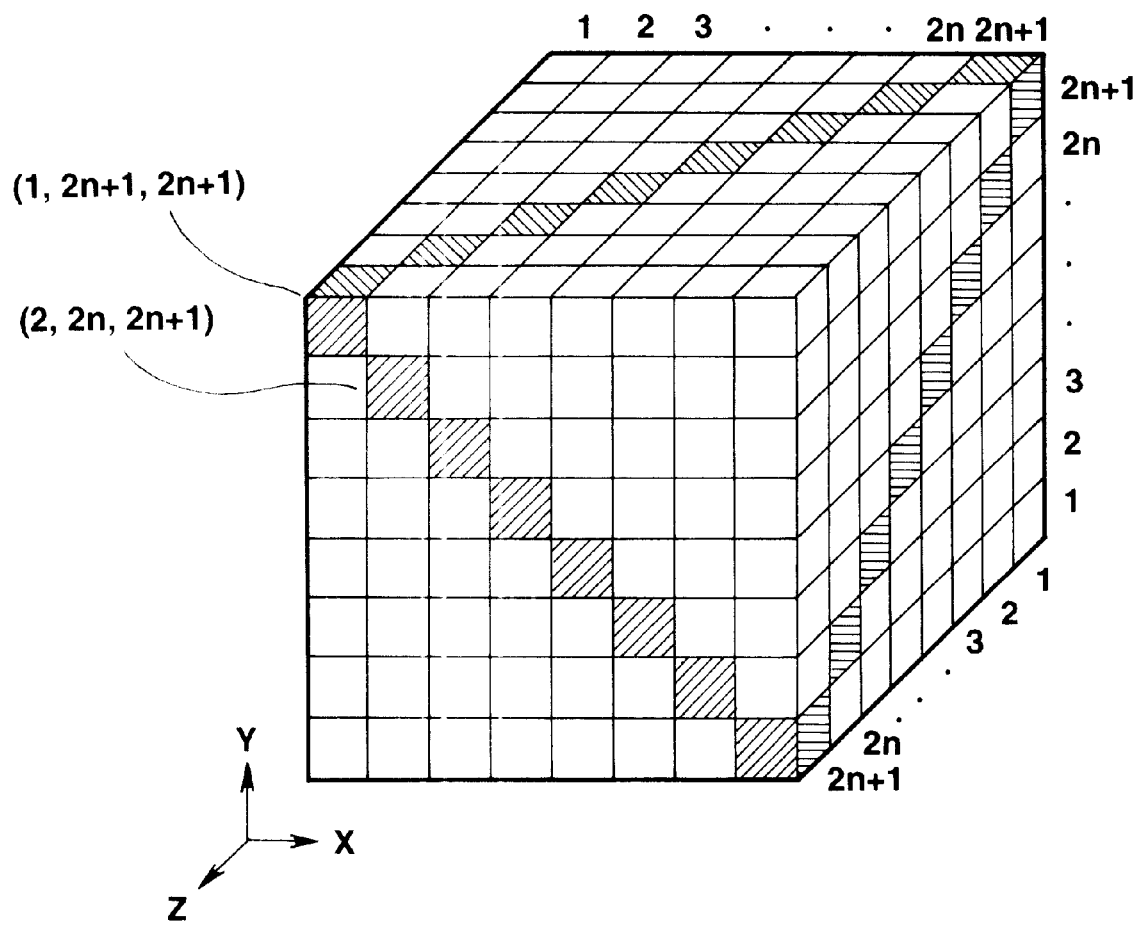

FIG. 30 is a conceptual diagram of addresses in the scanned position count memory 537. Herein, each cube of $(2n+1) \times (2n+1) \times (2n+1) = (2n+1)^3$ (where n denotes a natural number) corresponds to a cubic area in an actual space that is three-dimensionally scanned by the ultrasonic endoscope 501.

The location of an echo data block corresponding to a position in the actual space is, as shown in FIG. 29A, the position of a plane. The position specification circuit 536 increments data of a cube by one and thus updates it at every crossing by the plane. Thus, a frequency by which a scanning spot defined by the ultrasonic endoscope 501 during radial scanning crosses each area in the space is counted. For example, an image represented by an echo data block depicts a plane crossing hatched cubes in FIG. 30. In this case, data items defined by addresses (1, 2n+1, 2n+1), (2, 2n, 2n+1), etc. are incremented by one.

Figure 31:
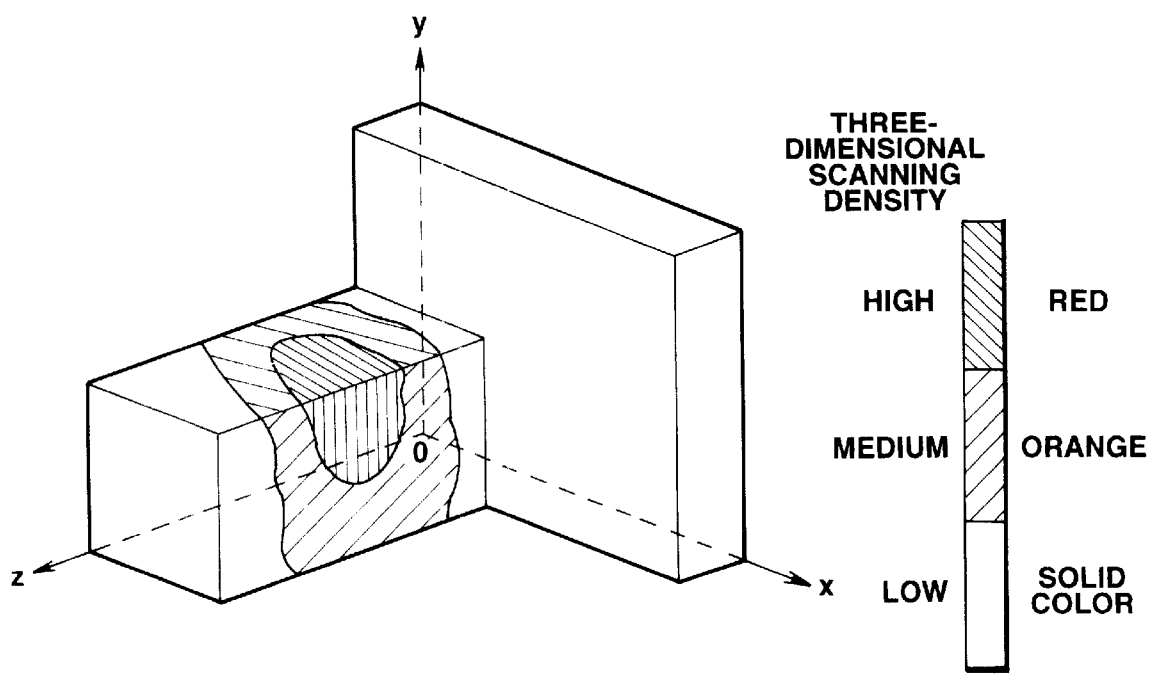

The three-dimensional scanning density graphic production circuit 538 produces, as shown in FIG. 31, a graphic depicting a three-dimensional scanning density or a frequency of three-dimensional scanning by which the ultrasonic endoscope 501 has scanned a subject (hereinafter, a three-dimensional scanning density graphic). FIG. 31 shows the three-dimensional scanning density graphic as a simple three-dimensional image having different tones associated with three-dimensional scanning densities.

The display circuit 540 converts image data of the three-dimensional scanning density graphic produced by the three-dimensional scanning density graphic production circuit 538 into an analog signal, and outputs the analog signal to the image processing monitor 508.

For terminating three-dimensional scanning, a user presses the three-dimensional scanning end switch 522B. A three-dimensional scanning end signal is then converted into a certain code (three-dimensional scanning end code) by the position detector 506, and input to the ultrasonic three-dimensional image processor 507. The switch 535 in the ultrasonic three-dimensional image processor 507 is opened with input of the three-dimensional scanning end code. Thus, the processing of displaying three-dimensional scanning densities is terminated.

Furthermore, the processing sequence may be carried out in real time during three-dimensional scanning. In this case, an image like the one shown in FIG. 31 is displayed on the image processing monitor 508 while being updated sequentially. A user can therefore move the ultrasonic endoscope 501 or angle the bending portion 518, so that the three-dimensional scanning density graphic will be entirely painted in red. Thus, a sufficiently wide range of a subject can be three-dimensionally scanned in order to construct a three-dimensional ultrasonic image. The irregularity in density of three-dimensional data can be suppressed.

Incidentally, for producing a three-dimensional scanning density graphic, position/direction data input from the position detector 506, addresses in the scanned position count memory 537, and a positional relationship among three-dimensional scanning densities must be defined.

In this embodiment, therefore, a position indicated by position/direction data when a three-dimensional scanning start code is input to the ultrasonic three-dimensional image processor 507, that is, the position of the magnetic sensor 515 at the start of three-dimensional scanning is aligned with the center of a cube defined by an address (n+1, n+1, n+1) in the scanned position count memory 537 shown in FIG. 30. An outer apex of a cube defined with an address (1, 1, 1) in the scanned position count memory 537 is associated with an origin O of a three-dimensional scanning density graphic shown in FIG. 31. As for an orientation, the orientation of the top of the magnetic sensor 515 at the start of three-dimensional scanning, that is, the orientation of the top of the distal cap 513 is associated with the z axis shown in FIGS. 30 and 31.

Figure 29B:
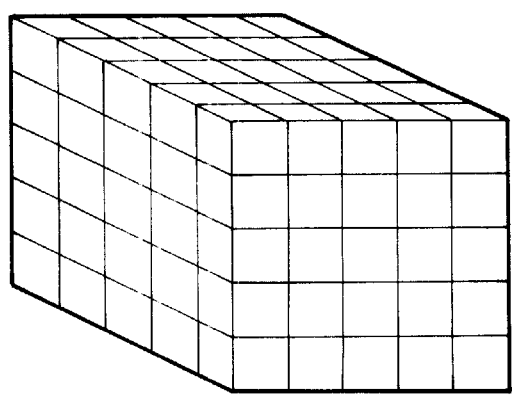
FIG. 29B is an explanatory diagram concerning an operation of the ultrasonic three-dimensional image processor, conceptually showing addresses in a scanned position count memory.

After three-dimensional scanning is completed, the coordinate transformation circuit 532 in the ultrasonic three-dimensional image processor 507 reads echo data blocks recorded in the recording unit 531, and converts polar coordinates indicating addresses into orthogonal coordinates. Furthermore, the coordinate transformation circuit 532 averages echo data blocks representing superposed images like those shown in FIG. 29A out of the plurality of echo data blocks that has been subjected to coordinate transformation. Otherwise, the coordinate transformation circuit 532 interpolates echo data blocks, or produces three-dimensional image data, of which addresses are expressed with three-dimensional orthogonal coordinates, like the one shown in FIG. 29B. The three-dimensional image data is stored in the three-dimensional memory 533.

Figure 32:
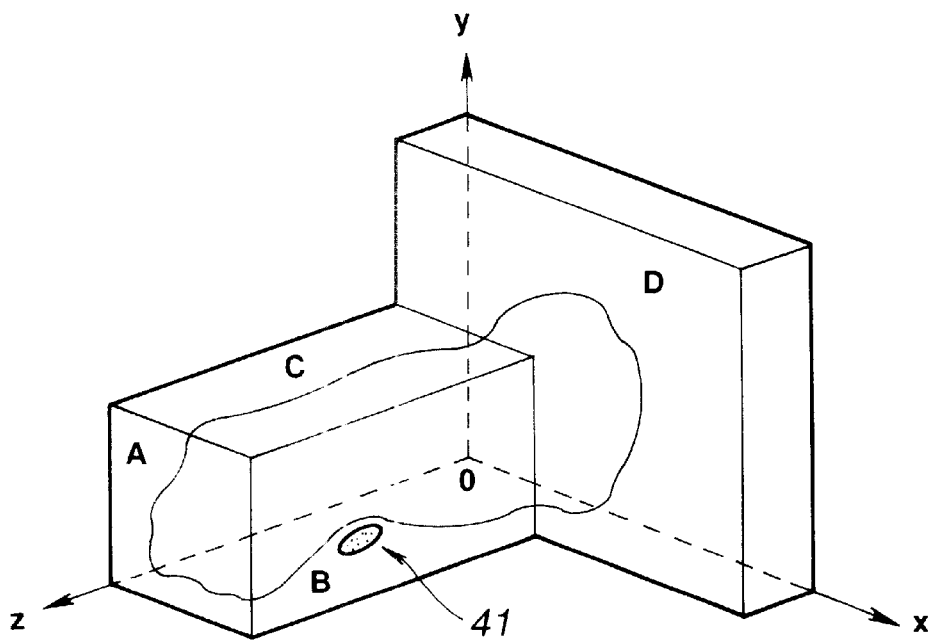
Figure 33:
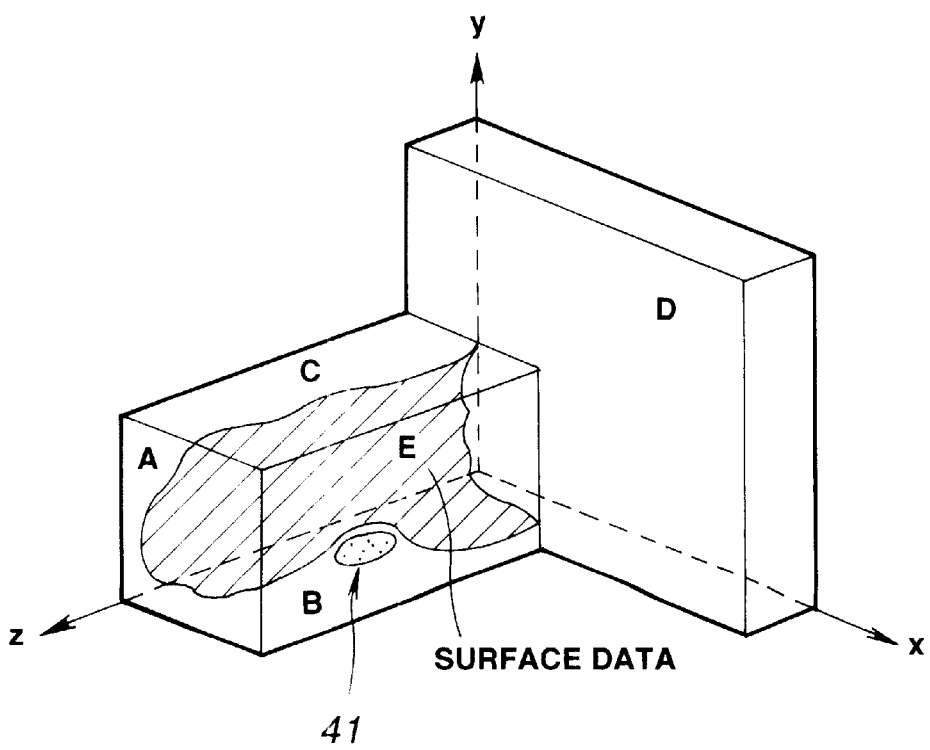

The three-dimensional image processing circuit 534 reads three-dimensional image data from the three-dimensional memory 533, and carries out processing necessary to construct a three-dimensional ultrasonic image like the one shown in FIGS. 32 and 33. The image construction will be outlined later.

The display circuit 540 converts image data of a three-dimensional ultrasonic image constructed by the three-dimensional ultrasonic image processing circuit 534 into an analog signal, and outputs the analog signal to the image processing monitor 508. Thus, a three-dimensional ultrasonic image of an examined region is displayed on the image processing monitor 508.

Figure 34:
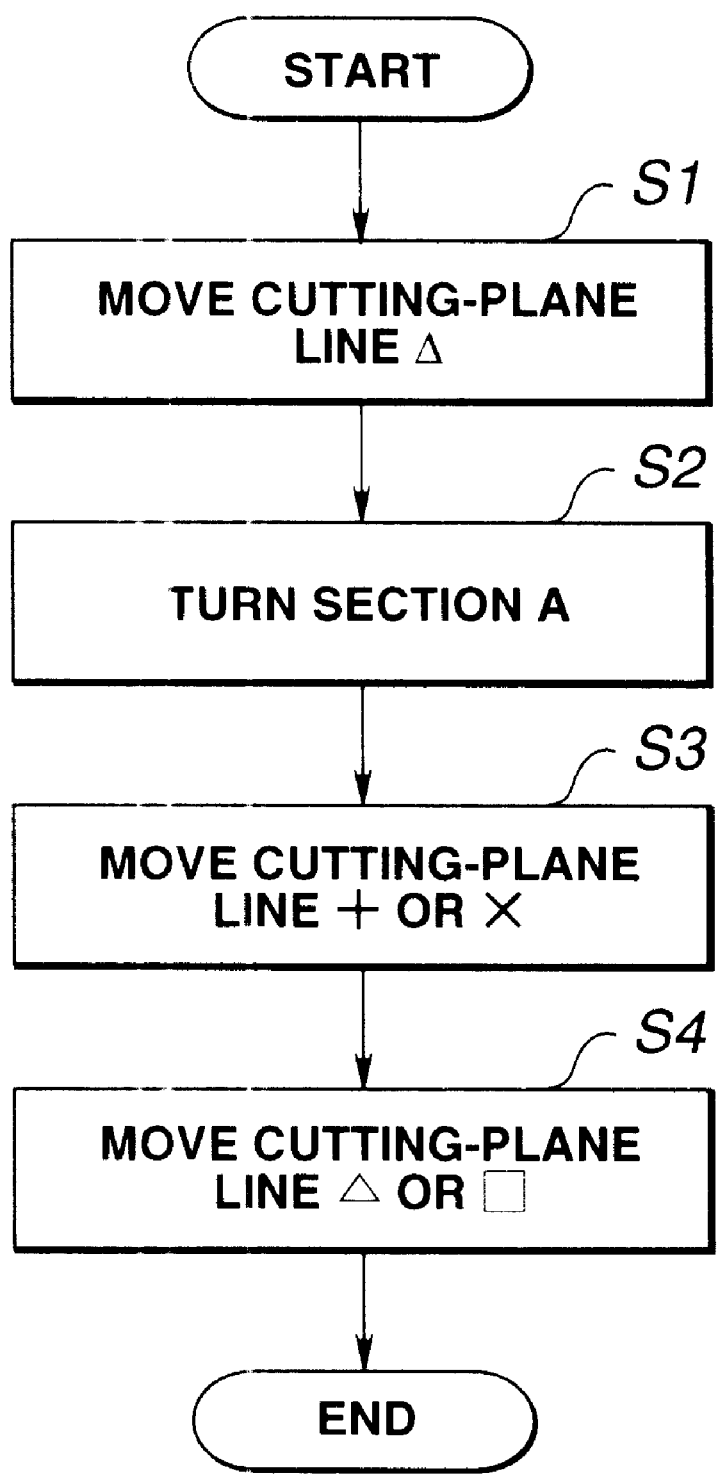

Image construction carried out by the three-dimensional image processing circuit 534 will be described below. FIG. 34 is a flowchart describing section setting that is part of the processing carried out by the three-dimensional image processing circuit 534.

Figure 35:
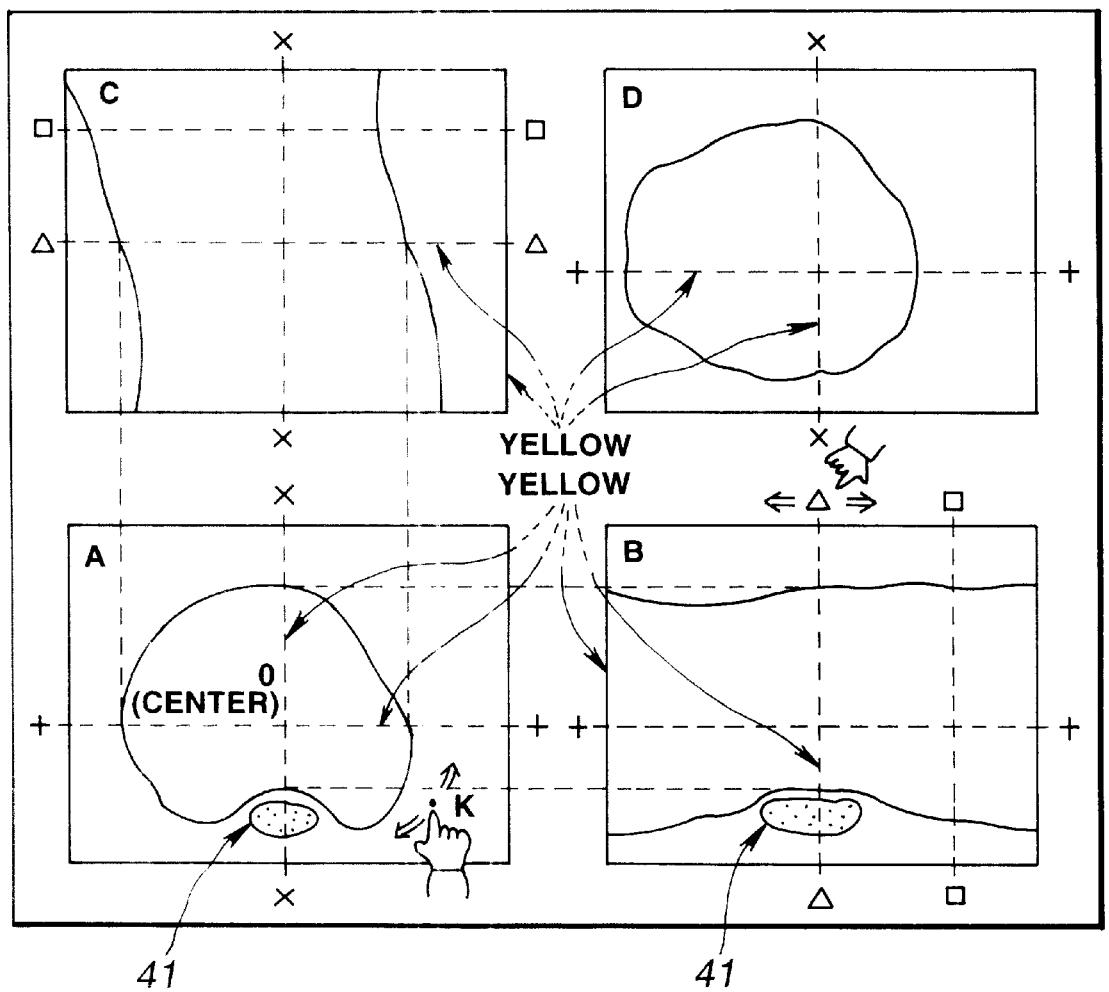

FIG. 35 shows a plurality of sectional images, or more particularly, four sectional images (sectional echo data) to be set for displaying ultrasonic images of an examined region three-dimensionally on the image processing monitor 508 as shown in FIGS. 32 and 33. An area patterned like the skin of a pear indicates a region of interest 541 such as a lesion. These sectional images are displayed on the image processing monitor 508 using three-dimensional image data read from the three-dimensional memory 533.

FIGS. 32 and 33 show a three-dimensional ultrasonic image constructed finally by setting the four sectional images shown in FIG. 35. Sections A, B, C, and D shown in FIGS. 32 and 33 correspond to sectional images A, B, C, and D shown in FIG. 35. (However, the sectional images shown in FIG. 35 correspond to sections resulting from parallel movement or turning of the sections shown in FIGS. 32 and 33. For example, the section A in FIGS. 32 and 33 is turned or moved in parallel so that it will contain the lesion as described below.)

The section C is perpendicular to the sections A and D and corresponds to the sectional image containing a cutting-plane line+in FIG. 35. The section B corresponds to the sectional image containing a cutting-plane line x in FIG. 35. The section A corresponds to the sectional image containing a cutting-plane line Δ in FIG. 35. Moreover, the section D corresponds to the sectional image containing a cutting-plane line □ in FIG. 35.

Incidentally, the cutting-plane lines drawn with dashed lines in FIG. 35, and the frame line of a sectional image being handled are painted in yellow or the like so that they can be identified easily. Moreover, the sectional image can be distinguished from the other sectional images displayed in black and white.

During section setting described in FIG. 34, first, at step S1, a user handles an input means such as a keyboard or touch panel that is not shown. The user slides a cursor Δ located near the sectional image B in directions of arrows in FIG. 35 (in lateral directions in FIG. 35), so that the region of interest 541 such as a lesion will appear in the sectional image A. The cutting-plane line Δ then moves while being interlocked with the cursor. The region of interest 541 then appears in the sectional image A along the cutting-plane line Δ.

At step S2, the user uses the input means to turn the sectional image A with a central point O as a center so that the region of interest 541 will be oriented properly. At this time, a certain point K is moved in directions of arrows in order, whereby the sectional image A is turned. In the sectional image A in FIG. 35, the region of interest 541 is located below the subject to be examined.

At step S3, the input means is used to move the cutting-plane lines + and x so that the cutting-plane line + or x will be set on the region of interest 541. This moving procedure is identical to that for the cursor Δ. The region of interest 541 then appears in the sectional image B or C. In FIG. 35, the cutting-plane line x has been moved.

At step S4, the input means is used to move the cutting-plane lines Δ and □ so that the region of interest 541 will be interposed between the cutting-plane lines Δ and □.

Thus, section setting for setting the sectional images constituting a three-dimensional ultrasonic image, which are shown in FIG. 35, is completed.

After the completion of the section setting, the three-dimensional image processing circuit 534 constructs a three-dimensional ultrasonic image, such as, a simple three-dimensional image that does not depict the surfaces of a tubular organ like the one shown in FIG. 32, or a three-dimensional image having surface data E extracted as shown in FIG. 33. Incidentally, a procedure of extracting the surface data is already known. The description of the procedure will therefore be omitted.

In this embodiment, three-dimensional scanning densities, that is, the frequencies of three-dimensional scanning performed by the ultrasonic endoscope 501 are computed by the three-dimensional scanning density calculation circuit 539. The irregularity in three-dimensional scanning density is indicated as a graphic on the image processing monitor 508. A user can therefore carry out three-dimensional scanning over a sufficiently wide range to construct a three-dimensional ultrasonic image while checking the three-dimensional scanning density graphic. Consequently, the irregularity in density of produced three-dimensional data can be suppressed. Eventually, the ultrasonic endoscope 501 mechanically designed to carry out simple radial scanning alone can be employed. Consequently, the outer diameter of the insertion unit can be made smaller. Besides, three-dimensional data can be produced accurately without suffering from the adverse effect of irregularity in three-dimensional scanning density.

In this embodiment, as shown in FIG. 31, a three-dimensional scanning density graphic is a simple three-dimensional image having different tones associated with three-dimensional scanning densities. A method of displaying the three-dimensional scanning densities in a screen is not limited to this form. Alternatively, the three-dimensional scanning densities may be indicated with different luminance levels instead of the different tones. Otherwise, the three-dimensional scanning densities may be depicted in a plurality of sectional images but not in the simple three-dimensional image.

Figure 36A:
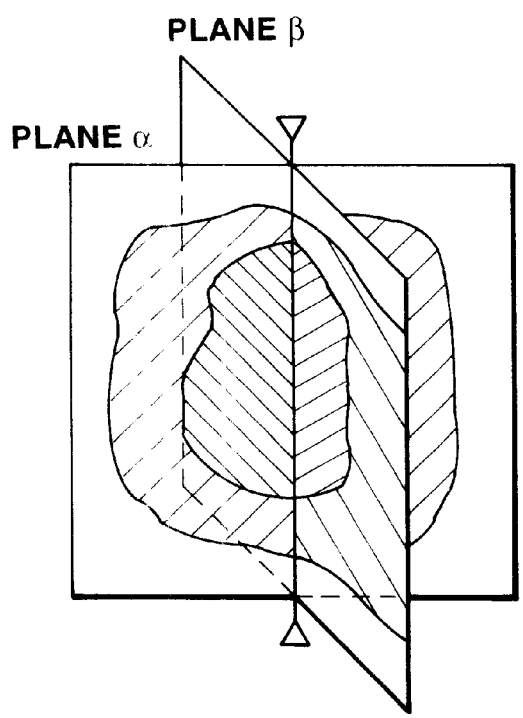
FIGS. 36A and 36B relate to a variant of the sixteenth embodiment.
Figure 36B:
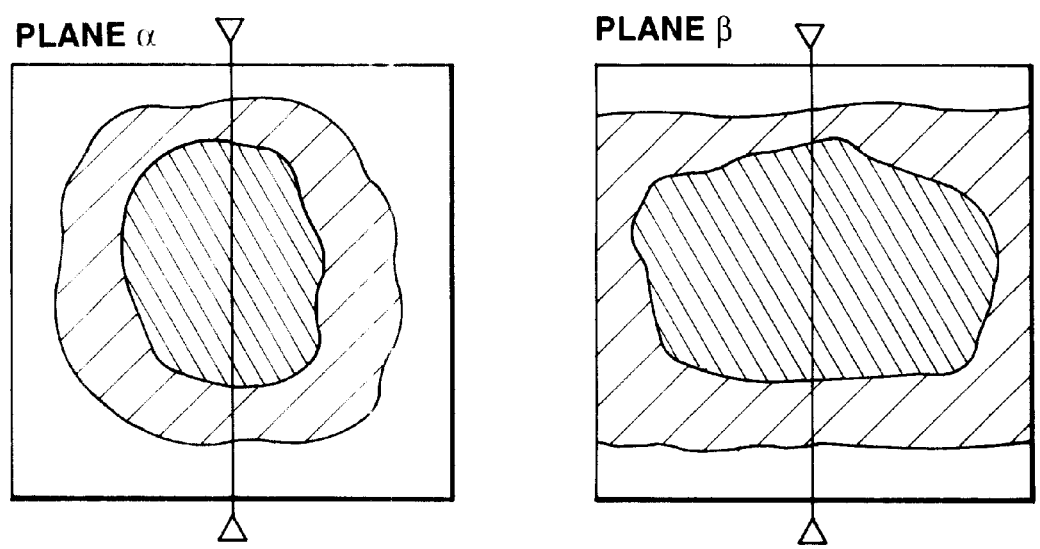

As a variant of the sixteenth embodiment, an example in which the method of displaying an image depicting three-dimensional scanning densities has been modified is shown in FIGS. 36A and 36B.

FIG. 36A shows an example in which three-dimensional scanning densities are depicted in two mutually orthogonal sections of planes α and β. FIG. 36B shows an example in which the two sectional images are displayed while being developed. The number of sectional images may not be two. Alternatively, a larger number of sectional images, such as, a plurality of sectional images perpendicular to the z axis may be employed. Otherwise, such a three-dimensional scanning procedure may be adopted that only cubes indicating lower three-dimensional densities are displayed and three-dimensional scanning is carried on to delete the displayed cubes.

In this embodiment, the magnetic sensor 515 is adopted as a means for detecting a position at which ultrasonic scanning is carried out. Alternatively, an acceleration sensor for computing a position using an acceleration, or any other position detection sensor will do. In this embodiment, the magnetic sensor 515 is mounted on the distal end of the ultrasonic endoscope 501. The magnetic sensor 515 and magnetic field source 530 may be positioned the other way around. The position of the distal part of the ultrasonic endoscope 501 can still be detected.

The seventeenth embodiment of the present invention will be described below.

In this embodiment, the description of components identical to those of the sixteenth embodiment will be omitted. Different points alone will be described mainly.

This embodiment is an example in which the method of computing three-dimensional scanning densities has been modified. The system configuration is identical to that of the sixteenth embodiment shown in FIGS. 26 to 28.

This embodiment is different from the sixteenth embodiment only in the method of computing three-dimensional scanning densities. The difference alone will be described below.

In the sixteenth embodiment, based on position/direction data input in parallel with data input to the recording unit 531, the position specification circuit 536 specifies locations of echo data blocks to be successively recorded in the recording unit 531. Data of a cube in the three-dimensional addressing space in the scanned position count memory 537 is incremented by one every time a position corresponding to the location of the data is crossed by a scanning spot defined by the ultrasonic endoscope 501 during radial scanning. Thus, the number of times by which each area in a corresponding space is crossed by the scanning spot is counted.

By contrast, according to this embodiment, based on position/direction data sent from the position detector 506, the position specification circuit 536 increments data of a cube, whose location corresponds to the position of the magnetic sensor 515, by one at regular intervals. Thus, the density of a scanned point on a trajectory traced by the distal part of the ultrasonic endoscope 501 is computed by counting the number of scanned points. For example, the position of the magnetic sensor 515 represented by the position/direction data may be contained in a cube at an address (1, 1, 1) in FIG. 30. In this case, the data of the cube is incremented by one.

The other operations are identical to those of the sixteenth embodiment.

Even in this embodiment, similarly to the sixteenth embodiment, the irregularity in three-dimensional scanning density can be depicted as a graphic. Three-dimensional data can therefore be produced accurately without being affected by the irregularity in three-dimensional scanning density.

In this embodiment, based on position/direction data, the position specification circuit 536 increments data of a cube, of which location corresponds to the position of the magnetic sensor 515, by one and thus updates the data at regular intervals. Thus, the density of a scanned point on a trajectory traced by the ultrasonic endoscope 501 is determined by counting the scanned points. This embodiment is not limited to this form. As a variant, a trajectory traced by the magnetic sensor 515 may be monitored for a certain period of time by means of the position specification circuit 516. Data items of cubes whose locations correspond to positions along trajectories may be incremented by the number of trajectories and thus updated. Thus, the density of a trajectory traced by the distal end of the ultrasonic endoscope 501 may be determined by counting trajectories.

The eighteenth embodiment of the present invention will be described below.

In this embodiment, the description of components identical to those of the sixteenth embodiment will be omitted. Different points alone will be described.

Figure 37:
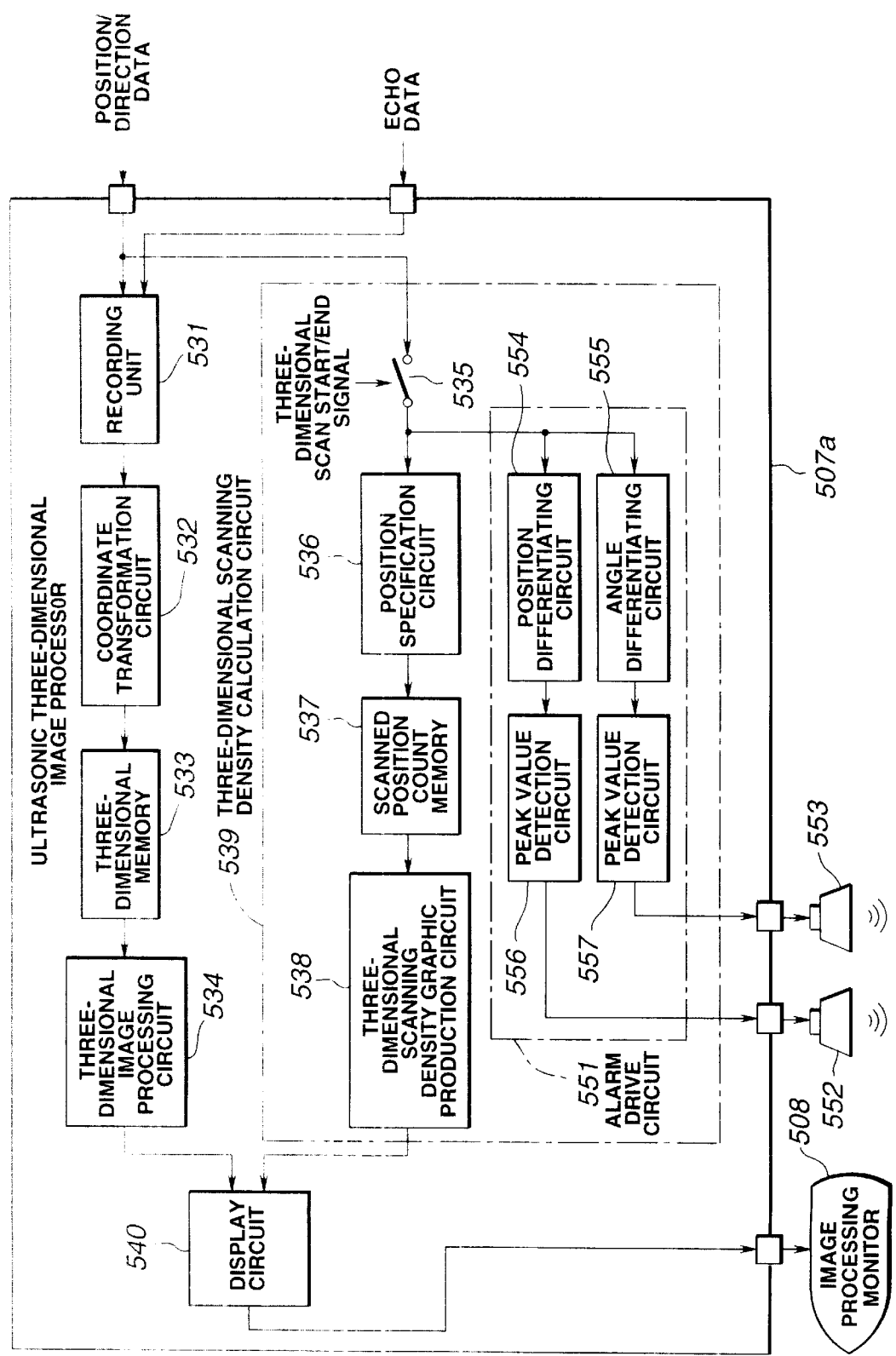
FIG. 37 is a block diagram relating to the eighteenth embodiment of the present invention and showing the configuration of an ultrasonic three-dimensional image processor.

This embodiment will be described in conjunction with FIG. 37.

This embodiment is an example in which an audible sound output means for informing a user of the fact that a three-dimensional scanning density has exceeded a given value by means of a sound is included. This embodiment is different from the sixteenth embodiment in terms of the configuration and operations of the ultrasonic three-dimensional image processor. The difference alone will be described.

An ultrasonic three-dimensional image processor 507a of this embodiment includes the same components as that of the sixteenth embodiment. In addition, an alarm drive circuit 551 for informing a user of the irregularity in density of a point, which is scanned three-dimensionally by the user, by means of an audible sound according to position/direction data is included in the three-dimensional scanning density calculation circuit 539. The alarm drive circuit 551 is connected to alarms 552 and 553 located externally for outputting an alarm sound.

The alarm drive circuit 551 consists of a position differentiating circuit 554 for calculating a change in position of the magnetic sensor 515 according to position/direction data sent from the position detector 506, an angle differentiating circuit 555 for calculating a change in orientation of the magnetic sensor 515, and peak value detection circuits 556 and 557 for detecting peak values of outputs of the position differentiating circuit 554 and angle differentiating circuit 555 respectively.

The other components are identical to those of the sixteenth embodiment.

In this embodiment, the position differentiating circuit in the three-dimensional scanning density calculation circuit 539 sequentially differentiates data (x, y, z) of the position of the magnetic sensor 515 that is extracted from position/direction data sent from the position detector 506. A change in derivative is output to the peak value detection circuit 556. The peak value detection circuit 556 holds the peak value of the derivative for a certain period of time, and compares the peak value with a certain threshold. When the peak value exceeds the threshold, a voltage is applied to the alarm 552 in order to drive the alarm 552. This causes the alarm 552 to output an alarm sound when a derivative of position information exceeds a given value.

Moreover, the angle differentiating circuit 555 sequentially differentiates an orientation [Eulerian angle ($\psi$, $\theta$, $\phi$)] of the magnetic sensor 515, which is indicated by position/direction data sent from the position detector 506, and outputs a change in derivative to the peak value detection circuit 557. The peak value detection circuit 557 and alarm 553 carry out operations similar to operations for handling the position information. When the derivative of angle information exceeds a given value, an alarm sound is output.

The other operations are identical to those of the sixteenth embodiment.

In this embodiment, the position differentiating circuit 554 and angle differentiating circuit 555 in the three-dimensional scanning density calculation circuit 539 computes derivatives of position information and angle information, which are extracted from an output of the magnetic sensor 515. The alarms 552 and 553 inform a user of the fact that the derivatives have exceeded certain specific values by means of an audible sound. Thus, the user is reported the irregularity in three-dimensional scanning density. When a change in position or angle of each tomographic image (derivative) is too large to construct a three-dimensional ultrasonic image, a user can recognize the fact owing to an alarm sound emitted by the alarm 552 or 553. Three-dimensional scanning can then be resumed. The ultrasonic endoscope 1 whose mechanical structure is intended to perform simple radial scanning alone can be used to reduce the outer diameter of the insertion unit. Moreover, three-dimensional data can be acquired accurately while being unaffected by the irregularity in three-dimensional density.

Incidentally, when an ultrasonic probe to be inserted into a body cavity, such as, an ultrasonic endoscope is employed, a distance from a reference position of a subject, for example, the incisor tooth thereof to a lesion can be calculated by inspecting a relationship in position or azimuth between a specific region of the subject and a scanning spot defined by ultrasonic waves. This will prove useful in a clinical practice for identifying the position of a lesion during a re-examination.

Japanese Unexamined Patent Publication No. 62-68442 has proposed an ultrasonic diagnosis system having a magnetic sensor incorporated in an ultrasonic probe so as to indicate information of the position and direction of the ultrasonic probe using a body mark or the like. In this system, a magnetic field source is embedded in a bed, and a subject is asked to lie down on the bed. The magnetic sensor mounted on or incorporated in the ultrasonic probe is used to measure the positions of an apical breast bone, the umbilicus, the right lateral region, or the left lateral region. A body mark is then produced. When an ultrasonic tomographic image is acquired and displayed, a position relevant to the image and an angle relative to the bed are measured by the magnetic sensor. Information of the position and angle of the ultrasonic probe is indicated in the body mark chart.

However, in the system disclosed in the Japanese Unexamined Patent Publication No. 62-68422, the reference position that is the position of the apical breast bone, umbilicus, right lateral region, or left lateral region is measured in advance and the body mark chart is created in advance. The information of the position and angle of the ultrasonic probe is then indicated. For this reason, when a subject moves on the bed during an examination, the reference position becomes inconsistent with the one in the body mark. This poses a problem that the information of the position and angle of the ultrasonic probe becomes inaccurate.

Moreover, the position detecting means for detecting a position using a magnetic sensor usually includes a magnetic field source for generating a magnetic field. According to the U.S. Pat. No. 5,398,691, and Japanese Unexamined Patent Publications Nos. 4-332544 and 62-68422, the magnetic field source is mounted on a bed. In the system disclosed in Japanese Unexamined Patent Publication No. 6-261900, the magnetic field source is incorporated in an arm mounted in a host processor and made of a material that will not affect a magnetic field.

However, a bed has many members that disorder a magnetic field, such as, a metallic column. When a magnetic field source is mounted on such a bed, a generated magnetic field may be disordered terribly. This poses a problem that the position and direction of an ultrasonic probe cannot be measured accurately. Moreover, normally, as the magnetic sensor lies farther, away the precision in detection achieved by the position detecting means deteriorates. When the magnetic field source is incorporated in an arm mounted on a host processor or the like, the distance of the magnetic field source from the magnetic sensor becomes too large depending on the position of the host processor or the way of mounting the arm. Consequently, the precision in detecting the position and direction of the ultrasonic probe deteriorates. This poses a problem that position information cannot be acquired accurately.

Examples of the configuration of an ultrasonic diagnosis system that has solved the above problems will be presented as the nineteenth and twentieth embodiments below.

The nineteenth embodiment of the present invention will be described below.

In this embodiment, the description of components identical to those of the sixteenth embodiment will be omitted. Different points alone will be described mainly.

Figure 38:
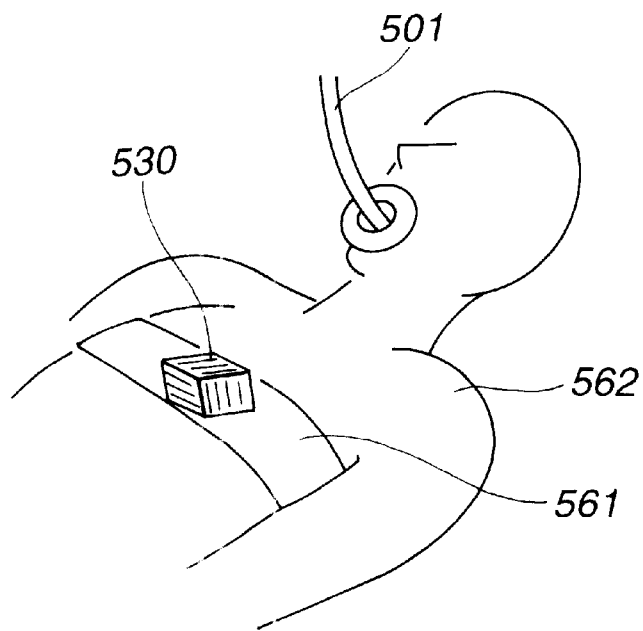
FIG. 38 is an explanatory diagram relating to the nineteenth embodiment of the present invention and showing the layout of components on a subject during ultrasonic diagnosis.

FIG. 38 is an explanatory diagram showing the layout of components on a subject during ultrasonic diagnosis in accordance with this embodiment.

This embodiment is concerned with a configuration in which the reference position of a subject and the position and direction of an ultrasonic probe can be grasped accurately.

As shown in FIG. 38, in this embodiment, a magnetic field source 530 is fixed to a belt 561 made of a material not disordering a magnetic field, such as, a rubber or leather. The belt 561 is worn by a subject 562 (bound about his/her chest in this case). At this time, the belt 561 is always located at a specific position serving as a reference on the subject 562.

The other components are identical to those of the sixteenth embodiment.

According to this embodiment, the belt 561 is always located at the reference position on the subject 562. The magnetic field source 530 is fixed to the body of the subject 562 at the reference position or a certain position relative to the reference position. The position or direction of the ultrasonic endoscope 501 relative to the reference position can be measured more accurately. It is easy to identify the position of a lesion during a re-examination.

In this embodiment, the magnetic field source 530 is bonded to the belt 561 made of a material not disordering a magnetic field, such as, a rubber or leather. The belt 561 is bound about the body of the subject 562. Compared with when the magnetic field source 530 is mounted on a bed or the like, the fear of disordering a magnetic field is limited. Moreover, compared with when the magnetic field source 530 is incorporated in an arm or the like formed on a host processor or the like, the magnetic sensor 515 and magnetic field source 530 are located mutually closely. There is no fear that the precision in detecting the position and direction of the ultrasonic endoscope 501 deteriorates. The position and direction of the ultrasonic endoscope 501 can be measured accurately with high precision by means of the magnetic sensor 515.

The other operations and advantages are identical to those of the sixteenth embodiment.

In this embodiment, the magnetic sensor 515 is incorporated in the distal part of the ultrasonic endoscope 501 in the same manner as that in the first embodiment. The belt 561 is used to place the magnetic field source 530 on the subject 562. The magnetic sensor 515 and magnetic field source 530 may be positioned the other way around. The position of the distal part of the ultrasonic endoscope 501 can still be detected properly.

The twentieth embodiment of the present invention will be described below.

In this embodiment, the description of components identical to those of the sixteenth embodiment will be omitted. Different points alone will be described mainly.

This embodiment will be described in conjunction with FIG. 39.

This embodiment is, similarly to the nineteenth embodiment, concerned with another configuration in which the reference position of a subject and the position and direction of an ultrasonic probe can be grasped accurately.

Figure 39:
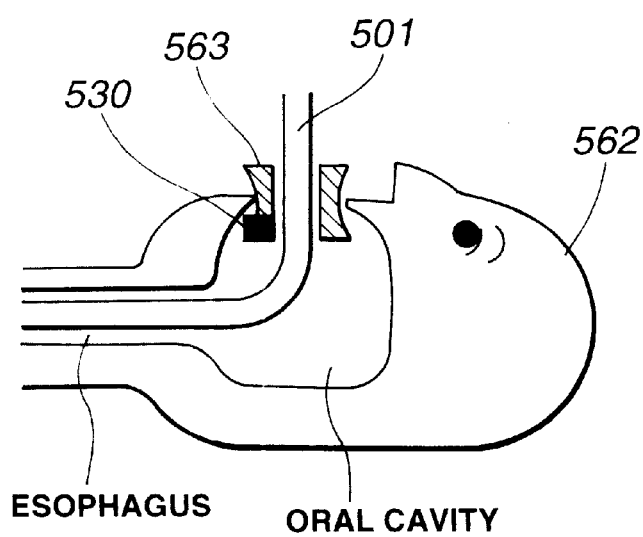
FIG. 39 is an explanatory diagram relating to the twentieth embodiment of the present invention and showing the layout of components in a subject during ultrasonic diagnosis.

As shown in FIG. 39, in this embodiment, the magnetic field source 530 is fixed to a mouthpiece 563 made of a material not disordering a magnetic field, such as, a plastic. The mouthpiece 563 is held in the mouth of the subject 562 during ultrasonic diagnosis. The ultrasonic endoscope 501 is inserted into a body cavity via the oral cavity and esophagus through the mouthpiece 563.

The other components are identical to those of the sixteenth embodiment.

According to this embodiment, the magnetic field source 530 is fixed to the body of the subject 562 together with the mouthpiece 563 so that the magnetic field source 530 will be located at a certain position near the incisor teeth of the subject 562. The position and direction of the ultrasonic endoscope 501 relative to the incisor teeth serving as the reference position of the subject can be measured more accurately. It is therefore easy to identify the position of a lesion during a re-examination.

At this time, in this embodiment, the magnetic field source 530 is made of a material not disordering a magnetic field, such as, a plastic, and bonded to the mouthpiece 563 held in the mouth of the subject. Unlike when the magnetic field source 530 is mounted on a bed or the like, there is no fear of disordering a magnetic field. Moreover, unlike when the magnetic field source 530 is incorporated in an arm or the like formed on a host processor or the like, the magnetic sensor 515 and magnetic field source 530 are located mutually closely. There is therefore no fear that the precision in detecting the position and direction of the ultrasonic endoscope 501 may deteriorate. The position and direction of the ultrasonic endoscope 501 can be measured accurately with high precision by means of the magnetic sensor 515.

The other operations and advantages are identical to those of the sixteenth embodiment.

In this embodiment, similarly to the sixteenth embodiment, the magnetic sensor 515 is incorporated in the distal part of the ultrasonic endoscope 501. The magnetic field source 530 is bonded to the mouthpiece 563 to be held in the mouth of the subject 562. The positions of the magnetic sensor 515 and magnetic field source 530 may be reversed. The position of the distal part of the ultrasonic endoscope 501 can still be detected properly.

Moreover, in the nineteenth and twentieth embodiments, the magnetic sensor 515 and magnetic field source 530 number one. Alternatively, a plurality of magnetic sensors 515 may be included. For example, similarly to the nineteenth embodiment, the magnetic field source 530 may be bonded to a belt to be bound about a subject's body. The magnetic sensors 515 may be incorporated in the distal part of the ultrasonic endoscope 501 and bonded to the mouthpiece 563. Otherwise, the magnetic field source and magnetic sensor may be positioned the other way around. Nevertheless, the position of the distal part of the ultrasonic endoscope 501 and the reference position of the subject can still be detected properly.

In the aforesaid embodiments, an ultrasonic endoscope having an observation optical system such as a CCD camera is adopted as an intracorporeal ultrasonic probe. The embodiments can also be adapted to an ultrasonic probe devoid of the optical system.

Moreover, the described configurations include an ultrasonic endoscope whose mechanical structure is intended to carry out radial scanning. A scanning technique using ultrasonic waves may be a linear scan, sector scan, or convex scan. The embodiments can also be adapted to an ultrasonic probe for scanning one surface during one scan. Moreover, the scanned surface may not be a plane but may be a curved surface.

Figure 40:
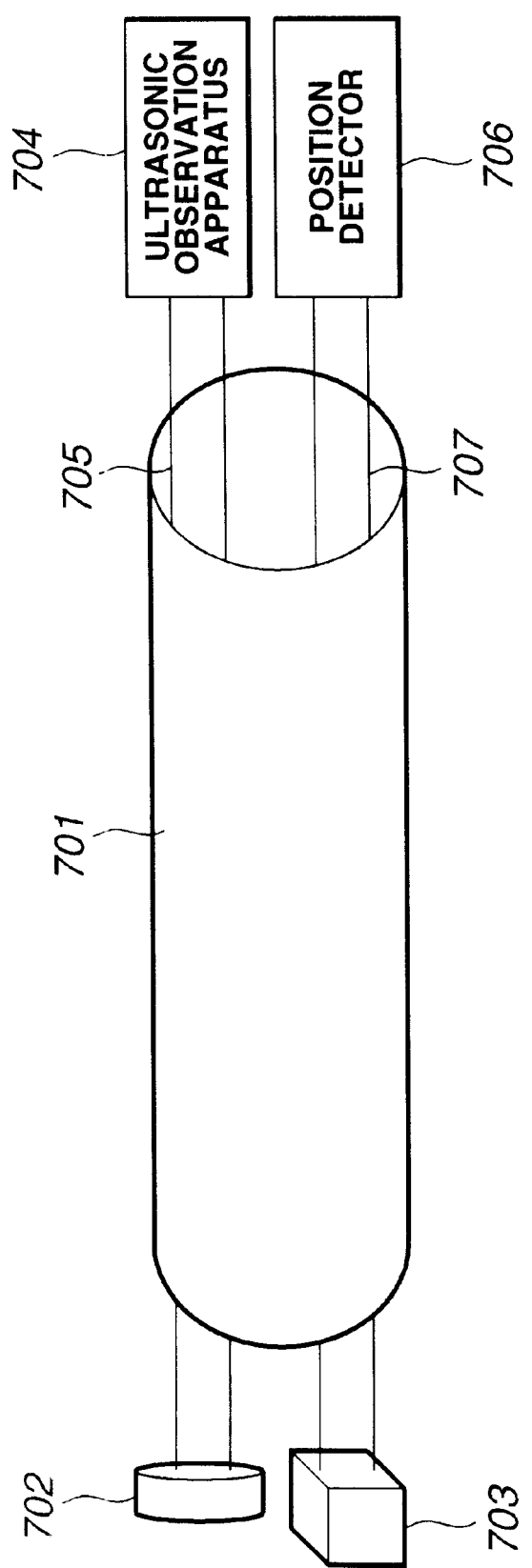
FIG. 40 is a block diagram used to explain a prior art relating to the twenty-first embodiment of the present invention, and schematically showing a transmission path in a portion of a conventional ultrasonic endoscope to be inserted into a body cavity.

In a conventional ultrasonic diagnosis system disclosed in Japanese Unexamined Patent Publication No. 6-261900, as shown in FIG. 40, a signal line 705 lies through a portion (insertion unit) 701 of the ultrasonic endoscope to be inserted into a body cavity. Herein, the signal line 705 serves as a transmission path for a typical ultrasonic endoscope over which a signal is transferred between an ultrasonic transducer 702 and ultrasonic observation apparatus 704. In addition, a signal line 707 over which a position detection signal is transferred between a position sensor 703 and position detector 706 lies through the portion 701.

In addition to the transmission path over which an echo signal sent from the ultrasonic transducer is transmitted, the transmission path over which the position detection signal sent from the position sensor is transmitted must be laid in the insertion unit of the ultrasonic endoscope. The portion of the ultrasonic endoscope to be inserted into a body cavity becomes large in diameter. This poses a problem that a subject must bear a load.

In consideration of the situation, ultrasonic diagnosis systems having a position sensor incorporated in the distal part of an insertion unit to be inserted into a body cavity, and making it possible to reduce the diameter of the insertion unit will be described as the twenty-first and twenty-second embodiments.

The twenty-first embodiment of the present invention will be described below.

Figure 41:
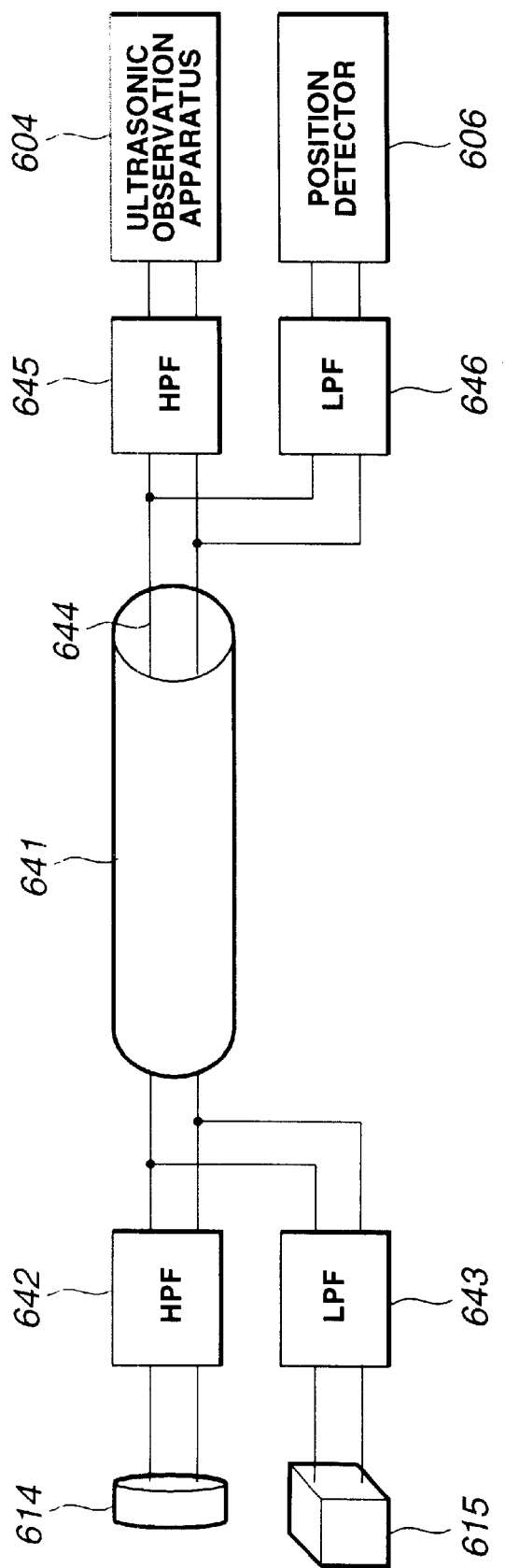
FIG. 41 is a block diagram relating to the twenty-first embodiment of the present invention, and schematically showing a transmission path in an insertion unit of an ultrasonic endoscope.

FIG. 41 schematically shows a transmission path in a portion of an ultrasonic endoscope 601 to be inserted into a body cavity (tortuous tube 641 of an insertion unit 609).

A high-pass filter (HPF) 642 is connected to an ultrasonic transducer 614, and a low-pass filter (LPF) 643 is connected to a magnetic sensor 615. The other terminals of the high-pass filter 642 and low-pass filter 643 are coupled in parallel to one signal line 644 so that signal channels can be merged into one channel in the distal part of the insertion unit 609.

The signal line 644 is passed through the tortuous tube 641 and extended to a proximal part of the ultrasonic endoscope. A high-pass filter 645 and low-pass filter 646 are coupled in parallel to the proximal end of the signal line 644. Thus, the signal channel is bifurcated in an operation unit 610 or ultrasound connector 627. The other terminal of the high-pass filter 645 is connected to the ultrasonic observation apparatus 604, and the other terminal of the low-pass filter 646 is connected to the position detector 606.

As mentioned above, in this embodiment, a signal transmission path required for ultrasonic observation is limited to the one signal line 644 in order to decrease the outer diameter of the insertion unit 609. A magnetic field detection signal output from the magnetic sensor 615, and a driving signal and an ultrasonic signal such as an echo signal which are input or output to or from the ultrasonic transducer 614 are transmitted over the signal line 644. Thus, the number of cables in the tortuous tube 641 is decreased.

Next, the operations of the ultrasonic diagnosis system of this embodiment having the foregoing configuration will be described.

The operations thereof concerning transmission of an ultrasonic signal will be described in conjunction with FIG. 41.

The ultrasonic transducer 614 is driven with a pulsating signal whose frequency ranges from several megahertz to several tens of megahertz. A received echo signal is also a signal within the same frequency band. On the other hand, frequencies equal to or lower than several hundreds of kilohertz are assigned to an output signal of the magnetic sensor 614.

A driving signal transmitted from the ultrasonic observation apparatus 604 passes through the high-pass filter 645 and enters the signal line 644. The driving signal is then merged with an output signal of the magnetic sensor 615. At this time, the driving signal will not flow into the position detector 606 because of the low-pass filter 646. The driving signal transmitted to the distal part of the tortuous tube 641 over the signal line 644 lying through the tortuous tube 641 is supplied to the ultrasonic transducer 614 via the high-pass filter 642. The ultrasonic transducer 614 is then driven. Moreover, an echo signal received by the ultrasonic transducer 614 is sent to the ultrasonic observation apparatus 604 along a route opposite to the route of the driving signal or a route passing through the high-pass filter 642, signal line 644, and high-pass filter 645. The ultrasonic observation apparatus 604 produces a tomographic image signal concerning an examined region.

A magnetic field detection signal is produced by the magnetic sensor 615 as a result of detection of a magnetic field generated by the magnetic field source 630. The magnetic field detection signal passes through the low-pass filter 643 and enters the signal line 644 while being unaffected by the driving signal and an ultrasonic signal such as an echo signal. The magnetic field detection signal is then merged with the ultrasonic signal and transmitted to the optimal part of the tortuous tube 641 over the signal line 644 lying through the tortuous tube 641. The magnetic field detection signal is sent to the position detector 606 via the low-pass filter 646, and processed by the position detector 606. This results in position data.

As mentioned above, according to this embodiment, a driving signal required for ultrasonic observation or an ultrasonic signal such as an echo signal and a magnetic field detection signal required for detecting the position of the ultrasonic probe are separated from each other as signals of different frequency bands by means of the high-pass filter and low-pass filter. The signals are transmitted over the same signal line. This results in a decreased number of signal lines in the insertion unit. The outer diameter of the insertion unit can be reduced. An ultrasonic diagnosis system having a position detector incorporated in the distal part of the insertion unit can be realized without the necessity of increasing the outer diameter of the insertion unit to be inserted into a body cavity.

The twenty-second embodiment of the present invention will be described below.

In this embodiment, the description of components identical to those of the twenty-first embodiment will be omitted. Different points alone will be described below.

Figure 42:
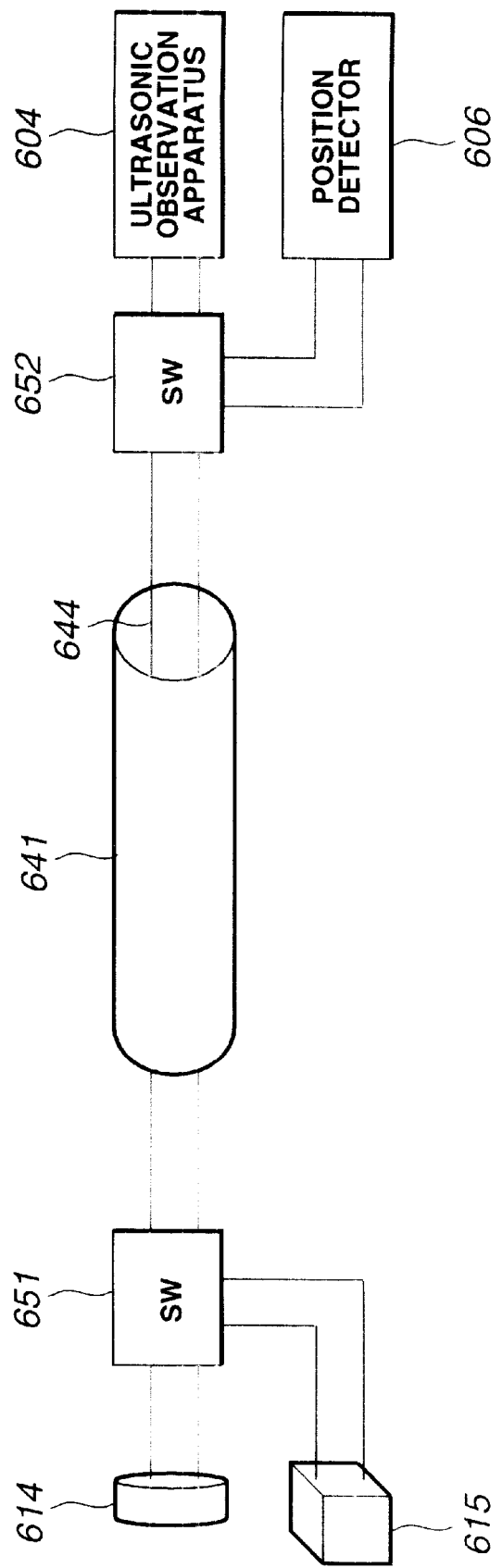
FIG. 42 is a block diagram relating to the twenty-second embodiment of the present invention, and schematically showing a transmission path in an insertion unit of an ultrasonic endoscope.

This embodiment will be described in conjunction with FIG. 42.

This embodiment provides another example of a transmission path in an insertion unit of an ultrasonic endoscope. Components different from those of the twenty-first embodiment will be described below.

The ultrasonic transducer 614 and magnetic sensor 615 are connected to a switch (SW) 651. Input/output signals of the ultrasonic transducer and magnetic sensor are switched alternately. The other terminal of the switch 651 is coupled to the signal line 644. Thus, signal channels are thus merged into one channel in the distal part of the insertion unit 609. The signal line 644 is passed through the tortuous tube 641 and extended to the proximal part of the tortuous tube. A switch 652 is coupled to the proximal end of the signal line 644. The ultrasonic observation apparatus 604 and position detector 606 are connected to the other terminal of the switch 652. The signal channel is then bifurcated in the operation unit 610 or ultrasound connector 627.

As mentioned above, in this embodiment, the one signal line 644 is used as a signal transmission path required for ultrasonic observation in an effort to decrease the outer diameter of the insertion unit 609. A magnetic field detection signal output from the magnetic sensor 615 and a driving signal and an ultrasonic signal such as an echo signal input or output to or from the ultrasonic transducer 614 are switched by the switches 651 and 652 at regular intervals. Thus, the number of cables in the tortuous tube 641 is decreased.

According to this embodiment, for radial scanning using ultrasonic waves, the switches 651 and 652 are changed over to the ultrasonic transducer 614 and ultrasonic observation apparatus 604. A driving signal sent from the ultrasonic observation apparatus 604 is supplied to the ultrasonic transducer 614 over the signal line 644. An echo signal received by the ultrasonic transducer 614 is transmitted to the ultrasonic observation apparatus 604 over the signal line 644.

Every time the ultrasonic transducer 614 completes one turn for radial scanning, the switches 651 and 652 are changed over to the magnetic sensor 615 and position detector 606. A magnetic field detection signal sent from the magnetic sensor 615 is transmitted to the position detector 606 over the signal line 644. The position of the ultrasonic probe is thus measured.

When the position measurement is completed, the switches 651 and 652 are changed over to the ultrasonic transducer 614 and ultrasonic observation apparatus 604. An echo signal resulting from radial scanning performed using ultrasonic waves is transmitted again to the ultrasonic observation apparatus 604.

The above operations are repeated, whereby position measurement and acquisition of echo data are carried out in time-sharing using the common transmission path. An ultrasonic tomographic image of an examined region is thus produced.

In this embodiment, a driving signal required for ultrasonic observation or an ultrasonic signal such as an echo signal and a magnetic field detection signal employed in detecting the position of the ultrasonic probe are switched in time-sharing. The signals are transmitted over the same signal line. Consequently, the number of signal lines in the insertion unit can be decreased, and the outer diameter of the insertion unit can be made smaller. Eventually, an ultrasonic diagnosis system having a position detector incorporated in the distal part of an insertion unit can be realized without the necessity of increasing the outer diameter of the insertion unit to be inserted into a body cavity.

The present invention has been described so far. The present invention will not be limited to the aforesaid embodiments. Variants will also belong to the present invention as long as they conform to the gist of the present invention.

What is claimed is:

1. An ultrasonic endoscope, comprising:
    an ultrasonic transducer for producing an ultrasonic tomographic image;
    a magnetic sensor for detecting a position; and
    a distal part including said ultrasonic transducer and said magnetic sensor, at least one of said ultrasonic transducer and said magnetic sensor being fixedly disposed at the distal part, wherein portions of said endoscope peripheral to said magnetic sensor, which are unrelated to electrical conduction, are made of a non-conductive material.

2. An ultrasonic endoscope according to claim 1, wherein said distal part is composed of a distal body that is a frame of said distal part, and a housing made of a non-conductive material for accommodating said ultrasonic transducer.

3. An ultrasonic endoscope according to claim 1, wherein said ultrasonic transducer, a signal line coupled to said ultrasonic transducer, a magnetic sensor, and a signal line coupled to said magnetic sensor are made of a conductive material.

4. An ultrasonic endoscope, comprising:
    an ultrasonic transmitter receiver for transmitting or receiving ultrasonic waves and producing an ultrasonic tomographic image;
    a position detector for detecting the position of said ultrasonic transmitter receiver using a magnetic field generated externally to said endoscope;
    wherein all portions of said ultrasonic endoscope unrelated to electrical conduction are made of a non-conductive material.

5. An ultrasonic diagnosis system, comprising:
    a magnetic field generator for generating a magnetic field;
    an ultrasonic endoscope including an ultrasonic transmitter receiver for transmitting or receiving ultrasonic waves to produce an ultrasonic tomographic image, and a magnetic sensor for sensing a magnetic field generated by said magnetic field generator so as to detect the position of said ultrasonic transmitter receiver, and having all regions thereof unrelated to electrical conduction made of a non-conductive material;
    means for producing an ultrasonic tomographic image according to at least an echo signal produced by said ultrasonic transmitter receiver;
    means for synthesizing ultrasonic tomographic images according to information of a position and direction detected using a signal sent from said magnetic sensor, and thus producing a three-dimensional ultrasonic image; and peripheral equipment for said ultrasonic endoscope having all regions thereof which are unrelated to electrical conduction made of a non-conductive material.

6. An ultrasonic diagnosis system according to claim 5, wherein said peripheral equipment includes a mouthpiece made of a non-conductive material for introducing an ultrasonic endoscope.

7. An ultrasonic diagnosis system according to claim 6, wherein said peripheral equipment includes a housing of said magnetic field generator.

8. An ultrasonic diagnosis system according to claim 6, wherein said peripheral equipment includes a locking belt for locking said magnetic field generator on a subject.

9. An ultrasonic diagnosis system according to claim 6, said peripheral equipment includes a bed used to examine a subject.

10. An ultrasonic diagnosis system, comprising:

an ultrasonic endoscope including a passage and an ultrasonic transducer, and producing an ultrasonic tomographic image by moving said ultrasonic transducer for scanning;

a position detection catheter passed through said passage in said ultrasonic endoscope when used, and having a position detecting-means included in the distal part thereof; and a three-dimensional processor for acquiring a position signal sent from said position detecting element and a plurality of consecutive ultrasonic tomographic images produced by said ultrasonic endoscope, and thus structuring three-dimensional data.

11. An ultrasonic diagnosis system according to claim 10, wherein said three-dimensional processor constructs a three-dimensional image according to said three-dimensional data.

12. An ultrasonic diagnosis system according to claim 11, wherein said position detecting element is a magnetic sensor for detecting a position using a magnetic field.

13. An ultrasonic diagnosis system according to claim 12, wherein said position detection catheter and the distal part of said ultrasonic endoscope are made of a non-conductive material.

14. An ultrasonic diagnosis system according to claim 11, wherein said position detecting element is a magnetic field source for generating a magnetic field, and a magnetic sensor for detecting the magnetic field generated by said magnetic field source is included.

15. An ultrasonic diagnosis system according to claim 14, wherein said position detection catheter and the distal part of said ultrasonic endoscope are made of a non-conductive material.

16. An ultrasonic diagnosis system according to claim 11, wherein said position detecting element is an acceleration sensor for detecting a position according to an acceleration.

17. An ultrasonic diagnosis system according to claim 10, wherein said position detecting element is a magnetic sensor for detecting a position using a magnetic field.

18. An ultrasonic diagnosis system according to claim 17, wherein said position detection catheter and the distal part of said ultrasonic endoscope are made of a non-conductive material.

19. An ultrasonic diagnosis system according to claim 10, wherein said position detecting element is a magnetic field source for generating a magnetic field, and a magnetic sensor for detecting the magnetic field generated by said magnetic field source is included.

20. An ultrasonic diagnosis system according to claim 19, wherein said position detection catheter and the distal part of said ultrasonic endoscope are made of a non-conductive material.

21. An ultrasonic diagnosis system according to claim 10, wherein said position detecting element is an acceleration sensor for detecting a position according to an acceleration.

* * * * *